US005169432A

United States Patent [19]

Auinbauh et al.

[11] Patent Number: 5,169,432

[45] Date of Patent: Dec. 8, 1992

[54] SUBSTITUTED 2,6-SUBSTITUTED PYRIDINE HERBICIDES

[75] Inventors: Susan M. Auinbauh, St. Louis; Len F. Lee; Karey A. Van Sant, both of St. Charles, all of Mo.

[73] Assignee: Monsanto Company, St. Louis, Mo.

[21] Appl. No.: 705,548

[22] Filed: May 23, 1991

[51] Int. Cl.[5] .................... A01N 43/40; C07D 295/00

[52] U.S. Cl. .................................... 71/94; 544/124; 546/318; 546/313; 548/237; 548/262.4; 548/579; 548/373.1

[58] Field of Search ................ 546/318, 313; 544/124; 548/579, 237, 374, 262.4; 71/94

[56] References Cited

U.S. PATENT DOCUMENTS

| | | | |
|---|---|---|---|
| 1,944,412 | 1/1934 | Dohrn et al. | 546/299 |
| 3,629,270 | 12/1971 | Gante et al. | 546/283 |
| 3,637,716 | 1/1972 | Bimber | 546/310 |
| 3,651,070 | 3/1972 | Granito | 546/298 |
| 3,748,334 | 7/1973 | Rigterink | 546/303 |
| 5,114,465 | 5/1992 | Bryant et al. | 71/94 |

*Primary Examiner*—Jose G. Dees
*Assistant Examiner*—Joseph M. Conrad, III
*Attorney, Agent, or Firm*—Grace L. Bonner; Howard C. Stanley

[57] ABSTRACT

Substituted pyridines having at the 3 or 5 position a carbonyl oxy(thio)ester or a heterocyclocarbonyl and at the other a substituted alkyl group, herbicidal compositions and methods of use thereof.

16 Claims, No Drawings

SUBSTITUTED 2,6-SUBSTITUTED PYRIDINE HERBICIDES

This invention relates to novel substituted pyridinecarboxylic acid derivatives having a wide range of activity as herbicides.

Pyridine derivatives have, for many years, been investigated for use in biological sciences. For example, 2,6-bis(trifluoromethyl)-4-pyridinols have been found useful as herbicides and fungicides as disclosed in U.S. Pat. No. 3,748,334. Such compounds are characterized by substitution in the 4-position by a hydroxy radical. In addition to the hydroxy radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO patent 44,262 there are disclosed 2,6-dialkyl-3-phenylcarbamyl-5-pyridinecarboxylates and 5-cyano-compounds useful as herbicides. There is no disclosure of the 2-haloalkyl radicals or any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4-position is occupied by a silver salt, U.S. Pat. No. 1,944,412 discloses that such compounds have been utilized in the production of X-ray pictures with intravenous injection of such compounds.

Pyridinedicarboxylate compounds useful as herbicides are described in U.S. Pat. No. 4,692,184. These compounds have fluorinated methyl groups at the 2- and 6-positions and carboxylic acid derivative at the 3- and 5-positions.

Other pyridinedicarboxylate compounds including pyrazole amides are disclosed in U.S. Pat. No. 4,698,093. U.S. Pat. Nos. 4,066,438 and 4,180,395 disclose various herbicidal polyhalo substituted pyridyloxy compounds.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

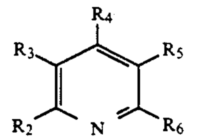

wherein $R_2$ and $R_6$ are independently bromoalkyl, chloroalkyl, fluoroalkyl, chlorofluoroalkyl, or alkoxy, provided that at least one of $R_2$ and $R_6$ is a fluoroalkyl; $R_4$ is alkyl, cycloalkylalkyl, alkylthioalkyl, cycloalkyl, alkoxyalkyl, or dialkylaminoalkyl; one of $R_3$ and $R_5$ is —C(O)—Y and the other is

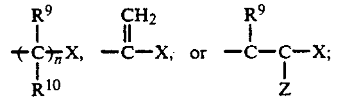

X is halogen, —OH, $—N_3$, $—SR^{11}$, $—OR^{11}$, $—NR^{12}R^{13}$, $—S(O)R^{11}$, $—S(O)_2R^{11}$, —CN, $—C(O)OR^{11}$, $—C(S)NH_2$, $—OC(O)R^8$, $—C(=NR^{12})SR^{11}$,

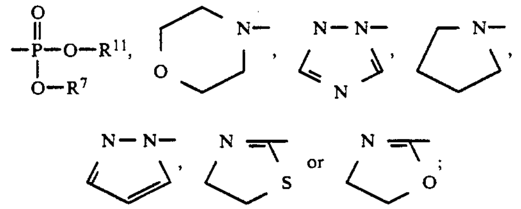

Y is alkylthio, alkoxy,e or a N-containing heterocycle; Z is hydrogen, alkyl, or nitrile; $R^9$ and $R^{10}$ are independently hydrogen, alkyl, alkenyl, or alkynyl; $R^{11}$ and $R^7$ are independently alkyl; $R^{12}$ and $R^{13}$ are independently hydrogen or alkyl; $R^8$ is alkyl or haloalkyl; and n is an integer from 1 to 3 inclusive; provided that when n is 1 and $R^9$ and $R^{10}$ are each hydrogen, X is not —OH.

The term alkyl, alkenyl, alkynyl, alkylthio, alkoxy or like group as used herein means a group containing1-7 carbon atoms in straight or branched chain form. Specifically, the alkyl group may be methyl, ethyl, propyl, isopropyl, butyl, isobutyl, pentyl, isopentyl or hexyl; the alkoxy group may be methoxy, ethoxy, propoxy, isopropoxy; the alkylthio group may be methylthio, ethylthio, propylthio, isopropylthio, butylthio or pentylthio. An alkenyl or alkynyl group has 3 to 7 carbon atoms and may be vinyl, allyl, isopropenyl, 2-butenyl, 1,3-butadienyl, 2-pentenyl, 1,4-pentadienyl, 1,6-heptadienyl, 1-hexenyl, ethynyl, 2-propynyl, etc.

The term "halo" or cognates thereof include chlorine, bromine, fluorine and iodine.

Examples of "cycloalkyl" as used herein include cyclopropyl, cyclobutyl, cyclopentyl, and cyclohexyl.

Examples of "haloalkyl" as used herein include chloromethyl, bromomethyl, dichloromethyl, dibromomethyl, trifluoromethyl and the like.

Examples of "alkoxyalkyl" as used herein include methoxymethyl, ethoxymethyl, propoxymethyl, butoxymethyl and the like.

Examples of "dialkylaminoalkyl" as used herein include N,N-dimethylaminomethyl and N,N-diethylaminomethyl.

Examples of "alkylthioalkyl" as used herein include methylthiomethyl, ethylthiomethyl, methylthioethyl, ethylthioethyl and the like.

The term "cycloalkylalkyl" means a $C_1$–$C_2$ alkyl group substituted with a $C_3$–$C_6$ cycloalkyl group, such as cyclopropylmethyl, cyclopropylethyl, cyclobutylmethyl, cyclopentylethyl, and so forth.

DETAILED DESCRIPTION OF THE INVENTION

The novel herbicidal compounds of this invention are readily prepared from pyridinemethanols generally disclosed as Formula X of U.S. Pat. No. 4,692,184, the full text of which is incorporated herein by reference, or from pyridinecarboxaldehydes (Formula XI therein) prepared from the pyridinemethanols by reaction with pyridinium chlorochromate (PCC). Pyridinemethanols are derived from 5-chlorocarbonyl-3-pyridinecarboxylates (Formula IV, Examples 44–51 therein) by reaction with sodium borohydride. These procedures are illustrated by the following schematic and are detailed in examples given below.

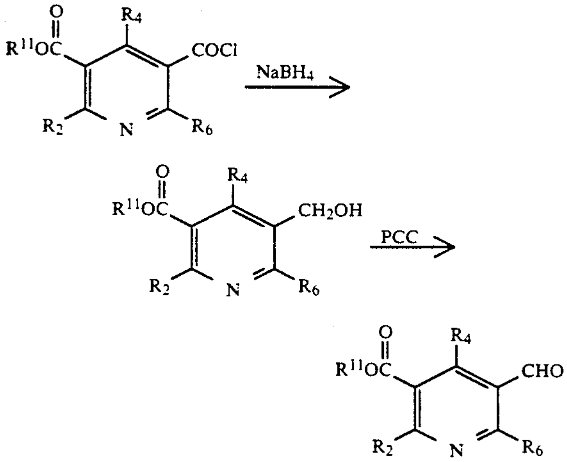

Pyridinemethanols may be used to prepare the chloromethylpyridines of the present invention by reaction with thionyl chloride. From the chloromethylpyridines, other compounds of the present invention may be prepared by usual methods, such as pyridineacetonitriles (by reaction with sodium cyanide), which may then be alkylated to produce α-substituted-pyridineacetonitriles, for example, using methyl iodide, allyl bromide or propargyl bromide under phase transfer catalysis conditions. The chloromethylpyridines may also be reacted with various nucleophiles under nucleophilic addition conditions to produce many compounds of the present invention.

Pyridinecarboxaldehydes may be used to prepare α-substituted pyridinemethanols by reaction with an alkyl, allyl, or vinyl Grignard reagent; substituted vinylpyridines by reaction with the appropriate Wittig reagent; 2,2-disubstituted-vinylpyridines by reaction with a nitrile having the desired substituents. α-Substituted pyridinemethanols may be further reacted with thionyl chloride to produce α-substituted chloromethylpyridines, which may, like the unsubstituted analogs discussed above, be reacted with various nucleophiles under nucleophilic addition conditions to prepare various compounds of the present invention.

α-Substituted pyridineacetonitriles may alternatively be produced from α-substituted chloromethylpyridines by reaction with sodium cyanide. α-Substituted pyridineacetonitriles produced by either method may be used to prepare pyridylalkylthioamides under thioamide-forming conditions, for example, in the presence of a catalytic amount of diethylamine in DMF. Pyridylalkylthioamides when alkylated, for example by using alkyl halides, yield thioimidates. Either of the following structural types may be produced depending on the conditions.

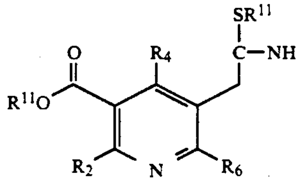

or

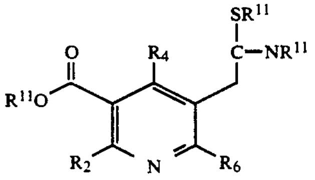

3-Pyridinemethanols or α-substituted pyridinemethanols may be alkylated under alkylating conditions, for example, using sodium hydride as a base or using phase transfer catalysis, to yield alkoxyalkylpyridines.

Pyridineacetonitriles may undergo alcoholysis in the presence of sulfuric acid to yield pyridineacetates, which may then be alkylated, for example, under phase transfer catalysis conditions, to produce α-substituted pyridineacetates.

Pyridinemethanols may also be used to produce the pyridinemethyl esters by reaction with the appropriate acid chloride or acid anhydride.

1-Pyridylethanols, one type of the α-substituted pyridinemethanols discussed above, may be dehydrated under dehydrating conditions to yield vinylpyridines, which may be further reacted under halogenating conditions to prepare 1,2-dibromoethylpyridines. These compounds may then be dehydrobrominated under dehydrohalogenation conditions to produce 2-pyridylvinyl bromides.

The 2-pyridylvinyl bromides may in turn be dehydrohalogenated under dehydrohalogenation conditions to prepare pyridineacetylenes. Pyridineacetylenes may be reacted with amines to give 2-pyridylvinylamines. Hydrogenation of 2-pyridylvinylamines yielded 2-pyridylethylamines.

Vinylpyridines may also be reacted with hydrogen bromide and benzoylperoxide to produce 2-bromoethylpyridines. 2-Bromoethylpyridines may be reacted with various nucleophiles under nucleophilic addition conditions to yield 2-substituted ethylpyridines.

Reactions of 1,2-dibromoethylpyridines with oxygen and sulfur nucleophiles under nucleophilic addition conditions yielded 2-substituted vinylpyridines.

Pyridylmethyl alkyl sulfides, prepared as described above by reaction of sulfur nucleophiles with chloromethylpyridines, may be oxidized under oxidation conditions, for example with m-chloroperbenzoic acid (MCPBA) to produce the corresponding sulfoxides or sulfones, depending on the conditions. These sulfones may be alkylated, for example under phase transfer catalysis conditions, to yield α-substituted sulfones.

The following examples illustrated these preparation methods, but are not limiting to the scope of the claims in any way.

EXAMPLE A

Preparation of Pyridinemethanols To a 60 ° C. solution of 0.22 mol methyl 5-(chlorocarbonyl)-6-(difluoromethyl)-2-(trifluoromethyl)-4-alkyl-3-pyridinecarboxylate, prepared as described in U.S. Pat. Nos. 4,692,184 and 4,988,384, in 300 mL dimethoxyethane (DME) was added 0.65 mol sodium borohydride over two hours. The reaction mixture was stirred at 60° C. for an additional hour and poured into 1 L of ice water causing vigorous gas evolution. Conc. HCl was added slowly to quench excess sodium borohydride. After gas evolution subsided the reaction mixture was extracted with methylene chloride (2×500 mL), dried over magnesium sulfate and concentrated. The residue was kugelrohr distilled at 1 torr to give the desired product. Thus were the following compounds prepared:

Compound A1, 3-pyridinecarboxylic acid, 6-(difluoromethyl)-4-ethyl-5-(hydroxymethyl)-2-(trifluoromethyl)-, ethyl ester;

Compound A2, 3-pyridinecarboxylic acid, 6-(difluoromethyl)-4-(2-methylpropyl)-5-(hydroxymethyl)-2-(trifluoromethyl)-, methyl ester;

Compound A3, 3-pyridinecarboxylic acid, 2-(difluoromethyl)-4-(2-methylpropyl)-5-(hydroxymethyl)-6-(trifluoromethyl)-, methyl ester;

Compound A4, 3-pyridinecarboxylic acid, 4-(cyclopropylmethyl)-2-(difluoromethyl)-5-(hydroxymethyl)-6-(trifluoromethyl)-, methyl ester;

Compound A5, 3-pyridinecarboxylic acid, 5-(hydroxymethyl)-2-methoxy-4-(2-methylpropyl)-6-(trifluoromethyl)-, methyl ester;

Compound A6, 3-pyridinecarboxylic acid, 6-(fluoromethyl)-4-(2-methypropyl)-5-(hydroxymethyl)-2-(trifluoromethyl)-, methyl ester.

EXAMPLE B

Preparation of Pyridinecarboxaldehydes To a solution of one equivalent of the appropriate pyridylmethanol in methylene chloride was added 2 equivalents of pyridinium chlorochromate. The reaction mixture was stirred for 1 hour and filtered through Celite. The filtrate was filtered through silica gel and eluted with methylene chloride. The eluent was concentrated in vacuo and kugelrohr distilled at 1 torr (140° C.) to give the desired product. Thus were the following compounds prepared:

Compound B1, 3-pyridinecarboxylic acid, 2-(difluoromethyl)-5-formyl-4-(2-methylpropyl)-6-(trifluoromethyl)-, methyl ester, prepared from Compound A3;

Compound B2, 3-pyridinecarboxylic acid, 4-(cyclopropylmethyl)-2-(difluoromethyl)-5-formyl-6-(trifluoromethyl)-, methyl ester, prepared from Compound A4;

Compound B3, 3-pyridinecarboxylic acid, 6-(difluoromethyl)-5-formyl-4-(2-methylpropyl)-2-(trifluoromethyl)-, methyl ester, prepared from Compound A2;

Compound B4, 3-pyridinecarboxylic acid, 5-formyl-2-methoxy-4-(2-methylpropyl)-6-(trifluoromethyl)-, methyl ester, prepared from Compound A5;

Compound B5, 3-pyridinecarboxylic acid, 6-(fluoromethyl)-5-formyl-4-(2-methylpropyl)-2-(trifluoromethyl)-, methyl ester, prepared from Compound A6;

Compound B6, 3-pyridinecarboxylic acid, 4-(cyclopropylmethyl)-5-formyl-2-methoxy-6-(trifluoromethyl)-, methyl ester, prepared from the corresponding pyridine methanol described in pending U.S. application Ser. No. 07/660,480, filed Feb. 25, 1991, the full text of which is incorporated herein by reference.

EXAMPLE 1

Preparation of 3-Pyridinecarboxylic acid, 5-(chloromethyl)-6-(difluoromethyl)-4-ethyl-2-(trifluoromethyl)-, ethyl ester.

A mixture of 0.03 mol of Compound A1, 0.55 mol thionyl chloride and 0.042 mol pyridine was held at reflux for 20 h and concentrated in vacuo. The residue was stirred with 100 mL ether and 100 mL water. The ether layer was washed with brine, dried over magnesium sulfate and concentrated in vacuo. The residue was kugelrohr distilled at 1 torr to give the desired product. m.p. 54°-55.5° C.

By a similar method the compounds of Examples 2 through 4 were prepared using the starting materials shown.

| Ex. No. | Strtg Mtrl. | Name | Phys. Prop. |
|---|---|---|---|
| 2 | A2 | 3-Pyridinecarboxylic acid, 5-(chloromethyl)-6-(difluoromethyl)-4-(2-methylpropyl)-2-(trifluoromethyl)-, methyl ester | $n_D^{25}$ 1.4630 |
| 3 | A3 | 3-Pyridinecarboxylic acid, 5-(chloromethyl)-2-(difluoromethyl)-4-(2-methylpropyl)-6-(trifluoromethyl)-, methyl ester | $n_D^{25}$ 1.4652 |
| 4 | A4 | 3-Pyridinecarboxylic acid, 5-(chloromethyl)-4-(cyclopropylmethyl)-2-(difluoromethyl)-6-(trifluoromethyl)-, methyl ester | yellow oil |

EXAMPLE 5

Preparation of 3-Pyridinecarboxylic acid, 5-(cyanomethyl-6-(difluoromethyl)-4-ethyl-2-(trifluoromethyl)-, ethyl ester.

A mixture of 0.02 mol Compound 1, 0.06 mol sodium cyanide, and 25 mL DMF was stirred for 2 h and diluted with 100 mL ether. The ether solution was washed successively with water, brine, and saturated sodium bicarbonate, dried over magnesium sulfate and concentrated in vacuo. The residue was kugelrohr distilled at 1 torr to give the desired product or the distillate was further recrystallized from hexane-ether to give the product. m.p. 44°-45.5° C.

By a similar method the compounds of Examples 6 through 8 were prepared using the starting materials shown.

| Ex. No. | Strtg Mtrl. | Name | Phys. Prop. |
|---|---|---|---|
| 6 | Ex. 2 | 3-Pyridinecarboxylic acid, 5-(cyanomethyl)-6-(difluoromethyl)-4-(-2-methylpropyl)-2- | b.p. 120° C., (0.5 torr) |

-continued

| Ex. No. | Strtg Mtrl. | Name | Phys. Prop. |
|---|---|---|---|
| | | (trifluoromethyl)-, methyl ester | |
| & | Ex. 3 | 3-Pyridinecarboxylic acid, 5-(cyanomethyl)-2-(difluoromethyl)-4-(2-methylpropyl)-6-(trifluoromethyl)-, methyl ester | m.p. 68-70° C. |
| 8 | Ex. 4 | 3-Pyridinecarboxylic acid, 5-(cyanomethyl)-4-(cyclopropylmethyl)-2-(difluoromethyl)-6-(trifluoromethyl)-, methyl ester | m.p. 56-57° C. |

EXAMPLE 9

Preparation of 3-Pyridinecarboxylic acid, 5-(1-cyanoethyl)-2-(difluoromethyl)-4-(2-methylpropyl)-6-(trifluoromethyl)-, methyl ester.

To a mixture of 3 mmol of Compound 7, 77 mmol methyl iodide, 0.1 g Aliquat 336 and 20 mL methylene chloride was added 10 mL of 50% sodium hydroxide. The reaction mixture was stirred for 2 h and washed with water. The methylene chloride layer was dried over magnesium sulfate and concentrated. The residue was kugelrohr distillled at 1 torr to give the desired product $n_D^{25}$ 1.4650.

By similar methods were the products of Examples through 18 made using methyl iodide, allyl bromide or propargyl bromide as needed for the desired product. Example 12 was prepared using chloromethyl methyl sulfide instead. Examples 15 through 18 used benzyltriethylammonium chloride as the catalyst.

| Ex. No. | Strtg Mtrl. | Name | Phys. Prop. |
|---|---|---|---|
| 10 | Ex. 7 | 3-Pyridinecarboxylic acid, 5-(1-cyano-3-butenyl)-2-(difluoromethyl)-4-(2-methylpropyl)-6-(trifluoromethyl)-, methyl ester | $n_D^{25}$ 1.4700 |
| 11 | Ex. 7 | 3-Pyridinecarboxylic acid, 5-(1-cyano-3-butynyl)-2-(difluoromethyl)-4-(2-methylpropyl)-6-(trifluoromethyl), methyl ester | $n_D^{25}$ 1.4757 |
| 12 | Ex. 7 | 3-Pyridinecarboxylic acid, 5-(1-cyanoethenyl)-2-(difluoromethyl)-4-(2-methylpropyl)-6-(trifluoromethyl)-, methyl ester | $n_D^{25}$ 1.4702 |
| 13 | Ex. 6 | 3-Pyridinecarboxylic acid, 5-(1-cyanoethyl)-6-(difluoromethyl)-4-(2-methylpropyl)-2-(trifluoromethyl)-, methyl ester | $n_D^{25}$ 1.4636 |
| 14 | Ex. 6 | 3-Pyridinecarboxylic acid, 5-(1-cyano-3-butenyl)-6-(difluoromethyl)-4-(2-methylpropyl)-2-(trifluoromethyl)-, methyl ester | $n_D^{25}$ 1.4699 |
| 15 | Ex. 8 | 3-Pyridinecarboxylic acid, 5-(1-cyanoethyl)-4-(cyclopropylmethyl)-2-(difluoromethyl)-6-(trifluoromethyl)-, methyl ester | $n_D^{25}$ 1.4768 |
| 16 | Ex. 8 | 3-Pyridinecarboxylic acid, 5-(1-cyano-3-butenyl)-4-(cyclopropylmethyl)-2-(difluoromethyl)-6-(trifluoromethyl)-, methyl ester | b.p. 120-130° C. (0.2 torr) |
| 17 | Ex. 8 | 3-Pyridinecarboxylic acid, 5-(1-cyano-3-butynyl)-4-(cyclopropylmethyl)-2-(difluoromethyl)-6-(trifluoromethyl)-, methyl ester | $n_D^{25}$ 1.4872 |
| 18 | Ex. 8 | 3-Pyridinecarboxylic acid, 5-(1-cyanoethenyl)-4-(cyclopropylmethyl)-2-(difluoromethyl)-6-(trifluoromethyl)-, methyl ester | $n_D^{25}$ 1.4801 |

EXAMPLE 19

Preparation of 3-Pyridinecarboxylic acid, 2-(difluoromethyl)-5-(1-hydroxypropyl)-4-(2-methylpropyl)-6-(trifluoromethyl)-, methyl ester.

To 0.033 mol of Compound B1 in 20 mL ether was added 0.042 mol of ethyl magnesium bromide in ether dropwise. The reaction mixture was held at reflux until complete (1 to 18 hours), cooled, and poured into 3 N hydrochloric acid. The mixture was extracted with ether, dried over magnesium sulfate, and concentrated in vacuo. The residue was purified by kugelrohr distillation or HPLC separation to yield an oil.

Using this general method the compounds of Examples 20 through 25 were prepared from the appropriate alkyl, allyl, or vinyl magnesium bromide.

| Ex. No. | Strtg Mtrl. | Name | Phys. Prop. |
|---|---|---|---|
| 20 | B1 | 3-Pyridinecarboxylic acid, 2-(difluoromethyl)-5-(1-hydroxyethyl)-4-(2-methylpropyl)-6-(trifluoromethyl)-, methyl ester | b.p. 100° C. (1 torr) |
| 21 | B1 | 3-Pyridinecarboxylic acid, 2-(difluoromethyl)-5-(1-hydroxy-3-butenyl)-4-(2-methylpropyl)-6-(trifluoromethyl), methyl ester | m.p. 69.5-72.5° C. |
| 22 | B2 | 3-Pyridinecarboxylic acid, 4-(cyclopropylmethyl)-2-(difluoromethyl)-5-(1-hydroxy-2-propenyl)-6-(trifluoromethyl)-, methyl ester | $n_D^{25}$ 1.4827 |
| 23 | B2 | 3-Pyridinecarboxylic acid, 4-(cyclopropylmethyl)-2-(difluoromethyl)-5-(1-hydroxy-3-butyenyl)-6-(trifluoromethyl)-, methyl ester | $n_D^{25}$ 1.4830 |
| 24 | B2 | 3-Pyridinecarboxylic acid, 4-(cyclopropylmethyl)-2-(difluoromethyl)-5-(1-hydroxypropyl)-6-(trifluoromethyl)-, methyl ester | $n_D^{25}$ 1.4721 |
| 25 | B2 | 3-Pyridinecarboxylic acid, 4-(cyclopropylmethyl)-2-(difluoromethyl)-5-(1-hydroxyethyl)-6- | $n_D^{25}$ 1.4735 |

-continued

| Ex. No. | Strtg Mtrl. | Name | Phys. Prop. |
|---|---|---|---|
| | | (trifluoromethyl)-, methyl ester | |

EXAMPLE 26

Preparation of 3-Pyridinecarboxylic acid, 5-(1-chloroethyl)-4-(cyclopropylmethyl)-2-(difluoromethyl)-6-(trifluoromethyl)-, methyl ester.

A mixture of 3.53 g (0.01 mol) of the Compound of Example 25, 3.50 g (0.013 mol) triphenylphosphine, and 50 mL carbontetrachloride was held at reflux overnight, cooled, and filtered. The filtrate was washed successively with 5% hydrochloric acid, saturated sodium bicarbonate, and brine, dried over magnesium sulfate, and concentrated in vacuo. Purification by silica gel chromatography with 5% ethyl acetate-cyclohexane gave 1.44 g (39%) of the desired product as a pale yellow oil. b.p. 87°-90° C. (0.03 torr).

EXAMPLE 27

Preparation of 3-Pyridinecarboxylic acid, 2-(difluoromethyl)-4-(2-methylpropyl)-5-[(methylthio)methyl]-6-(trifluoromethyl)-, methyl ester.

A mixture of 1 equivalent of the Compound of Example 3 and 4 equivalents of sodium methanethiolate in tetrahydrofuran (THF) was stirred at reflux for 2 hours, poured into water and extracted with ether. The ether layer was dried over magnesium sulfate and concentrated in vacuo. The residue was kugelrohr distilled to give the desired product directly or the distillate was further purified by HPLC to give the pure product. $n_D^{25}$ 1.4872.

EXAMPLE 28

Preparation of 3-Pyridinecarboxylic acid, 2-(difluoromethyl)-5-[(dimethoxyphosphinyl)methyl]-4-(2-methylpropyl)-6-(trifluoromethyl)-, methyl ester.

The method of Example 27 was followed using the Compound of Example 3 and a THF solution of 2 equivalents of sodium bis(trimethylsilyl)amide and 2 equivalents of dimethylphosphite, stirred at 10°-15° C. for 4 hours. $n_D^{25}$ 1.4643.

EXAMPLE 29

Preparation of 3-Pyridinecarboxylic acid, 5-[(butylthio)methyl]-6-(difluoromethyl)-4-(2-methylpropyl)-2-(trifluoromethyl)-, methyl ester.

The method of Example 27 was followed using the Compound of Example 2 and a THF solution of 2 equivalent of 1-butanethiol and 1.5 equivalents of triethylamine refluxed for 2 hours. $n_D^{25}$ 1.4762.

EXAMPLE 30

Preparation of 3-Pyridinecarboxylic acid, 6-(difluoromethyl)-4-(2-methylpropyl)-5-[(methylthio)methyl]-2-(trifluoromethyl)-, methyl ester.

The method of Example 27 was followed using the Compound of Example 2 and 4 equivalents of sodium methanethiolate refluxed in THR for 2 hours. $n_D^{25}$ 1.4797.

EXAMPLE 31

Preparation of 3-Pyridinecarboxylic acid, 6-(difluoromethyl)-5-(methoxymethyl)-4-(2-methylpropyl)-2-(trifluoromethyl)-, methyl ester.

The method of Example 27 was followed using the Compound of Example 2 and 3 equivalents of sodium methoxide in methanol stirred at room temperature for 4 hours. $n_D^{25}$ 1.4508.

EXAMPLE 32

Preparation of 3-Pyridinecarboxylic acid, 6-(difluoromethyl)-5-(methylaminomethyl)-4-(2-methylpropyl)-2-(trifluoromethyl)-, methyl ester.

The method of Example 27 was followed using the Compound of Example 2 and a THF solution of 12 equivalents of 40% aqueous methylamine, stirred at room temperature for 8 hours. $n_D^{25}$ 1.4577.

EXAMPLE 33

Preparation of 3-Pyridinecarboxylic acid, 6-(difluoromethyl)-5-[(dimethylamino)methyl]-4-(2-methylpropyl)-2-(trifluoromethyl)-, methyl ester.

The method of Example 27 was followed using the Compound of Example 2 and an ether solution of 27 equivalents of dimethylamine stirred at room temperature for 37 hours. $n_D^{25}$ 1.4565.

EXAMPLE 34

Preparation of 3-Pyridinecarboxylic acid, 5-[(diethylamino)methyl]-6-(difluoromethyl)-4-(2-methylpropyl)-2-(trifloromethyl)-, methyl ester.

The method of Example 27 was followed using the Compound of Example 2 and 8 equivalents of diethylamine refluxed in THF for 24 hours. $n_D^{25}$ 1.4597.

EXAMPLE 35

Preparation of 3-Pyridinecarboxylic acid, 2-(difluoromethyl)-5-(methoxymethyl)-4-(2-methylpropyl)-6-(trifluoromethyl)-, methyl ester.

The method of Example 27 was followed using the Compound of Example 3 and 1 equivalent of sodium hydroxide refluxed in methanol for 20 hours. b.p. 95° C. (0.07 torr).

EXAMPLE 36

Preparation of 3-Pyridinecarboxylic acid, 2-(difluoromethyl)-4-(2-methylpropyl)-5-(1H-pyrazol-1-ylmethyl)-6-(trifluoromethyl)-, methyl ester.

The method of Example 27 was followed using the Compound of Example 3 and a THF solution of 1 equivalent of pyrazole and 2 equivalents of lithium bis(trimethylsilyl)amide, stirred at room temperature for 20 hours. $n_D^{25}$ 1.5851.

EXAMPLE 37

Preparation of 3-Pyridinecarboxylic acid, 2-(difluoromethyl)-4-(2-methylpropyl)-5-[[(1-methylethyl)thio]methyl]-6-(trifluoromethyl)-, methyl ester.

The method of Example 27 was followed using the Compound of Example 3 and a THF solution of 1 equivalent of 2-propanethiol and 1 equivalent of triethylamine stirred at room temperature for 20 hours. b.p. 135° C. (0.3 torr).

EXAMPLE 38

Preparation of 3-Pyridinecarboxylic acid, 2-(difluoromethyl)-4-(2-methylpropyl)-5-(4-morpholinylmethyl)-6-(trifluoromethyl)-, methyl ester.

The method of Example 27 was followed using the Compound of Example 3 and 3 equivalents of morpholine refluxed in THF for 20 hours. b.p. 135 ° C (0.15 torr).

EXAMPLE 39

Preparation of 3-Pyridinecarboxylic acid, 2-(difluoromethyl)-4-(2-methylpropyl)-5-(1H-1,2,4-triazol-1-ylmethyl)-6-(trifluoromethyl)-, methyl ester.

The method of Example 27 was followed using the Compound of Example 3 and a THF solution of 1 equivalent of triazole and 2 equivalents of lithium bis(-trimethylsilyl)amide stirred at room temperature for 20 hours. b.p. 85°-90° C. (0.15 torr).

EXAMPLE 40

Preparation of 3-Pyridinecarboxylic acid, 2-(difluoromethyl)-5-[(methylamino)methyl]-4-(2-methylpropyl)-6-(trifluoromethyl)-, methyl ester.

The title compound was prepared by passing 170 equivalents of gaseous methylamine through a solution of the Compound of Example 3 in THF solution at room temperature for 5 hours. b.p. 113° C. (0.25 torr).

EXAMPLE 41

Preparation of 3-Pyridinecarboxylic acid, 4-(cyclopropylmethyl)-2-(difluoromethyl)-5-[(dimethylamino)-methyl]-6-(trifluoromethyl)-, methyl ester.

The method of Example 27 was followed using the Compound of Example 4 and 3 equivalents of dimethylamine in THF stirred at room temperature overnight. The product was recovered as a yellow oil.

EXAMPLE 42

Preparation of 3-Pyridinecarboxylic acid, 5-[[bis(2-methylpropyl)amino]methyl]-4-(cyclopropylmethyl)-2-(difluoromethyl)-6-(trifluoromethyl)-, methyl ester.

The method of Example 27 was followed using 0.0i mol of the Compound of Example 4 and 15 mL diisobutylamine stirred at 65° C. for 24 hours. m.p. 71°-73° C.

EXAMPLE 43

Preparation of 3-Pyridinecarboxylic acid, 4-(cyclopropylmethyl)-5-[(diethylamino)methyl]-2-(difluoromethyl)-6-(trifluoromethyl)-, methyl ester.

The method of Example 27 was followed using 0.01 mol of the Compound of Example 4 and 15 mL of diethylamine stirred at room temperature for 3 days. $N_D^{25}$ 1.4691.

EXAMPLE 44

Preparation of 3-Pyridinecarboxylic acid, 5-[[bis(1-methylethyl)amino]methyl]-4-(cyclopropylmethyl)-2-(difluoromethyl)-6-(trifluoromethyl)-, methyl ester.

The method of Example 27 was followed using 0.01 mol of the Compound of Example 4 and 15 mL of diisopropylamine stirred at reflux for 24 hours. $n_D^{25}$ 1.4704.

EXAMPLE 45

Preparation of 3-Pyridinecarboxylic acid, 4-(cyclopropylmethyl)-2-(difluoromethyl)-5-[(ethylmethylamino)methyl]-6-(trifluoromethyl)-, methyl ester.

The method of Example 27 was followed using 0.01 mol of the Compound of Example 4 and 0.042 mol of N-ethylmethylamine stirred at room temperature for 3 days. $n_D^{25}$ 1 4675.

EXAMPLE 46

Preparation of 3-Pyridinecarboxylic acid, 2-(difluoromethyl)-4-(2-methylpropyl)-5-[[(2-methylpropyl)thio]methyl]-6-(trifluoromethyl)-, methyl ester.

The method of Example 27 was followed using 9.2 mmol of the Compound of Example 3 and a solution prepared from 26 mmol of sodium metal and 29 mmol of 2-methyl-1-propanethiol and 25 mL of methanol stirred at room temperature for 18 hours. $n_D^{25}$ 1.4762.

EXAMPLE 47

Preparation of 3-Pyridinecarboxylic acid, 2-(difluoromethyl)-5-[(ethylthio)methyl]-4-(2-methylpropyl)-6-(trifluoromethyl)-, methyl ester.

The method of Example 27 was followed using 20 mmol of the Compound of Example 3, a solution prepared from 48 mmol of sodium metal, and 76 mmol of ethanethiol and 50 mL of methanol stirred at room temperature for 18 hours. $n_D^{25}$ 1.4796.

EXAMPLE 48

Preparation of 3-Pyridinecarboxylic acid, 2-(difluoromethyl)-4-(2-methylpropyl)-5-(1-pyrrolidinylmethyl)-6-(trifluoromethyl)-, methyl ester.

The method of Example 27 was followed using 9.7 mmol of the Compound of Example 3 and 0.15 mol of pyrrolidine in THF stirred at room temperature for 2 hours. $n_D^{25}$ 1.4685.

EXAMPLE 49

Preparation of 3-Pyridinecarboxylic acid, 2-(difluoromethyl)-5-[(ethylmethylamino)methyl]-4-(2-methylpropyl)-6-(trifluoromethyl)-, methyl ester.

The method of Example 27 was followed using 8.3 of the Compound of Example 3 and 17 mmol of N-thylmethylamine in ether stirred at room temperature for 18 hours. $n_D^{25}$ 1.4569.

EXAMPLE 50

Preparation of 3-Pyridinecarboxylic acid, 2-(difluoromethyl)-5-[(dimethylamino)methyl]-4-(2-methylpropyl)-6-(trifluoromethyl)-, methyl ester.

The method of Example 27 was followed using 19 mmol of the Compound of Example 3 and a solution of 0.21 mol of 26% aqueous dimethylamine in THF stirred at room temperature for 21 hours. $n_D^{25}$ 1.4560.

EXAMPLE 51

Preparation of 3-Pyridinecarboxylic acid, 4-(cyclopropylmethyl)-2-(difluoromethyl)-5-[(ethylthio)methyl]-6-(trifluoromethyl)-, methyl ester.

The method of Example 27 was followed using 10 mmol of the Compound of Example 4 and a solution prepared from 24 mmol of sodium metal and 48 mmol of ethanethiol in 40 mL of methanol stirred at room temperature for 2 hours. $n_D^{25}$ 1.4907.

EXAMPLE 52

Preparation of 3-Pyridinecarbothioic acid, 4-(cyclopropylmethyl)-2-(difluoromethyl)-5-[(methylthio)methyl]-6-(trifluoromethyl)-, methyl ester The method of Example 27 was followed using 10 mmol of the Compound of Example 4 and a solution of 40 mmol of sodium methanethiolate in 20 mL of methanol stirred at room temperature for 6 hours. m p. 109°-110° C.

EXAMPLE 53

Preparation of 3-Pyridinecarboxylic acid, 4-(cyclopropylmethyl)-2-(difluoromethyl)-5-[1-(methylthio)ethyl]-6-(trifluoromethyl)-, methyl ester.

The method of Example 27 was followed using 8.1 mmol of the Compound of Example 26 and 8.6 mmol of sodium methanethiolate in 40 mL of methanol refluxed for 2 hours. $n_D^{25}$ 1.4927.

EXAMPLE 54

Preparation of 3-Pyridinecarboxylic acid, 4-(cyclopropylmethyl)-2-(difluoromethyl)-5-[(methylthio)methyl]-6-(trifluoromethyl)-, methyl ester.

The method of Example 27 was followed using 8.1 mmol of the Compound of Example 4 and a solution of 8.6 mmol of sodium methanethiolate in 40 mL of methanol refluxed for 2 hours. $n_D^{25}$ 1.4940.

EXAMPLE 55

Preparation of 3-Pyridinecarboxylic acid, 4-(cyclopropylmethyl)-2-(difluoromethyl)-5-[1-(dimethylamino)ethyl] -6-(trifluoromethyl)-, methyl ester.

The title compound was prepared by reaction of the Compound of Example 26 and dimethylamine following the method of Example 27. $n_D^{25}$ 1.4724.

EXAMPLE 56

Preparation of 3-Pyridinecarboxylic acid, 4-(cyclopropylmethyl)-2-(difluoromethyl)-5-[1-(ethylthio)ethyl]-6-(trifluoromethyl)-, methyl ester.

The title compound was prepared by reaction of the Compound of Example 26 and sodium ethanethiolate following the method of Example 27. $n_D^{25}$ 1.4889.

EXAMPLE 57

Preparation of 3-Pyridinecarboxylic acid, 4-(cyclopropylmethyl)-2-(difluoromethyl)-5-[1-(methylthio)propyl]-6-(trifluoromethyl)-, methyl ester.

The title compound was prepared by reaction of the Compound of Example 77 and sodium methanethiolate following the method of Example 27. $n_D^{25}$ 1.4914.

EXAMPLE 58

Preparation of 3-Pyridinecarboxylic acid, 4-(cyclopropylmethyl)-2-(difluoromethyl)-5-[1-(1H-pyrazol-1-yl)ethyl]-6-(trifluoromethyl)-, methyl ester.

The title compound was prepared by reaction of the Compound of Example 26 and pyrazole sodium salt following the method of Example 27. $n_D^{25}$ 1.4979.

EXAMPLE 59

Preparation of 3-Pyridinecarboxylic acid, 4-(cyclopropylmethyl)-2-(difluoromethyl)-5-(methoxymethyl)-6-(trifluoromethyl)-, methyl ester.

To a slurry of 0.01 mol sodium hydride in THF was added a solution of 0.01 mol of Compound A4 and 0.024 mol methyl iodide in THF. The reaction mixture was stirred for 2 hours, quenched with 10% hydrochloric acid, and extracted with methylene chloride. The methylene chloride layer was dried over magnesium sulfate and concentrated in vacuo. The residue was purified by silica gel column chromatography to give the pure product as a yellow oil.

EXAMPLE 60

Preparation of 3-Pyridinecarboxylic acid, 4-(cyclopropylmethyl)-2-(difluoromethyl)-5-(2-propenyloxy)-6-(trifluoromethyl)-, methyl ester.

To a slurry of 0.01 mol sodium hydride in THF was added a solution of 0.01 mol of Compound A4 and 0.012 mol allyl bromide in THF. The reaction mixture was stirred for 2 hours, quenched with 10% hydrochloric acid, and extracted with methylene chloride. The methylene chloride layer was dried over magnesium sulfate and concentrated in vacuo. The residue was purified by silica gel column chromatography to give the pure product as a yellow oil.

EXAMPLE 61

Preparation of 3-Pyridinecarboxylic acid, 4-(cyclopropylmethyl)-2-(difluoromethyl)-5-(1-methoxyethyl)-6-(trifluoromethyl)-, methyl ester.

To a mixture of 1 equivalent of the Compound of Example 25 and 10 equivalents of methyl iodide, 0.1-0.3 g of the phase transfer catalyst (PTC) benzyltriethylammonium chloride in methylene chloride was added 50% sodium hydroxide in equal volume to the methylene chloride. The reaction mixture was stirred for 2 hours and was then extracted into ether. The organic phase was washed with brine, dried over magnesium sulfate, and concentrated in vacuo. The residue was kugelrohr distilled to give the pure product or the distillate further purified by HPLC to provide the pure product. $n_D^{25}$ 1.4656.

EXAMPLE 62

Preparation of 3-Pyridinecarboxylic acid, 4-(cyclopropylmethyl)-2-(difluoromethyl)-5-(1- 1-methoxypropyl)-6-(trifluoromethyl)-, methyl ester.

The method of Example 61 was followed using the Compound of Example 24. $n_D^{25}$ 1.4653.

EXAMPLE 63

Preparation of 3-Pyridinecarboxylic acid, 4-(cyclopropylmethyl)-2-(difluoromethyl)-5-(1-ethoxyethyl)-6-(trifluoromethyl)-, methyl ester.

The method of Example 61 was followed using ethyl iodide instead of methyl iodide. $n_D^{25}$ 1.4615.

EXAMPLE 64

Preparation of 3-Pyridinecarboxylic acid, 4-(cyclopropylmethyl)-2-(difluoromethyl)-5-(1-methoxy-2-propenyl)-6-(trifluoromethyl)-, methyl ester.

The method of Example 61 was followed using the Compound of Example 22. $n_D^{25}$ 1.4723.

EXAMPLE 65

Preparation of 3-Pyridinecarboxylic acid, 4-(cyclopropylmethyl)-2-(difluoromethyl)-5-(1-ethoxy-2-propenyl)-6-(trifluoromethyl)-, methyl ester.

The method of Example 64 was followed using ethyl iodide instead of methyl iodide. $n_D^{25}$ 1.4683.

EXAMPLE 66

Preparation of 3-Pyridinecarboxylic acid, 4-(cyclopropylmethyl)-2-(difluoromethyl)-5-(1-methoxy-3-butenyl)-6-(trifluoromethyl)-, methyl ester.

The method of Example 61 was followed using the Compound of Example 23. $n_D^{25}$ 1.4748.

EXAMPLE 67

Preparation of 3-Pyridinecarboxylic acid, 2-(difluoromethyl)-5-(1-methoxypropyl)-4-(2-methylpropyl)-6-(trifluoromethyl)-, methyl ester.

The method of Example 61 was followed using the Compound of Example 19 and Aliquat 336 as the PTC. m.p. 60°-62° C.

EXAMPLE 68

Preparation of 3-Pyridinecarboxylic acid, 2-(difluoromethyl)-5-(1-methoxy-3-butenyl)-4-(2-methylpropyl)-6-(trifluoromethyl)-, methyl ester.

The method of Example 61 was followed using the Compound of Example 21 and Aliquat 336 as the pTC. $n_D^{25}$ 1.4610.

EXAMPLE 69

Preparation of 3-Pyridinecarboxylic acid, 2-(difluoromethyl)-4-(2-methylpropyl)-5-[1-(2-propynyloxy)ethyl]-6-(trifluoromethyl)-, methyl ester.

The method of Example 61 was followed using the Compound of Example 20 and propargyl bromide instead of methyl iodide. Aliquat 336 Was the PTC. $n_D^{25}$ 1.4656.

EXAMPLE 70

Preparation of 3-Pyridinecarboxylic acid, 2-(difluoromethyl)-5-(1-methoxyethyl)-4-(2-methylpropyl)-6-(trifluoromethyl)-, methyl ester.

The method of Example 61 was followed using the Compound of Example 20 and Aliquat 336 as the PTC. $n_D^{25}$ 1.4539.

EXAMPLE 71

Preparation of 3-Pyridinecarboxylic acid, 2-(difluoromethyl)-4-(2-methylpropyl)-5-[1-(2-propenyloxy)ethyl]-6-(trifluoromethyl)-, methyl ester.

The method of Example 61 was followed using the Compound of Example 20 and allyl bromide. Aliquat 336 was the PTC. $n_D^{25}$ 1.4597.

EXAMPLE 72

Preparation of 3-Pyridinecarboxylic acid, 2-(difluoromethyl)-4-(2-methylpropyl)-5-[1-(2-propenyloxy)3-butenyl]-6-(trifluoromethyl)-, methyl ester.

The method of Example 61 was followed using the Compound of Example 21 and allyl bromide. Aliquat 336 was the PTC. $n_D^{25}$ 1.4657.

EXAMPLE 73

Preparation of 3-Pyridinecarboxylic acid, 2-(difluoromethyl)-4-(2-methylpropyl)-5-[1-(2-propenyloxy)propyl]-6-(trifluoromethyl)-, methyl ester.

The method of Example 61 was followed using the Compound of Example 19 and allyl bromide. Aliquat 336 was the PTC. $n_D^{25}$ 1.4657.

EXAMPLE 74

Preparation of 3-Pyridinecarboxylic acid, 2-(difluoromethyl)-5-(ethoxymethyl)-4-(2-methylpropyl)-6-(trifluoromethyl)-, methyl ester.

The method of Example 61 was followed using the Compound of Example A3 and ethyl iodide. Aliquat 336 was the PTC. $n_D^{25}$ 1.4491.

EXAMPLE 75

Preparation of 3-Pyridinecarboxylic acid, 2-(difluoromethyl)-4-(2-methylpropyl)-5-[(2-propynyloxy)-methyl]-6-(trifluoromethyl)-, methyl ester.

The method of Example 61 was followed using the Compound of Example A3 and propargyl bromide. Aliquat 336 was the PTC. $n_D^{25}$ 1.4635.

EXAMPLE 76

Preparation of 3-Pyridinecarboxylic acid, 4-(cyclopropylmethyl)-2-(difluoromethyl)-5-(1-methoxybutyl)-6-(trifluoromethyl)-, methyl ester.

The compound of Example B2 was reacted with propyl magnesium chloride to produce 3-pyridinecarboxylic acid, 4-(cyclopropylmethyl)-2-(difluoromethyl)-5-(1-hydroxybutyl)-6-(trifluoromethyl)-, methyl ester. This pyridine butanol was reacted with methyl iodide using the method of Example 61. $n_D^{25}$ 1.4651.

EXAMPLE 77

Preparation of 3-Pyridinecarboxylic Acid, 5-(1-chloropropyl)-4-(cyclopropylmethyl)-2-(difluoromethyl)-6-(trifluoromethyl)-, methyl ester.

This product was prepared from the Compound of Example 24 by the procedure of Example 26 as a colorless oil, $n_D^{25}$ 1.4742.

EXAMPLE 78

Preparation of 3-Pyridinecarboxylic Acid, 5-(1-cyanopropyl)-4-(cyclopropylmethyl)-2-(difluoromethyl)-6-(trifluoromethyl)-, methyl ester.

The title product was prepared by reaction of the Compound of Example 77 using the method of Example 5. It was purified as a colorless oil. $n_D^{25}$ 1.4723.

EXAMPLE 79

Preparation of 3-Pyridinecarboxylic acid, 5-(2-amino-2-thioxoethyl)-2-(difluoromethyl)-4-(2-methylpropyl)-6-(trifluoromethyl)-, methyl ester.

Through a solution of 1 equivalent of the Compound of Example 7 and 0.07 equivalent of diethylamine in dry DMF was passed excess hydrogen sulfide gas. The reaction mixture was poured into saturated sodium bicarbonate and extracted with ether. The ether layer was dried over magnesium sulfate and concentrated in vacuo. The residual solid was recrystallized from hexane/ethyl acetate as a yellow solid. m.p. 162°-164° C.

Using the method of Example 79 the following compounds were made from the starting materials shown.

| Ex. No. | Strtg Mtrl. | Name | Phys. Prop. |
|---|---|---|---|
| 80 | Ex. 8 | 3-Pyridinecarboxylic acid, 5-(2-amino-2-thioxoethyl)-4-(cyclopropylmethyl)-2-(difluoromethyl)-6-(trifluoromethyl)-, methyl ester. | m.p. 173-173.5° C. |
| 81 | Ex. 15 | 3-Pyridinecarboxylic acid, 5-(2-amino-1-methyl-2-thioxoethyl)-4-(cyclopropylmethyl)-2-(difluoromethyl)-6-(trifluoromethyl)-, methyl ester. | m.p. 139.5-140° C. |
| 82 | Ex. 16 | 3-Pyridinecarboxylic acid, 5-[1-(aminothioxomethyl)-3-butenyl]-4-(cyclopropylmethyl)-2- | m.p. 95.5-96.5° C. |

-continued

| Ex. No. | Strtg Mtrl. | Name | Phys. Prop. |
|---|---|---|---|
| | | (difluoromethyl)-6-(trifluoromethyl)-, methyl ester. | |

EXAMPLES 83 AND 84

Preparation of 3-Pyridinecarboxylic acid, 2-(difluoromethyl)-5-[2-(methylimino)-2-(methylthio)ethyl]-4-(2-methylpropyl)-6-(trifluoromethyl)-, methyl ester (Ex. 83), and 3-Pyridinecarboxylic acid, 2-(difluoromethyl)-5-[2-imino-2-(methylthio)ethyl]-4-(2-methylpropyl)-6-(trifluoromethyl)-, methyl ester (Ex. 84).

A mixture of 3.0 g (7.9 mmol) of the Compound of Example 79, 1.1 g (7.9 mmol) potassium carbonate, and 7.7 g (53 mmol) methyl iodide in 20 mL of DMF was stirred for 6 hours and poured into water. The resulting mixture was extracted with ether and the ether layer was washed successively with water and saturated sodium bicarbonate, dried over magnesium sulfate, and concentrated in vacuo. The residue was purified by HPLC followed by radial thin layer chromatography to give product of Example 83 in the first fraction as an oil, $n_D^{25}$ 1.4936. The later fraction yielded Compound 84 as an oil, $n_D^{25}$ 1.4937.

EXAMPLE 85

Preparation of 3-Pyridinecarboxylic acid, 2-(difluoromethyl)-5-(4,5-dihydro-2-thiazolyl)methyl-4-(2-methylpropyl)-6-(trifluoromethyl)-, methyl ester.

A mixture of 1 equivalent of the Compound of Example 79, 3 equivalents of 2,6-lutidine, 6.6 equivalents of 1,2-dibromoethane and 100 mL of toluene was held at reflux for 3 days. The reaction mixture was partitioned between ether and 3 N hydrochloric acid. The ether layer was washed with brine, dried over magnesium sulfate, and filtered through silica gel. The filtrate was evaporated in vacuo and the residue was dissolved in mL methanol then treated with 5 g of 25% sodium methoxide in methanol. The mixture was held at reflux for 5 min, cooled and partitioned between ether and 3 N hydrochloric acid. The organic layer was washed with brine, dried over magnesium sulfate, and filtered through silica gel. The filtrate was concentrated in vacuo and the residue was purified by HPLC (15-25% ethyl acetate/hexane) to give the pure product. $n_D^{25}$ 1.4979.

Using the method of Example 85, the following compounds were made from the starting materials shown.

| Ex. No. | Strtg Mtrl. | Name | Phys. Prop. |
|---|---|---|---|
| 86 | Ex. 80 | 3-Pyridinecarboxylic acid, 4-(cyclopropylmethyl)-2-(difluoromethyl)-5-[(4,5-dihydro-2-thiazolyl)methyl]-6-(trifluoromethyl)-, methyl ester. | $n_D^{25}$ 1.5116 |
| 87 | Ex. 81 | 3-Pyridinecarboxylic acid, 4-(cyclopropylmethyl)-2-(difluoromethyl)-5-[1-(4,5-dihydro-2-thiazolyl)ethyl]-6-(trifluoromethyl)-, methyl ester. | $n_D^{25}$ 1.5114 |
| 88 | Ex. 82 | 3-Pyridinecarboxylic acid, 4-(cyclopropylmethyl)-2-(difluoromethyl)-5-[1-(4,5-dihydro-2-thiazolyl)-3-butenyl]-6-(trifluoromethyl)-, methyl ester. | $n_D^{25}$ 1.5132 |

EXAMPLE 89

Preparation of 3-Pyridinecarboxylic acid, 2-(difluoromethyl)-4-(2-methylpropyl)-5-(methylsulfinyl)-methyl]-6-(trifluoromethyl)-, methyl ester.

To a solution of 9.5 g (25 mmol) of the Compound of Example 27 in 25 mL of methylene chloride was added 4.5 g (25 mmol) of 85% MCPBA. The reaction mixture was stirred for 1 hour and filtered. The filtrate was washed with 10% sodium hydroxide, dried over magnesium sulfate, and concentrated in vacuo. The residue was purified by HPLC to give 4.9 g of the desired product. m.p. 95°-96° C.

EXAMPLE 90

Preparation of 3-Pyridinecarboxylic acid, 2-(difluoromethyl)-4-(2-methylpropyl)-5-[(methylsulfonyl)-methyl]-6-(trifluoromethyl)-, methyl ester.

To a solution of 1 equivalent of the pyridylmethyl alkyl sulfide produced in Example 27 in methylene chloride was added 2 equivalents of MCPBA. The reaction mixture was stirred for i hour and worked up as in example 89 to provide the desired product as a white solid. m.p. 121°-122° C.

EXAMPLE 91

Preparation of 3-Pyridinecarboxylic acid, 6-(difluoromethyl)-4-(2-methylpropyl)-5-[(methylsulfonyl)-methyl]-2-(trifluoromethyl)-, methyl ester.

To a solution of 1 equivalent of the pyridylmethyl alkyl sulfide produced in Example 30 in methylene chloride was added 2 equivalents of MCPBA. The reaction mixture was stirred for 1 hour and worked up as in example 89 to provide the desired product as a white solid. m.p. 147°-148.5° C.

EXAMPLE 92

Preparation of 3-Pyridinecarboxylic acid, 4-(cyclopropylmethyl)-2-(difluoromethyl)-5-[(methylsulfonyl-)ethyl]-6-(trifluoromethyl)-, methyl ester.

One equivalent of the Compound of Example 54 was oxidized with 2 equivalents of MCPBA as described in Example 90 to give 3-pyridinecarboxylic acid, 4-(cyclopropylmethyl)-2-(difluoromethyl)-5-[(methylsulfonyl-)ethyl]-6-(trifluoromethyl)-, methyl ester, as a white solid (m.p. 115.5°-116.5° C.). This solid was alkylated with methyl iodide as described in Example 15 to give the title compound as white crystals after recrystallization from ethyl acetate/hexane. m.p. 117°-117.5° C.

EXAMPLE 93

Preparation of 3-Pyridinecarboxylic acid, 4-(cyclopropylmethyl)-2-(difluoromethyl)-5-[1-(methylsulfonyl)-3-butenyl]-6-(trifluoromethyl)-, methyl ester.

The title product was obtained by reaction of 3-pyridinecarboxylic acid, 4-(cyclopropylmethyl)-2-(difluoromethyl)-5-[(methylsulfonyl)methyl]-6-(trifluoromethyl)-, methyl ester, prepared as in Example 92, with allyl bromide using the method of Example 16 and purified by HPLC (20% ethyl acetate/hexane) to yield a yellow oil. $n_D^{25}$ 1.4939.

EXAMPLE 94

Preparation of 3-Pyridineacetic acid, 2-(difluoromethyl)-5-(ethoxycarbonyl)-4-ethyl-6-(trifluoromethyl)-, ethyl ester.

A mixture of 0.01 mol of the Compound of Example 5, 3 mL conc. sulfuric acid, and 30 mL of ethanol was held at reflux for 1-5 days. The mixture was cooled and partitioned between ether and water. The ether layer was washed with brine, dried over magnesium sulfate, and concentrated in vacuo. The residue was purified by HPLC to give the pure product. $n_D^{25}$ 1.4544.

EXAMPLE 95

Preparation of 3-Pyridineacetic acid, 2-(difluoromethyl)-4-(2-methylpropyl)-5-(methoxycarbonyl)-6-(trifluoromethyl)-, methyl ester.

The method of Example 94 was followed using the Compound of Example 7 and methanol to yield the desired product as a colorless oil. b.p. 125° C. (0.2 torr).

EXAMPLE 96

Preparation of 3-Pyridineacetic acid, 4-(cyclopropylmethyl)-6-(difluoromethyl)-5-(methoxycarbonyl)-2-(trifluoromethyl)-, methyl ester.

The method of Example 94 was followed using the Compound of Example 8 and methanol to yield the desired product as a colorless oil. $n_D^{25}$ 1.4694.

EXAMPLE 97

Preparation of 3-Pyridineacetic acid, 4-(cyclopropylmethyl)-6-(difluoromethyl)-5-(methoxycarbonyl)-α-methyl-2-(trifluoromethyl)-, methyl ester.

The method of Example 9 was followed using the Compound of Example 96 and methyl iodide to yield the desired product as a colorless oil. $n_D^{25}$ 1.4698.

EXAMPLE 98

Preparation of 3-Pyridineacetic acid, 4-(cyclopropylmethyl)-6-(difluoromethyl)-5-(methoxycarbonyl)-α-(2-propenyl)-2-(trifluoromethyl)-, methyl ester.

The method of Example 9 was followed using the Compound of Example 96 and allyl bromide to yield the desired product as a colorless oil. $n_D^{25}$ 1.4698.

EXAMPLE 99

Preparation of 3-Pyridinecarboxylic acid, 5-[[(chloroacetyl)oxy]methyl]-4-(cyclopropylmethyl)-2-(difluoromethyl)-6-(trifluoromethyl)-, methyl ester.

To a 0° C. solution of 0.01 mol of the Compound of Example A4 and 0.01 mol triethylamine in 25 mL of methylene chloride was added 0.01 mol of chloroacetyl chloride over 20 to 30 min. The reaction mixture was stirred at 0° C. for 30 min, quenched with 200 mL of 5% hydrochloric acid, and extracted with methylene chloride. The methylene chloride layer was washed with water, dried over magnesium sulfate, and concentrated in vacuo. The residue was purified by silica gel column chromatography (10% ethyl acetate/hexane) to give the desired product as a pale yellow oil.

EXAMPLE 100

Preparation of 3-Pyridinecarboxylic acid, 4-(cyclopropylmethyl)-5-[[(dichloroacetyl)oxy]methyl]-2-(difluoromethyl)-6-(trifluoromethyl)-, methyl ester.

The method of Example 99 was followed except that dichloroacetyl chloride was used to yield the title compound as an amber oil.

EXAMPLE 101

Preparation of 3-Pyridinecarboxylic acid, 5-[(acetyloxy)methyl]-4-(cyclopropylmethyl)-2-(difluoromethyl)-6-(trifluoromethyl)-, methyl ester.

The method of Example 99 was followed except that acetyl chloride was used to yield the title compound as a yellow oil. $n_D^{25}$ 4689.

EXAMPLE 102

Preparation of 3-Pyridinecarboxylic acid, 4-(cyclopropylmethyl)-2-(difluoromethyl)-5-[[(trifluoroacetyl)oxy]methyl]-6-(trifluoromethyl)-, methyl ester.

The method of Example 99 was followed except that trifluoroacetic anhydride was used, omitting the triethylamine, to yield the title compound as a pale yellow oil. $n_D^{25}$ 1.4583.

EXAMPLE 103

Preparation of 3-Pyridinecarboxylic acid, 5-(2-bromoethyl)-6-(difluoromethyl)-4-(2-methylpropyl)-2-(trifluoromethyl)-, methyl ester.

3-Pyridinecarboxylic acid, 6-(difluoromethyl)-5-(1-hydroxyethyl)-4-(2-methylpropyl)-2-(trifluoromethyl)-, methyl ester, (prepared from Compound B3 and methyl magnesium bromide according to the procedure of Example 19) (4.5 g), and 100 mL of 50% sulfuric acid were heated at 145° C. for 4 hours, cooled, and poured onto ice. The mixture was extracted with ether. The ether layer was dried over magnesium sulfate, and concentrated in vacuo. The residue was purified by radial thin layer chromatography to give 3-pyridinecarboxylic acid, 6-(difluoromethyl)-5-ethenyl- 4-(2-methylpropyl)-2-(trifluoromethyl)-, methyl ester, as a colorless oil. Through a mixture of this oil (0.015 mol), 0.41 g benzoylperoxide and 60 mL hexane, was passed gaseous hydrogen bromide for 1 hour. The mixture was washed with saturated sodium bicarbonate, dried over magnesium sulfate, and concentrated. The residue was purified by radial thin layer chromatography (15% methylene chloride/cyclohexane) followed by kugelrohr distillation to yield the desired product, 5.6 g. m.p. 64°-66° C.

EXAMPLE 104

Preparation of 3-Pyridinecarboxylic acid, 6-(difluoromethyl)-4-(2-methylpropyl)-5-[2-(methylthio)ethyl]-2-(trifluoromethyl)-, methyl ester.

A mixture of 22 mmol of the compound of Example 103, 0.23 g sodium methanethiolate, and 25 mL THF was stirred at room temperature overnight. The mixture was diluted with ether and washed successively with diluted hydrochloric acid and brine, dried over magnesium sulfate, and concentrated in vacuo. Kugelrohr distillation yielded the desired product as a solid. m.p. 47°-49° C.

EXAMPLE 105

Preparation of 3-Pyridinecarboxylic acid, 5-(1,2-dibromoethyl)-6-(difluoromethyl)-4-(2-methylpropyl)-2-(trifluoromethyl)-, methyl ester.

A mixture of 2.3 g of 3-pyridinecarboxylic Acid, 6-(difluoromethyl)-5-ethenyl-4-(2-methylpropyl)-2-(trifluoromethyl)-, methyl ester, the intermediate compound prepared in Example 103, 0.7 mL bromine, and 20 mL carbon tetrachloride, was stirred for 2 hours and concentrated in vacuo. The residual solid was recrysatllized from hexane to yield 1.0 g of the desired product as white crystals. m.p. 75°-77° C.

EXAMPLE 106

Preparation of 3-Pyridinecarboxylic Acid, 5-(2-bromoethenyl)-6-(difluoromethyl)-4-(2-methylpropyl)-2-(trifluoromethyl)-, methyl ester.

A mixture of 42 mmol of the Compound of Example 105, 25 mL methanol, and 1.1 mL of 25% sodium methoxide, was stirred at room temperature for 30 min, poured into diluted hydrochloric acid and extracted with ether. The ether layer was dried over magnesium sulfate, and concentrated. The residue was kugelrohr distilled (90° C.) at reduced pressure to give a colorless oil with a 0% yield.

EXAMPLE 107

Preparation of 3-Pyridinecarboxylic acid, 6-(difluoromethyl)-5-(2-ethoxyethenyl)-4-(2-methylpropyl)-2-(trifluoromethyl)-, methyl ester.

A mixture of the Compound of Example 105 (37 mmol), 25 mL ethanol, and 0.61 g potassium hydroxide was held at reflux for 30 min and worked up as in Example 106 to give a colorless oil.

EXAMPLE 108

Preparation of 3-Pyridinecarboxylic acid, 6-(difluoromethyl)-5-(2-methoxyethenyl)-4-(2-methylpropyl)-2-(trifluoromethyl)-, methyl ester.

A mixture of 32 mmol of the Compound of Example 105, 20 mL methanol and 1.45 mL of 25% sodium methoxide, was held at reflux for 2 hours, cooled and worked up as in Example 106 to give a yellow oil.

EXAMPLE 109

Preparation of 3-Pyridinecarboxylic acid, 6-(difluoromethyl)-4-(2-methylpropyl)-5-[2-(methylthio)ethenyl]-2-(trifluoromethyl)-, methyl ester.

A mixture of 0.8 g of the Compound of Example 105 in THF was reacted with 0.48 g of sodium methanethiolate at room temperature for 3.5 hours and worked up as in Example 106 to give 0.8 g of a pale yellow oil.

EXAMPLE 110

Preparation of 3-Pyridinecarboxylic acid, 5-(1,2-dibromoethyl)-2-(difluoromethyl)-4-(2-methylpropyl)-6-(trifluoromethyl)-, methyl ester.

3-Pyridinecarboxylic Acid, 2-(difluoromethyl)-5-ethenyl-4-(2-methylpropyl)-6-(trifluoromethyl)-, methyl ester, prepared by dehydration of the product of Example 20 with 50% sulfuric acid according to the procedure of Example 103, was reacted with bromine as in Example 105 to give a pale yellow oil.

EXAMPLE 111

Preparation of 3-Pyridinecarboxylic acid, 5-(2-bromoethenyl)-2-(difluoromethyl)-4-(2-methylpropyl)-6-(trifluoromethyl)-, methyl ester.

The compound of Example 110 was reacted as in Example 106 to give a pale yellow oil.

EXAMPLE 112

Preparation of 3-Pyridinecarboxylic acid, 2-(difluoromethyl)-5-(2-methoxyethenyl)-4-(2-methylpropyl)-6-(trifluoromethyl)-, methyl ester.

The Compound of Example 110 was reacted as in Example 108 to give a brown oil.

EXAMPLE 113

Preparation of 3-Pyridinecarboxylic acid, 2-(difluoromethyl)-4-(2-methylpropyl)-5-[2-(methylthio)ethenyl]-6-(trifluoromethyl)-, methyl ester.

The Compound of Example 110 was reacted as in Example 109 to give a colorless oil.

EXAMPLE 114

Preparation of 3-Pyridinecarboxylic acid, 6-(difluoromethyl)-5-(2-methoxyethyl)-4-(2-methylpropyl)-2-(trifluoromethyl)-, methyl ester.

A mixture of 1.2 g of the Compound of Example 108, one spatula full of 5% palladium on carbon (50% water) and 30 mL ethanol, was hydrogenated in a Parr hydrogenation apparatus with 50 psi of hydrogen for 1.5 hours and filtered. The filtrate was concentrated in vacuo and the residue was kugelrohr distilled (100° C.) at reduced pressure to give a colorless oil.

EXAMPLE 115

Preparation of 3-Pyridinecarboxylic acid, 2-(difluoromethyl)-5-(2-methoxyethyl)-4-(2-methylpropyl)-6-(trifluoromethyl)-, methyl ester.

The Compound of Example 112 was reacted as in Example 114 to give a colorless oil.

EXAMPLE 116

Preparation of 3-Pyridinecarboxylic acid, 6-(difluoromethyl)-5-(2-dimethylaminoethyl)-4-(2-methylpropyl)-2-(trifluoromethyl)-, methyl ester.

A mixture of 27 mmol of the Compound of Example 105 and 15 mL ethanol was combined with 0.38 g (2 equivalents) of potassium hydroxide causing a color change to yellow and formation of a solid. After 1.5 hours, the reaction mixture was triturated with diluted hydrochloric acid and extracted with ether. The ether layer was dried over magnesium sulfate, and concentrated in vacuo. The residue was purified by radial thin layer chromatography (10% methylene chloride/cyclohexane) to give pure 3-pyridine-carboxylic acid, 6-(difluoromethyl)-5-(ethynyl)-4-(2-methylpropyl)-2-(trifluoromethyl)-, methyl ester, as an oil. A mixture of this oil (4 mmol), 20 mL THF, and 1.5 mL of 26% aqueous dimethylamine was let stand at room temperature overnight. The mixture was diluted with ether and washed with brine. The ether layer was dried over magnesium sulfate, and concentrated. The residue was dissolved in 50 mL ethanol and treated with 0.5 g 5% palladium on carbon (50% water). The mixture was hydrogenated and worked up as in Example 114 to give 1.4 g of yellow oil which was purified by radial thin layer chromatography (30% ethyl acetate/cyclohexane) followed by kugelrohr distillation (110° C.) at reduced pressure to give 1.1 g of a pale yellow oil.

EXAMPLE 117

Preparation of 3-Pyridinecarboxylic acid, 2-(difluoromethyl)-5-[2-(dimethyamino)ethenyl)-4-(2-methylpropyl)-6-(trifluoromethyl)-, methyl ester.

To a −78° C. solution of 11.2 mmol of the Compound of Example 111 in 50 mL dry THF was added 25 mL of 1 M lithium bis(trimethylsilyl)amide over 5 min. The reaction mixture was stirred for 15 min and poured into ice water containing conc. HCl. The mixture was extracted with ether. The ether layer was dried over magnesium sulfate and concentrated in vacuo. The residue was kugelrohr distilled (90° C.) at reduced pressure to give 3-pyridinecarboxylic acid, 2-(difluoromethyl)-5-(ethynyl)-4-(2-methylpropyl)-6-(trifluoromethyl)-, methyl ester, as a colorless oil. A mixture of this oil (4.7 mmol), 5 mL dimethylamine and 25 mL THF, was stirred for 2.5 hours, poured into brine and extracted with ether. The ether layer was dried over magnesium sulfate and concentrated in vacuo. The residue was kugelrohr distilled (110° C.) at reduced pressure to give 1.6 g of a yellow oil.

EXAMPLE 118

Preparation of 3-Pyridinecarboxylic acid, 2-(difluoromethyl)-5-[2-(dimethyamino)ethyl)-4-(2-methylpropyl)-6-(trifluoromethyl)-, methyl ester.

The Compound of Example 117 was hydrogenated as in Example 116 to give a pale yellow oil.

EXAMPLE 119

Preparation of 3-Pyridinecarboxylic acid, 5-(2-cyano-3-methoxy-3-oxo-1-propenyl)-4-(cyclopropylmethyl)-2-(difluoromethyl)-6-(trifluoromethyl)-, methyl ester.

A mixture of 0.01 mol of Compound B20.01, mol of methyl cyanoacetate, 0.05 g piperidine, and 50 mL toluene was held at reflux for 3 hours while water was removed by a Dean-Stark trap. The reaction mixture was concentrated in vacuo and the residue was kugelrohr distilled at 0.02 torr (110°-130° C.). The distillate was purified by silica gel column chromatography to give desired compound as a yellow oil. b.p. 125°-130° C. (0.02 torr).

EXAMPLE 120

Preparation of 3-Pyridinecarboxylic acid, 4-(cyclopropylmethyl)-5-(2,2-dicyanoethenyl)-2-(difluoromethyl)-6-(trifluoromethyl)-, methyl ester.

The method of Example 119 was followed substituting malononitrile for cyanoacetate to yield the desired compound as an orange oil. b.p. 117°-120° C. (0.02 torr).

EXAMPLE 121

Preparation of 3-Pyridinecarboxylic acid, 5-(2-cyano-3-methoxy-3-oxo-1-propenyl)-4-(cyclopropylmethyl)-2-(fluoromethyl)-6-(trifluoromethyl)-, methyl ester.

To a suspension of 2.6 g (12.7 mmol) of cuprous bromide-dimethyl sulfide complex in 75 mL THF at −78° C. was added dropwise 18 mL (25 mmol) of 1.4 M methyllithium in ether. The reaction mixture was stirred at −78° C. for 20 min and was then allowed to warm to 0° C. The mixture was cooled back to −78° C. and to the mixture was added a solution of 5.0 g (12 mmol) of the Compound of Example 119 in 50 mL THF. The dark brown solution was stirred at −78° C. for 5 min and was allowed to warm to 0° C. The mixture was quenched with 1.2 N hydrochloric acid and was extracted into ether. The ether layer was washed with brine, dried over magnesium sulfate, and concentrated in vacuo. The residue was kugelrohr distilled to give 2.1 g (44%) of the desired compound as a light yellow oil. $n_D^{25}$ 1.4995.

EXAMPLE 122

Preparation of 3-Pyridinecarboxylic acid, 2-(difluoromethyl)-5-(3-ethoxy-3-oxo-1-propenyl)-4-(2-methylpropyl)-6-(trifluoromethyl)-, methyl ester.

A mixture of 1 equivalent of the pyridinecarboxaldehyde B1 in methylene chloride and 1 equivalent of (carbethoxymethylene)triphenylphosphorane was reacted at room temperature. The reaction mixture was concentrated in vacuo and the residue was stirred with petroleum ether and filtered. The filtrate was concentrated and the residue was purified by silica gel column chromatography or radial thin layer chromatography followed by kugelrohr distillation to give the title compound as a colorless oil.

EXAMPLE 123

Preparation of 3-Pyridinecarboxylic acid, 2-(difluoromethyl)-5-(3-methoxy-3-oxo-1-propenyl)-4-(2-methylpropyl)-6-(trifluoromethyl)-, methyl ester.

The method of Example 122, using (carbmethoxymethylene)triphenylphosphorane as the Wittig reagent, was followed. The title compound was isolated as a white solid. m.p. 62°-65° C.

EXAMPLE 124

Preparation of 3-pyridinecarboxylic acid, 2-(difluoromethyl)-5-(3-ethoxy-2-methyl-3-oxo-1-propenyl)-4-(2-methylpropyl)-6-(trifluoromethyl)-, methyl ester.

A mixture of 1 equivalent of the pyridinecarboxaldehyde B1 in methylene chloride and 1 equivalent of (carbethoxyethylidine)triphenylphosphorane was reacted at reflux temperature. The reaction mixture was concentrated in vacuo and the residue was stirred with petroleum ether and filtered. The filtrate was concentrated and the residue was purified by silica gel column chromatography or radial thin layer chromatography followed by kugelrohr distillation to give the title compound as a yellow oil.

EXAMPLE 125

Preparation of 3-Pyridinecarboxylic acid, 5-(2-cyanoethyl)-4-(cyclopropylmethyl)-2-(difluoromethyl)-6-(trifluoromethyl)-, methyl ester.

A mixture of 1 equivalent of the pyridinecarboxaldehyde, Compound B2, in THF and 1 equivalent of the Wittig reagent (prepared in situ by reacting equivalent of (cyanomethyl)triphenylphosphonium chloride in THF at −78° C. with 1 equivalent of n-butyllithium) was reacted at room temperature. The reaction mixture was concentrated in vacuo and the residue was stirred with petroleum ether and filtered. The filtrate was concentrated and the residue was purified by silica gel column chromatography or radial thin layer chromatography followed by kugelrohr distillation to give the title compound as a colorless oil. $n_D^{25}$ 1.4915.

EXAMPLE 126

Preparation of 3-Pyridinecarboxylic acid, 4-(cyclopropylmethyl)-2-(difluoromethyl)-5-(3-ethoxy-3-oxo-1-propenyl)-6-(trifluoromethyl)-, methyl ester.

To a solution of 3.3 g (14.7 mmol) of triethylphosphonoacetate in 50 mL dry THF was added 0.6 g (15 mmol) sodium hydride (60% oil dispersion). The mixture was heated to reflux and was allowed to cool to room temperature. To the mixture was added 5.0 g (14.8 mmol) of Compound B2 and the resulting mixture was stirred for 20 min. To the mixture was added 10 mL of 2.4 N hydrochloric acid and 15 mL water. The mixture was made basic with solid sodium bicarbonate and extracted with ether. The ether layer was dried over magnesium sulfate, treated with decolorizing carbon, and filtered through silica gel. The filtrate was concentrated in vacuo and the residue was purified by HPLC (5% ethyl acetate/hexane) to give 4.7 g of the title compound as a colorless oil.

EXAMPLE 127

Preparation of 3-Pyridinecarboxylic acid, 4-(cyclopropylmethyl)-2-(difluoromethyl)-5-(2-methoxyethenyl)-6-(trifluoromethyl)-, methyl ester.

To a suspension of 5.6 g (16 mmol) of methoxymethyltriphenylphosphonium chloride in 100 mL dry THF cooled to −70° C. was added 6.5 mL (16 mmol) of 2.5 M n-butyllithium in hexane. The mixture was allowed to warm to 0° C. and was cooled back to −70° C. To the resulting deep red solution was added a solution of 5.0 g (15 mmol) of Compound B2 in 15 mL dry THF. The resulting solution was stirred at −70° C. for 5 min and was allowed to warm to room temperature. The solution was poured into aqueous ammoniun chloride and the mixture was extracted with ether. The ether layer was washed with brine, dried over magnesium sulfate, and filtered through silica gel. The filtrate was evaporated in vacuo and the residue was purified by HPLC (10% ethyl acetate/hexane) to give 2.5 g of the title product as a colorless oil, a yield of 46 %. $n_D^{25}$ 1.4772.

EXAMPLE 128

Preparation of 1H-Pyrazole, 1-[[5-(chloromethyl)-6-(difluoromethyl)-4-(2-methylpropyl)-2-(trifluoromethyl)-3-pyridinyl]carbonyl].

To a solution of 50 g (0.12 mol) 2-(difluoromethyl)-4-(2-methylpropyl)-5-(1H-pyrazole-1-ylcarbonyl)-6-(trifluoromethyl)-3-pyridinecarbonyl chloride, prepared as in Example 40 of U.S. Pat. No. 4,826,532, in 30 mL diglyme was added 7.0 g (0.19 mol) sodium borohydride causing an exotherm to 45° C. The reaction mixture was poured into 500 mL water, acidified slowly with conc. HCl and worked up as in the preparation of Example B. The crude product was kugelrohr distilled to give 40 g of distillate which was 94% pure 2-(difluoromethyl)-4-(2-methylpropyl)-5-[(1-pyrazole)carbonyl]-6-(trifluoromethyl)-3-pyridinemethanol. The distillate was held at reflux with 72 g thionyl chloride and 1.1 g pyridine for 2.5 hours. The reaction mixture was concentrated in vacuo and the residue was stirred with a mixture of 200 mL water and 300 mL ether. The ether layer was washed with water, dried over magnesium sulfate, and concentrated in vacuo. The residual solid was recrystallized from hexane to give 29 g of the title compound as a solid, a 61% yield. m.p. 89°-91° C.

EXAMPLE 129

Preparation of 1H-Pyrazole, 1-[[5-(cyanomethyl)-6-(difluoromethyl)-4-(2-methylpropyl)-2-(trifluoromethyl)-3-pyridinyl]carbonyl].

The Compound of Example 128 was reacted with produce the title compound as a solid in an 83% yield. m.p. 136.5°-140° C.

EXAMPLE 130

Preparation of 1H-Pyrazole, 1-[[5-(cyanoethyl)-6-(difluoromethyl)-4-(2-methylpropyl)-2-(trifluoromethyl)-3-pyridinyl]carbonyl].

The Compound of Example 129 was reacted with methyl iodide using the procedure of Example 9 to produce the title compound as a solid in a 34% yield. m.p. 138.5°-141° C.

EXAMPLE 131

Preparation of 1H-Pyrazole, 1-[[5-(1-cyano-3-butenyl)-6-(difluoromethyl)-4-(2-methylpropyl)-2-(trifluoromethyl)-3-pyridinyl]carbonyl].

The Compound of Example 129 was reacted with allyl bromide using the procedure of Example 9 to produce the title compound as a syrup in a 94% yield. $n_D^{25}$ 1 5019.

EXAMPLE 132

Preparation of Pyridine, 3-[(butylthio)methyl]-2-(difluoromethyl)-4-(2-methylpropyl)-5-[(1H-pyrazol-1-yl)carbonyl]-6-(trifluoromethyl)-.

A mixture of 5.5 g (13 mmol) of the Compound of Example 29, 4.4 g (78 mmol) potassium hydroxide, 30 mL methanol, and 10 mL water was held at reflux for 42 hours and concentrated. The residue was diluted with water and extracted with ether. The aqueous layer was acidified with conc. HCl. The oily precipitate was extracted into ether. The ether layer was dried over magnesium sulfate and concentrated in vacuo. The residual oil was held at reflux with 16 g (0.14 mol) thionyl chloride for 1 hour and concentrated in vacuo. The residue was dissolved in 20 mL toluene and treated with 4.3 g (63 mmol) pyrazole. The mixture was stirred at room temperature overnight and diluted with 100 mL toluene. The toluene solution was washed successively with 3 N hydrochloric acid and brine, dried over magnesium sulfate, and concentrated in vacuo. The residue (4.3 g) was kugelrohr distilled at 1 torr (150° C.). The distillate was purified first by HPLC (10% ethyl acetate/cyclohexane) followed by radial thin layer chromatography (2% ethyl acetate/cyclohexane) to give 0.8 g of the title compound as a syrup after kugelrohr distillation at 1 torr (140°-150° C.). $n_D^{25}$ 1.5062.

EXAMPLE 133

Preparation of Pyridine, 2-(difluoromethyl)-4-(2-methylpropyl)-5-(1H-pyrazol-1-ylcarbonyl)-3-(1H-pyrazole-1-ylmethyl)-6-(trifluoromethyl)-.

To a solution of 20.6 g (60 mmol) of Compound A2 in 120 mL carbon tetrachloride was added 46.1 g (0.18 mol) boron tribromide. The reaction mixture was stirred at room temperature overnight and carefully poured into ice water. The organic was extracted into ether and the ether layer was extracted with saturated sodium bicarbonate. The sodium bicarbonate layer was acidified and the oily precipitate was extracted in ether. The ether layer was dried over magnesium sulfate, and concentrated in vacuo. The residue (23 g) was held at reflux with 83 g thionyl chloride for 18 hours and concentrated in vacuo. The residue was kugelrohr distilled at 0.2 torr. The first fraction (b.p. 90°-100° C.) was 8.4 g of an oil. A mixture of this oil, 5.1 g (69 mmol) of pyrazole, and 30 mL toluene was held at reflux for 23 hours; cooled; diluted with 100 mL ether and washed successively with 6 N hydrochloric acid, water, saturated sodium bicarbonate, and brine; dried over magnesium sulfate; and concentrated in vacuo to give 8.4 g of a syrup which was kugelrohr distilled at 0.4 torr to give 7.2 g of the title compound as a brown syrup, a 28% yield.

EXAMPLE 134

Preparation of 3-Pyridinecarbothioic acid, 2-(difluoromethyl)-4-(2-methylpropyl)-5-[(methylthio)methyl]-6-(trifluoromethyl)-, S-methyl ester.

The Compound of Example 27 was hydrolyzed with potassium hydroxide to the corresponding acid which was reacted with thionyl chloride at reflux to give 2-(difluoromethyl)-4-(2-methylpropyl)-5-[(methylthio)methyl]-6-(trifluoromethyl)-3-pyridinecarbonyl chloride. A mixture of 2.1 g (56 mmol) of this acid chloride, 100 mL THF, 20 mL hexamethylphosphoramide, and 1 g sodium methanethiolate, was stirred overnight and concentrated in vacuo. The residue was triturated with water and extracted with ether. The ether layer was washed with water, dried over magnesium sulfate, and concentrated in vacuo. The residue was purified by column chromatography (10% ethyl acetate/cyclohexane) to give 0.6 g of the title compound as an oil, a 28% yield.

EXAMPLE 135

Preparation of 3-Pyridinecarboxylic acid, 5-(2-bromoethyl)-2-(difluoromethyl)-4-(2-methylpropyl)-6-(trifluoromethyl)-, methyl ester.

Reaction of the Compound of Example 20 according to the procedure in Example 103 gave a colorless oil after radial thin layer chromatography (10% methylene chloride/cyclohexane.

EXAMPLE 136

Preparation of 3-Pyridinecarboxylic acid, 5-(azidomethyl)-4-(cyclopropylmethyl)-2-(difluoromethyl)-6-(trifluoromethyl)-, methyl ester.

To a solution of 10.0 g (28 mmol) of the Compound of Example 4 in 60 mL acetone was added 3.3 g (51 mmol) sodium azide and 40 mL water. The mixture was heated to reflux for 45 min, cooled, and partitioned between ether and brine. The organic layer was dried over magnesium sulfate, filtered through silica gel, and the filtrate was evaporated in vacuo. The residue was distilled to yield 9.1 g of the title compound as a colorless oil, an 89% yield. b.p. 130°-133° C. (0.2 torr).

EXAMPLE 137

Preparation of 3-Pyridinecarboxylic acid, 5-(aminomethyl)-4-(cyclopropylmethyl)-2-(difluoromethyl)-6-(trifluoromethyl)-, methyl ester.

To a solution of 4.5 g (12.4 mmol) of the Compound of Example 136 in 30 mL ethanol was added 0.3 g of wet 5% palladium on carbon. The mixture was subjected to 50 psi of hydrogen for 3 hours. The mixture was filtered and the filtrate was evaporated in vacuo. The residue was purified by HPLC (25% ethyl acetate/hexane) to yield 3.7 g of the title compound as a yellow oil, an 88% yield. $n_D^{25}$ 1.4766.

EXAMPLE 138

Preparation of 3-Pyridinecarboxylic acid, 6-(bromomethyl)-5-(1-hydroxypropyl)-4-(2-methylpropyl)-2-(trifluoromethyl)-, methyl ester.

To a solution of 5.0 g (16 mmol) of Compound B5 in 10 mL ether was added dropwise 7 mL (20 mmol) of 2.9 M ethyl magnesium bromide in ether. The reaction mixture was poured into 1 N hydrochloric acid. The organic was extracted into ether, and the ether extract was washed successively with saturated sodium bicarbonate and brine, dried over magnesium sulfate, and concentrated in vacuo. The residue (5.0 g) was purified by HPLC (10% ethyl acetate/cyclohexane). After removal of the first fraction, the second fraction was kugelrohr distilled at 1 torr (170° C.) to give 0.8 g of oil which contained two components even though the material prior to kugelrohr distillation was essentially pure by NMR and TLC. This oil was purified by radial thin layer chromatography (10% ethyl acetate/hexane) to give 0.44 g of a solid from the second fraction, a 7% yield. m.p. 72.5°-78° C.

EXAMPLE 139

Preparation of 3-Pyridinecarboxylic acid, 5-(chloromethyl)-2-methoxy-4-(2-methylpropyl)-6-(trifluoromethyl)-, methyl ester.

Reaction of Compound A5 with thionyl chloride using the method of Example 1 gave the title compound as an oil. $n_D^{25}$ 1.4762.

EXAMPLE 140

Preparation of 3-Pyridinecarboxylic acid, 5-(ethylthio)methyl-2-methoxy-4-(2-methylpropyl)-6-(trifluoromethyl)-, methyl ester.

Reaction of 0.01 mol of the Compound of Example 39 in THF with a solution sodium ethanethiolate, prepared from 0.03 mol sodium metal, 25 mL methanol, and 0.034 mol ethanethiol, according to the method of Example 27 yielded 7.6 g of the title compound as an oil, a 66% yield. $n_D^{25}$ 1.4792.

EXAMPLE 141

Preparation of 3-Pyridinecarboxylic acid, 2-methoxy-5-[[(1-methylethyl)thio]methyl-4-(2-methylpropyl)-6-(trifluoromethyl)-, methyl ester.

Reaction of 8 mmol of the Compound of Example 139 in THF with a solution sodium isopropanethiolate (prepared from 27 mmol sodium metal, 25 mL methanol, and 32 mmol 2-propanethiol), according to the method of Example 27 yielded 3.1 g of the title compound as an oil, a 97% yield. $n_D^{25}$ 1.4901.

EXAMPLE 142

Preparation of 3-Pyridinecarboxylic acid, 5-(1-ethoxypropyl)-2-methoxy-4-(2-methylpropyl)-6-(trifluoromethyl)-, methyl ester.

Reaction of Compound B4 with ethyl magnesium bromide according to the method of Example 19 gave 3-pyridinecarboxylic acid, 5-(1-hydroxypropyl)-2-methoxy-4-(2-methylpropyl)-6-(trifluoromethyl)-, methyl ester, which was reacted with ethyl iodide using the method of Example 61 yielded the title compound as a colorless oil. $n_D^{25}$ 4644.

EXAMPLE 143

Preparation of 3-Pyridinecarboxylic acid, 5-(1-ethoxy-2-propenyl)-2-methoxy-4-(2-methylpropyl)-6-(trifluoromethyl)-, methyl ester.

Reaction of Compound B4 with vinyl magnesium bromide using the method of Example 19 gave 3-pyridinecarboxylic acid, 5-(1-hydroxy-2-propenyl)-2-methoxy- 4-(2-methylpropyl)-6-(trifluoromethyl)-, methyl ester, which was reacted with ethyl iodide using the method of Example 61 yielded the title compound as a colorless oil. $n_D^{25}$ 14717.

EXAMPLE 144

Preparation of 3-Pyridinecarboxylic acid, 2-methoxy-5-(1-methoxypropyl)-4-(2-methylpropyl)-6-(trifluoromethyl)-, methyl ester.

Reaction of 3-pyridinecarboxylic acid, 5-(1-hydroxypropyl)-2-methoxy-4-(2-methylpropyl)-6-(trifluoromethyl)-, methyl ester, described in Example 142, with methyl iodide using the method of Example 61 yielded the title compound as a colorless oil. $n_D^{25}$ 1.4660.

EXAMPLE 145

Preparation of 3-Pyridinecarboxylic acid, 2-methoxy-5-(1-methoxy-2-propenyl)-4-(2-methylpropyl)-6-(trifluoromethyl)-, methyl ester.

Reaction of 3-pyridinecarboxylic acid, 5-(1-hydroxy-2-propenyl)-2-methoxy-4-(2-methylpropyl)-6-(trifluoromethyl)-, methyl ester, described in Example 143, with methyl iodide using the method of Example 61 yielded the title compound as a colorless oil. $n_D^{25}$ 1.4740.

EXAMPLE 146

Preparation of 3-Pyridinecarboxylic acid, 5-(cyanomethyl)-2-methoxy-4-(2-methylpropyl)-6-(trifluoromethyl)-, methyl ester.

Reaction of the Compound of Example 139 with sodium cyanide by the method of Example 5 gave white crystals. m.p. 66°-67° C.

EXAMPLE 147

Preparation of 3-Pyridinecarboxylic acid, 5-(1-cyanopropyl)-4-(cyclopropylmethyl)-2-methoxy-6-(trifluoromethyl)-, methyl ester.

Reaction of Compound B6 with ethyl magnesium bromide by the method of Example 19 gave 3-pyridinecarboxylic acid, 4-(cyclopropylmethyl)-5-(1-hydroxypropyl)- 2-methoxy-6-(trifluoromethyl)-, methyl ester, which was reacted with triphenylphosphine and carbon tetrachloride according to the procedure of Example 26 to give crude 3-pyridinecarboxylic acid, 5-(1-chloropropyl)-4-(cyclopropylmethyl)-2-methoxy-6-(trifluoromethyl)-, methyl ester. Reaction of this material with sodium cyanide using the method of Example 5 gave the title compound as a colorless oil. $n_D^{25}$ 1.4768.

EXAMPLE 148

Preparation of 3-Pyridinecarboxylic acid, 6-(difluoromethyl)-5-(1-hydroxypropyl)-4-(2-methylpropyl)-2-(trifluoromethyl)-, methyl ester.

Reaction of Compound B3 with ethyl magnesium bromide by the method of Example 19 yielded a solid. m.p. 94°-96° C.

PRE-EMERGENT ACTIVITY ON PLANTS

As noted above, compounds of this invention have been found to be effective as herbicides, particularly pre-emergent herbicides. Tables A and B summarize results of tests conducted to determine the pre-emergent herbicidal activity of the compounds of this invention. The herbicidal ratings used in Tables A and B were assigned according to a scale based on the percent inhibition of each plant species. The herbicide rating symbols in Tables A and B are defined as follows:

| % Inhibition | Rating |
|---|---|
| 0-24 | 0 |
| 25-49 | 1 |
| 50-74 | 2 |
| 75-100 | 3 |
| Not planted | — or a blank |
| Species planted, no data | N |

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.2 kilograms/hectare (kg/ha). After treatment, the pans were moved to a greenhouse bench where they were watered as needed to give adequate moisture for germination and growth.

Approximately 10-14 days (usually 11 days) after planting and treating, the plants were observed and the results recorded.

The plant species usually regarded as weeds which were utilized in one set of pre-emergent activity tests, the data for which are shown in Table A, are identified by letter headings printed diagonally above the columns according to the following legend:

CATH—Canada thistle*
RHQG—Quackgrass*
COBU—Cocklebur
RHJG—Rhizome Johnsongrass*
VELE—Velvetleaf
DOBR—Downy Brome
MOGL—Morningglory
BYGR—Barnyardgrass
COLQ—Common Lambsquarters
ANBG—Annual Bluegrass
PESW—Pennsylvania Smartweed
SEJG—Seedling Johnsongrass
YENS—Yellow Nutsedge*
INMU—Indian Mustard
WIBW—Wild Buckwheat

* Grown from vegetative propagules

TABLE A

Herbicide Primary Pre, spectrums 25 and 90 (C = 100% control)

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 1 | 11.2100 | 0 | — | — | 0 | 0 | 0 | 0 | 0 | — | — | — | 3 | 0 | 0 | 0 |
| 2 | 11.2100 | 0 | — | — | 1 | 3 | 1 | 0 | 2 | — | — | 0 | 3 | 0 | 0 | 0 |
| 3 | 11.2100 | 0 | — | — | 1 | 3 | 1 | 0 | 0 | — | — | 0 | 3 | 3 | 1 | 0 |
| 4 | 11.2100 | 1 | — | — | 3 | 3 | 3 | 0 | 3 | — | — | 3 | 3 | 3 | 3 | 2 |
| 5 | 11.2100 | 2 | — | — | 3 | 3 | 3 | 0 | 3 | — | — | — | 3 | 3 | 3 | 2 |
| 6 | 11.2100 | 0 | — | — | 3 | 3 | 3 | 0 | 3 | — | — | — | 3 | 3 | 3 | N |
| 7 | 11.2100 | 0 | — | — | 3 | 3 | 3 | 0 | 3 | — | — | 0 | 3 | 3 | 3 | 3 |
| 8 | 11.2100 | 0 | — | — | 2 | 3 | 3 | 0 | 3 | — | — | 0 | 3 | N | 3 | 0 |
| 9 | 11.2100 | 3 | — | — | 3 | 3 | 3 | 3 | 3 | — | — | 3 | 3 | 3 | 3 | 3 |

TABLE A-continued

| Ex. No. | | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|---|
| | | | Herbicide Primary Pre. spectrums 25 and 90 (C = 100% control) | | | | | | | | | | | | | | |
| 10 | | 11.2100 | 3 | — | — | 3 | 3 | 3 | 2 | 3 | — | — | 3 | 3 | 3 | 3 | 3 |
| 11 | | 11.2100 | 3 | — | — | 3 | 3 | 3 | 2 | 3 | — | — | 3 | 3 | 3 | 3 | 0 |
| 12 | | 11.2100 | 1 | — | — | 3 | 3 | 3 | 0 | 1 | — | — | 3 | 3 | N | 3 | 0 |
| 13 | | 11.2100 | 1 | — | — | 3 | 3 | 3 | 0 | 2 | — | — | 3 | 3 | N | 3 | 1 |
| 14 | | 11.2100 | 0 | — | — | 3 | 3 | 3 | 1 | 3 | — | — | 3 | 3 | N | 3 | 3 |
| 15 | | 11.2100 | 0 | — | — | 3 | 3 | 3 | 0 | 3 | — | — | 1 | 3 | N | 3 | 3 |
| 16 | | 11.2100 | 1 | 3 | 3 | 0 | 3 | 3 | 1 | 3 | 3 | 3 | — | — | — | — | — |
| 17 | | 11.2100 | 3 | 3 | 3 | 3 | 3 | 3 | 0 | 3 | 3 | 3 | — | — | — | — | — |
| 18 | | 11.2100 | 0 | 3 | 3 | 3 | 3 | 2 | 0 | 2 | 3 | 3 | — | — | — | — | — |
| 19 | | 11.2100 | 3 | — | — | 3 | 3 | 3 | 0 | 3 | — | — | 3 | 3 | 3 | 3 | 0 |
| 20 | | 11.2100 | 1 | — | — | 3 | 3 | 2 | 1 | 3 | — | — | 3 | 3 | 3 | 3 | 3 |
| 21 | } | 11.2100 | 1 | 3 | 3 | 2 | 3 | 3 | 0 | 3 | 3 | 3 | — | — | — | — | — |
| 22 | [ | 11.2100 | 2 | 3 | 3 | 3 | 3 | 3 | 3 | 3 | 3 | 3 | — | — | — | — | — |
| 23 | : | 11.2100 | 3 | 3 | 3 | 3 | 3 | 3 | 1 | 3 | 3 | 3 | — | — | — | — | — |
| 24 | | 11.2100 | 3 | — | — | 2 | 3 | 3 | 0 | 3 | — | — | 1 | 3 | 3 | 3 | 3 |
| 25 | | 11.2100 | 3 | — | — | 3 | 3 | 3 | 3 | 3 | — | — | 3 | 3 | 3 | 3 | 3 |
| 26 | | 11.2100 | 2 | — | — | 3 | 3 | 3 | 2 | 3 | — | — | 3 | 3 | 3 | 3 | 3 |
| 27 | | 11.2100 | 3 | — | — | 3 | 3 | 3 | 3 | 3 | — | — | 3 | 3 | 3 | 3 | 3 |
| | | 11.2100 | 3 | — | — | 3 | 3 | 3 | 3 | 3 | — | — | 3 | 3 | 3 | 3 | 3 |
| 28 | | 11.2100 | 1 | — | — | 2 | 3 | 3 | 0 | 2 | — | — | 0 | 3 | 2 | 3 | 0 |
| 29 | | 11.2100 | 0 | — | — | 0 | 3 | 0 | 0 | 0 | — | — | 0 | 3 | 2 | 0 | 0 |
| 30 | | 11.2100 | 1 | — | — | 3 | 3 | 3 | 0 | 2 | — | — | 0 | 3 | 3 | 3 | 3 |
| 31 | | 11.2100 | 3 | — | — | 3 | 3 | 3 | 1 | 3 | — | — | 3 | 3 | 3 | 3 | 3 |
| 32 | | 11.2100 | 0 | — | — | 0 | 3 | 0 | 0 | 0 | — | — | 1 | 3 | 0 | 3 | 0 |
| 33 | | 11.2100 | 2 | — | — | 3 | 3 | 3 | 3 | 3 | — | — | 3 | 3 | 3 | 3 | 3 |
| 34 | | 11.2100 | 0 | — | — | 3 | 3 | 2 | 1 | 3 | — | — | 1 | 3 | 3 | 3 | 0 |
| 35 | | 11.2100 | 3 | — | — | 3 | 3 | 3 | 3 | 3 | — | — | 3 | 3 | 3 | 3 | 3 |
| 36 | | 11.2100 | 0 | — | — | 3 | 3 | 3 | 0 | 2 | — | — | 0 | 3 | 3 | 3 | 3 |
| 37 | | 11.2100 | 3 | — | — | 3 | 3 | 3 | 3 | 3 | — | — | 3 | 3 | 3 | 3 | 3 |
| 38 | | 11.2100 | 3 | — | — | 3 | 3 | 3 | 0 | 2 | — | — | 0 | 3 | 3 | 3 | 3 |
| 39 | | 11.2100 | 3 | — | — | 3 | 3 | 3 | 1 | 3 | — | — | 0 | 3 | 3 | 3 | 0 |
| 40 | | 11.2100 | 2 | — | — | 3 | 3 | 2 | 2 | 2 | — | — | 1 | 3 | 1 | 3 | 0 |
| 41 | | 11.2100 | 1 | — | — | 3 | 3 | 3 | 3 | 3 | — | — | 3 | 3 | 2 | 3 | 3 |
| 42 | | 11.2100 | 0 | — | — | 2 | 3 | 0 | 0 | 0 | — | — | 0 | 1 | 1 | 0 | N |
| 43 | | 11.2100 | 1 | — | — | 3 | 3 | 3 | 2 | 3 | — | — | — | 3 | 3 | 3 | 3 |
| 44 | | 11.2100 | 0 | — | — | 3 | 3 | 2 | 0 | 2 | — | — | — | 3 | 1 | 2 | 1 |
| 45 | | 11.2100 | 0 | — | — | 3 | 3 | 3 | 0 | 3 | — | — | 3 | 3 | 3 | 2 | 0 |
| 46 | | 11.2100 | 0 | — | — | 3 | 3 | 2 | 0 | 1 | — | — | 0 | 3 | 3 | 3 | 1 |
| 47 | | 11.2100 | 3 | — | — | 3 | 3 | 3 | 3 | 3 | — | — | 3 | 3 | 3 | 3 | 3 |
| 48 | | 11.2100 | 0 | — | — | 3 | 3 | 2 | 3 | 3 | — | — | 3 | 3 | 2 | 3 | 0 |
| 49 | | 11.2100 | 1 | — | — | 3 | 3 | 3 | 3 | 3 | — | — | 3 | 3 | 3 | 3 | 3 |
| 50 | | 11.2100 | 1 | — | — | 3 | 3 | 3 | 3 | 3 | — | — | 3 | 3 | 3 | 3 | 3 |
| 51 | | 11.2100 | 3 | — | — | 2 | 3 | 3 | 0 | 3 | — | — | 3 | 3 | 3 | 3 | — |
| 52 | | 11.2100 | 0 | — | — | 0 | 3 | 3 | 0 | 3 | — | — | 1 | 3 | 3 | 3 | — |
| 53 | | 11.2100 | 2 | — | — | 3 | 3 | 3 | 1 | 3 | — | — | 3 | 3 | N | 3 | 3 |
| 54 | | 11.2100 | 3 | — | — | 3 | 3 | 3 | 3 | 3 | — | — | 3 | 3 | N | 3 | 3 |
| 55 | | 11.2100 | 0 | 3 | 3 | 3 | 3 | 3 | 3 | 3 | 3 | 3 | — | — | — | — | — |
| 56 | | 11.2100 | 2 | 3 | 3 | 3 | 3 | 3 | 2 | 3 | 3 | 3 | — | — | — | — | — |
| 57 | | 11.2100 | 1 | 3 | 3 | 3 | 3 | 3 | 1 | 3 | 3 | 3 | — | — | — | — | — |
| 58 | | 11.2100 | 1 | 3 | 3 | 3 | 3 | 3 | 0 | 3 | 3 | 3 | — | — | — | — | — |
| 59 | | 11.2100 | 3 | — | — | 3 | 3 | 3 | 2 | 3 | — | — | 3 | 3 | 3 | 3 | 3 |
| 60 | | 11.2100 | 2 | — | — | 3 | 3 | 3 | 1 | 3 | — | — | 3 | 3 | 3 | 3 | 3 |
| 61 | | 11.2100 | 3 | — | — | 3 | 3 | 3 | 1 | 3 | — | — | 3 | 3 | N | 3 | 3 |
| 62 | | 11.2100 | 3 | 3 | 3 | 3 | 3 | 3 | 3 | 3 | 3 | 3 | — | — | — | — | — |
| 63 | C | 11.2100 | 3 | 3 | 3 | 3 | 3 | 3 | 2 | 3 | 3 | 3 | — | — | — | — | — |
| 64 | : | 11.2100 | 3 | 3 | 3 | 3 | 3 | 3 | 3 | 3 | 3 | 3 | — | — | — | — | — |
| 65 | E | 11.2100 | 3 | 3 | 3 | 3 | 3 | 3 | 1 | 3 | 3 | 3 | — | — | — | — | — |
| 66 | : | 11.2100 | 3 | 3 | 3 | 3 | 3 | 3 | 3 | 3 | 3 | 3 | — | — | — | — | — |
| 67 | } | 11.2100 | 3 | 3 | 3 | 3 | 3 | 3 | 1 | 3 | 3 | 3 | — | — | — | — | — |
| 68 | } | 11.2100 | 2 | 3 | 3 | 3 | 3 | 3 | 1 | 3 | 3 | 3 | — | — | — | — | |
| 69 | } | 11.2100 | 3 | 3 | 3 | 3 | 3 | 3 | 1 | 3 | 3 | 3 | — | — | — | — | — |
| 70 | } | 11.2100 | 3 | 3 | 3 | 3 | 3 | 3 | 1 | 3 | 3 | 3 | — | — | — | — | — |
| 71 | } | 11.2100 | 0 | 3 | 3 | 3 | 3 | 3 | 1 | 3 | 3 | 3 | — | — | — | — | — |
| 72 | A | 11.2100 | 0 | 3 | 3 | 3 | 3 | 2 | 0 | 1 | 0 | 1 | — | — | — | — | — |
| 73 | G | 11.2100 | 0 | 3 | 3 | 3 | 3 | 2 | 0 | 2 | 2 | 0 | — | — | — | — | — |
| 74 | G | 11.2100 | 3 | 3 | 3 | 3 | 3 | 3 | 2 | 3 | 3 | 3 | — | — | — | — | — |
| 75 | G | 11.2100 | 3 | 3 | 3 | 3 | 3 | 3 | 2 | 3 | 3 | 3 | — | — | — | — | — |
| 76 | % | 11.2100 | 2 | 3 | 3 | 3 | 3 | 3 | 3 | 3 | 3 | 3 | — | — | — | — | — |
| 77 | | 11.2100 | 0 | 3 | 3 | 3 | 3 | 3 | 2 | 3 | 3 | 3 | — | — | — | — | — |
| 78 | | 11.2100 | 3 | 3 | 3 | 3 | 3 | 3 | 3 | 3 | 3 | 3 | — | — | — | — | — |
| 79 | | 11.2100 | 1 | — | — | 3 | 3 | 2 | 0 | 2 | — | — | 1 | 3 | 1 | 2 | 1 |
| 80 | | 11.2100 | 0 | 3 | 3 | 3 | 3 | 3 | 0 | 3 | 3 | 3 | — | — | — | — | — |
| 81 | | 11.2100 | 2 | 3 | 3 | 3 | 3 | 3 | 0 | 3 | 3 | 3 | — | — | — | — | — |
| 82 | | 11.2100 | 2 | 3 | 3 | 3 | 3 | 3 | 0 | 3 | 3 | 3 | — | — | — | — | — |
| 83 | | 11.2100 | 2 | — | — | 3 | 3 | 3 | 3 | 3 | — | — | 3 | 3 | 3 | 3 | 0 |
| 84 | | 11.2100 | 2 | — | — | 3 | 3 | 3 | 1 | 3 | — | — | 3 | 3 | 3 | 1 | 3 |
| 85 | | 11.2100 | 3 | — | — | 3 | 3 | 3 | 2 | 3 | — | — | 3 | 3 | 3 | 3 | 3 |
| 86 | | 11.2100 | 3 | 3 | 3 | 3 | 3 | 3 | 2 | 3 | 3 | 3 | — | — | — | — | — |

TABLE A-continued

Herbicide Primary Pre, spectrums 25 and 90 (C = 100% control)

| Ex. No. | | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|---|
| 87 | | 11.2100 | 3 | 3 | 3 | 3 | 3 | 3 | 3 | 3 | 3 | 3 | — | — | — | — | — |
| 88 | | 11.2100 | 1 | 3 | 3 | 3 | 3 | 2 | 2 | 3 | 3 | 3 | — | — | — | — | — |
| 89 | | 11.2100 | 0 | — | — | 3 | 3 | 3 | 3 | 2 | — | — | 3 | 3 | 3 | 3 | 3 |
| 90 | | 11.2100 | 0 | — | — | 3 | 3 | 3 | 1 | 3 | — | — | 3 | 3 | 3 | 3 | 3 |
| 91 | | 11.2100 | 0 | — | — | 0 | 3 | 0 | 0 | 1 | — | — | 3 | 1 | 1 | 0 | 0 |
| 92 | | 11.2100 | 0 | 3 | 3 | 3 | 3 | 3 | 0 | 3 | 3 | 3 | — | — | — | — | — |
| 93 | | 11.2100 | 1 | 3 | 3 | 2 | 3 | 3 | 0 | 3 | 3 | 3 | — | — | — | — | — |
| 94 | | 11.2100 | 1 | — | — | 1 | 3 | 0 | 0 | 1 | — | — | — | 3 | 3 | 0 | 0 |
| 95 | | 11.2100 | 3 | — | — | 3 | 3 | 2 | 0 | 2 | — | — | 0 | 3 | 3 | 3 | 0 |
| 96 | = | 11.2100 | 1 | — | — | 1 | 3 | 1 | 0 | 1 | — | — | 1 | 3 | N | 3 | 0 |
| 97 | | 11.2100 | 3 | 3 | 3 | 3 | 3 | 3 | 3 | 3 | 3 | 3 | — | — | — | — | — |
| 98 | | 11.2100 | 3 | 3 | 3 | 3 | 3 | 3 | 0 | 3 | 3 | 3 | — | — | — | — | — |
| 99 | | 11.2100 | 2 | — | — | 3 | 3 | 3 | 2 | 3 | — | — | 3 | 3 | 3 | 3 | 3 |
| 100 | | 11.2100 | 3 | — | — | 3 | 3 | 3 | 1 | 3 | — | — | 2 | 3 | 3 | 3 | 3 |
| 101 | | 11.2100 | 0 | — | — | 1 | 3 | 0 | 0 | 0 | — | — | 0 | 3 | N | 3 | 0 |
| 102 | | 11.2100 | 3 | — | — | 3 | 3 | 3 | 1 | 3 | — | — | 3 | 3 | 3 | 3 | 0 |
| 103 | | 11.2100 | 0 | — | — | 3 | 3 | 3 | 0 | 2 | — | — | 2 | 3 | 2 | 2 | N |
| 104 | | 11.2100 | 0 | — | — | 2 | 3 | 3 | 0 | 3 | — | — | 2 | 3 | 2 | 1 | 1 |
| 105 | | 11.2100 | 0 | — | — | 3 | 3 | 2 | 0 | 1 | — | — | 0 | 3 | 1 | 3 | 0 |
| 106 | | 11.2100 | 3 | — | — | 3 | 3 | 3 | 2 | 3 | — | — | 2 | 3 | 3 | 3 | 3 |
| 107 | | 11.2100 | 0 | — | — | 3 | 3 | 0 | 0 | 1 | — | — | 0 | 3 | 2 | 2 | 1 |
| 108 | | 11.2100 | 3 | — | — | 3 | 3 | 3 | 1 | 3 | — | — | 0 | 3 | 3 | 3 | 2 |
| 109 | | 11.2100 | 0 | — | — | 3 | 3 | 3 | 0 | 3 | — | — | 3 | 3 | 3 | 3 | 0 |
| 110 | | 11.2100 | 0 | — | — | 3 | 3 | 3 | 0 | 2 | — | — | 0 | 3 | 3 | 3 | 3 |
| 111 | | 11.2100 | 3 | — | — | 3 | 3 | 3 | 2 | 3 | — | — | 3 | 3 | 3 | 3 | 3 |
| 112 | | 11.2100 | 3 | — | — | 3 | 3 | 3 | 3 | 3 | — | — | 3 | 3 | 3 | 3 | 3 |
| 113 | | 11.2100 | 2 | — | — | 3 | 3 | 3 | 3 | 3 | — | — | 3 | 3 | 3 | 3 | 1 |
| 114 | | 11.2100 | 3 | — | — | 3 | 3 | 3 | 0 | 3 | — | — | 3 | 3 | 3 | 3 | 0 |
| 115 | | 11.2100 | 3 | — | — | 3 | 3 | 3 | 3 | 3 | — | — | 3 | 3 | 3 | 3 | 3 |
| 116 | | 11.2100 | 0 | — | — | 2 | 0 | 0 | 0 | 0 | — | — | 0 | 0 | N | 0 | N |
| 117 | | 11.2100 | 0 | — | — | 3 | 3 | 3 | 0 | 3 | — | — | 0 | 3 | 2 | 2 | 1 |
| 118 | | 11.2100 | 0 | — | — | 0 | 0 | 0 | 0 | 0 | — | — | 0 | 0 | 0 | 0 | N |
| 119 | | 11.2100 | 2 | — | — | 2 | 3 | 1 | 0 | 1 | — | — | 1 | 3 | 1 | 0 | N |
| 120 | | 11.2100 | 0 | — | — | 1 | 3 | 3 | 0 | 2 | — | — | 3 | 3 | 3 | 0 | 0 |
| 121 | | 11.2100 | 0 | 3 | 0 | 0 | 0 | 0 | 0 | 0 | 2 | 0 | — | — | — | — | — |
| 122 | | 11.2100 | 0 | — | — | 1 | 1 | 0 | 0 | 0 | — | — | 0 | 3 | 2 | 0 | 0 |
| 123 | | 11.2100 | 0 | — | — | 3 | 3 | 0 | 0 | 0 | — | — | 0 | 3 | 3 | 0 | 0 |
| 124 | | 11.2100 | 2 | — | — | 3 | 3 | 1 | 0 | 2 | — | — | 0 | 3 | 2 | 2 | 0 |
| 125 | | 11.2100 | 0 | 3 | 3 | 2 | 3 | 3 | 0 | 3 | 2 | 3 | — | — | — | — | — |
| 126 | | 11.2100 | 0 | — | — | 3 | 3 | 0 | 0 | 0 | — | — | 0 | 3 | N | 3 | 0 |
| 127 | } | 11.2100 | 3 | 3 | 3 | 3 | 3 | 3 | 2 | 3 | 3 | 3 | — | — | — | — | — |
| 128 | > | 11.2100 | 0 | 1 | 0 | 0 | 2 | 0 | 0 | 0 | 0 | 0 | — | — | — | — | — |
| 129 | > | 11.2100 | 0 | 3 | 0 | 0 | 0 | 0 | 0 | 0 | 0 | 0 | — | — | — | — | — |
| 130 | | 11.2100 | 0 | 3 | 3 | 3 | 3 | 2 | 0 | 2 | 3 | 3 | — | — | — | — | — |
| 131 | | 11.2100 | 0 | 3 | 3 | 3 | 3 | 3 | 0 | 3 | 3 | 3 | — | — | — | — | — |
| 132 | | 11.2100 | 0 | — | — | 0 | 0 | 0 | 0 | 0 | — | — | 0 | 0 | 0 | 0 | 0 |
| 133 | | 11.2100 | 0 | — | — | 3 | 3 | 3 | 0 | 3 | — | — | 3 | 3 | 3 | 3 | 0 |
| 134 | | 11.2100 | 3 | — | — | 3 | 3 | 3 | 2 | 3 | — | — | 3 | 3 | 3 | 3 | 2 |
| 135 | | 11.2100 | 3 | — | — | 3 | 3 | 3 | 3 | 3 | — | — | 3 | 3 | 3 | 3 | 3 |
| 136 | | 11.2100 | 3 | — | — | 3 | 3 | 3 | 0 | 3 | — | — | 3 | 3 | N | 3 | 3 |
| 137 | | 11.2100 | 0 | — | — | 1 | 3 | 0 | 0 | 0 | — | — | 0 | 0 | N | 0 | 0 |
| 138 | % | 11.2100 | 0 | 3 | 3 | 1 | 3 | 2 | 0 | 2 | 1 | 2 | — | — | — | — | — |
| 139 | H | 11.2100 | 0 | — | — | N | 2 | 0 | 0 | 1 | — | — | 0 | 3 | 1 | 1 | N |
| 140 | | 11.2100 | 3 | — | — | 3 | 3 | 3 | 3 | 3 | — | — | 3 | 3 | 3 | 3 | 3 |
| 141 | | 11.2100 | 2 | — | — | 3 | 3 | 3 | 1 | 3 | — | — | 3 | 3 | 3 | 3 | 3 |
| 142 | } | 11.2100 | 0 | 3 | 3 | 3 | 3 | 3 | 0 | 2 | 3 | 3 | — | — | — | — | — |
| 143 | } | 11.2100 | 0 | 3 | 3 | 3 | 3 | 3 | 0 | 3 | 3 | 2 | — | — | — | — | — |
| 144 | } | 11.2100 | 0 | 3 | 3 | 3 | 3 | 3 | 1 | 3 | 3 | 3 | — | — | — | — | — |
| 145 | } | 11.2100 | 2 | 3 | 3 | 3 | 3 | 3 | 1 | 3 | 3 | 3 | — | — | — | — | — |
| 146 | | 11.2100 | 2 | 3 | 3 | 3 | 3 | 3 | 0 | 3 | 3 | 3 | — | — | — | — | — |
| 147 | | 11.2100 | 3 | 3 | 3 | 3 | 3 | 3 | 2 | 3 | 3 | 3 | — | — | — | — | — |
| 148 | | 11.2100 | 1 | — | — | 3 | 3 | 3 | 2 | 3 | — | — | 0 | 3 | 3 | 3 | 0 |

POOR GERMINATION-SW
= POOR SW AND CA GERMINATION.
> POOR GERMINATION-CB,SJ.
% DAMPING OFF-IM,WB.
[ DAMPING OFF-IM,WB. POOR GERMINATION-CB,WB.
: DAMPING OFF-IM,WB POOR GERMINATION-CB
} DAMPING OFF-IM,WB. POOR GERMINATION-WB.
A DAMPING OFF IM,WB.
C DAMPING OFF-IM. POOR GERMINATION-WB.
E DAMPING OFF - IM,WB. POOR GERMINATON - WB.
G SJ - POOR GERMINATION
H POOR GERMINATION-RJ, DAMPING OFF-DB.

In another set of tests, the pre-emergence activity of compounds of this invention was tested on weeds in the presence of crop plants. In these tests the following procedure was used:

Topsoil was sieved to pass through a 1.27 cm screen. Fertilizer was added to the topsoil in some of the tests, while in testing other compounds the fertilizer was omitted. The mixture was then sterilized by exposure to methyl bromide or by heating.

The topsoil mixture was placed in individual aluminum pans and compacted to a depth of about 1.27 cm. from the top of the pan. A predetermined number of seeds of each of several monocotyledonous and dicotyledonous plant species and, where noted, vegetative propagules of various perennial plant species were slanted in the pans. The soil required to level fill a pan after seeding or adding vegetative propagules was weighed into another pan. A known amount of the test compound was dissolved or suspended in acetone or a suitable organic solvent as a 1% solution or suspension and applied to the cover soil using a sprayer at the desired rate. The spray was thoroughly mixed with this cover soil, and the herbicide/soil mixture was used as a cover layer for the previously prepared pan. Untreated soil was used as a cover layer for control pans. In Table B below the amount of active ingredient applied is shown. After treatment, the pans were moved to a greenhouse bench. Moisture was supplied to each pan as needed for germination and growth. Growth of each species was observed and corrective measures (greenhouse fumigation, insecticide treatment, and the like) were applied as needed. Approximately 10–14 days (usually 11 days) after planting and treating, the plants were observed and the results recorded.

The pre-emergence data for weeds in the presence of crop plants are shown in the following Table B. In these tests, the plants are identified according to the following column headings.

| | |
|---|---|
| SOBE - Soybean | VELE - Velvetleaf |
| SUBE - Sugarbeet | DOBR - Downy Brome |
| WHEZ - Wheat | PRMI - Proso Millet |
| RICE - Rice | BYGR - Barnyardgrass |
| GRSO - Grain Sorghum | LACG - Large Crabgrass |
| COBU - Cocklebur | GRFT - Green Foxtail |
| WIBW - Wild Buckwheat | CORN - Corn |
| MOGL - Morningglory | COTZ - Cotton |
| HESE - Hemp Sesbania | RAPE - Oilseed Rape |
| COLQ - Common Lambsquarters | JIWE - Jimsonweed |
| PESW - Pennsylvania Smartweed | COCW - Common Chickweed |

TABLE B

| Ex. No. | Rate kg/ha | Sobe | Cotz | Rape | Cobu | Wibw | Mogl | Hesc | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| | Herbicide Secondary Pre, spectrums 26, 88, 91, 93, 95, 96, and 100 (C = 100% control) | | | | | | | | | | | | | | | | | | | | | | |
| 2 | 5.6050 | 0 | — | — | 0 | 0 | 0 | 0 | — | 0 | 0 | 0 | 0 | — | 0 | 0 | 1 | 0 | — | 0 | 0 | 0 | — |
| | 1.1210 | 0 | — | — | 0 | 0 | 0 | 0 | — | 0 | 0 | 0 | 0 | — | 0 | 0 | 0 | 0 | — | 0 | 0 | 0 | — |
| 3 | 5.6050 | 0 | — | — | 0 | 0 | 0 | 0 | — | 0 | 0 | 0 | 0 | 0 | 0 | 1 | 1 | 3 | 0 | 0 | 3 | 3 | — |
| | 1.1210 | 0 | — | — | 0 | 0 | 0 | 0 | — | 0 | 0 | 0 | 0 | 0 | 0 | 0 | 0 | 3 | 0 | 0 | 1 | 2 | — |
| | 0.5605 | 0 | — | — | 0 | 0 | 0 | 0 | — | 0 | 0 | 0 | 0 | 0 | 0 | 0 | 0 | 3 | 0 | 0 | 0 | 1 | — |
| | 0.2803 | 0 | — | — | 0 | 0 | 0 | 0 | — | 0 | 0 | 0 | 0 | 0 | 0 | 0 | 0 | 0 | 0 | 0 | 0 | 0 | — |
| 4 | 4.6050 | 3 | — | — | 1 | 2 | 3 | 3 | — | 3 | 3 | 3 | 3 | 3 | 3 | 3 | 3 | 3 | 3 | 3 | 3 | 3 | — |
| | 1.1210 | 2 | — | — | 0 | 0 | 0 | 0 | — | 0 | 3 | 1 | 3 | 0 | 3 | 3 | 3 | 3 | 3 | 1 | 2 | 3 | — |
| | 0.5605 | N | — | — | N | 0 | 2 | 0 | — | 0 | 0 | 1 | 2 | 0 | 0 | 2 | 2 | 1 | 3 | 0 | 3 | 3 | — |
| | 0.2803 | 0 | — | — | 1 | N | 0 | 0 | — | 0 | 0 | 0 | 0 | 0 | 2 | 0 | 0 | 2 | 1 | 0 | N | N | — |
| | 0.1401 | 0 | — | — | 0 | 2 | 0 | 0 | — | 0 | 0 | 0 | 0 | 0 | 0 | 0 | 1 | 0 | N | 0 | 2 | 2 | — |
| | 0.0701 | 0 | — | — | 0 | N | 0 | N | — | 0 | 0 | 1 | 0 | 0 | 1 | 0 | 0 | N | 0 | N | N | N | — |
| | 0.0350 | 0 | — | — | 0 | N | 0 | 1 | — | 0 | 0 | 0 | 0 | 0 | 1 | 0 | 0 | 1 | 0 | 1 | N | 2 | — |
| | 0.0175 | 0 | — | — | 0 | N | 0 | 1 | — | 0 | 0 | 0 | 0 | 0 | 1 | 0 | 0 | 1 | 0 | 1 | N | N | — |
| | 0.0087 | 0 | — | — | 1 | N | 0 | N | — | 0 | 0 | 1 | 0 | 0 | 0 | 0 | 2 | 0 | N | 0 | N | 2 | — |
| 5 | 5.6050 | 3 | — | — | 1 | 3 | 3 | 3 | — | 3 | 3 | 3 | 3 | — | 3 | 3 | 3 | 3 | — | 3 | 3 | 3 | — |
| | 1.1210 | 1 | — | — | 0 | 2 | 2 | 2 | — | 1 | 1 | 3 | 3 | — | 0 | 3 | 3 | 3 | — | 3 | 3 | 2 | — |
| | 0.2803 | 0 | — | — | 0 | 1 | 2 | 1 | — | 0 | 0 | 1 | 2 | — | 0 | 2 | 3 | 3 | — | 3 | 3 | 2 | — |
| | 0.0561 | 0 | — | — | 0 | 0 | 0 | 0 | — | 0 | 0 | 0 | 0 | — | 0 | 0 | 0 | 0 | — | 0 | 0 | 0 | — |
| 6 | 5.6050 | 0 | — | — | 0 | 3 | 2 | 1 | — | 1 | 1 | 1 | 2 | — | 2 | 3 | 2 | 3 | — | 1 | 2 | 1 | — |
| | 1.1210 | 0 | — | — | 0 | 0 | 0 | 0 | — | 0 | 0 | 1 | 0 | — | 0 | 2 | 2 | 1 | — | 0 | 2 | 1 | — |
| | 0.2803 | 0 | — | — | 0 | 0 | 0 | 0 | — | 0 | 0 | 0 | 0 | — | 0 | 0 | 0 | 0 | — | 0 | 2 | 0 | — |
| | 0.0561 | 0 | — | — | 0 | 0 | 0 | 0 | — | 0 | 0 | 0 | 0 | — | 0 | 0 | 0 | 0 | — | 0 | 0 | 0 | — |
| | 0.0112 | 0 | — | — | 0 | 0 | 0 | 0 | — | 0 | 0 | 0 | 0 | — | 0 | 0 | 0 | 0 | — | 0 | 0 | 0 | — |
| 7 | 5.6050 | 2 | — | — | 0 | 3 | 2 | 2 | — | 2 | 3 | 3 | 3 | 3 | 3 | 3 | 3 | 3 | 3 | 2 | 3 | 3 | — |
| | 1.1210 | 0 | — | — | 0 | 2 | 1 | 0 | — | 0 | 0 | 3 | 2 | 0 | 3 | 3 | 2 | 3 | 3 | 0 | 1 | 0 | — |
| | 0.5605 | 0 | — | — | 0 | 1 | 0 | 0 | — | 0 | 0 | 0 | 1 | 0 | 2 | 2 | 3 | 3 | 3 | 0 | 0 | 1 | — |
| | 0.2803 | 0 | — | — | 0 | 2 | 0 | 0 | — | 0 | 0 | 0 | 0 | 0 | 0 | 1 | 0 | 3 | 1 | 0 | 0 | 1 | — |
| | 0.1401 | 0 | — | — | 0 | 0 | 0 | 0 | — | 0 | 0 | 0 | 0 | 0 | 0 | 1 | 0 | 3 | 0 | 0 | 0 | 0 | — |
| | 0.0701 | N | — | — | 0 | 0 | 0 | 0 | — | 0 | 0 | 0 | 0 | 0 | 0 | 0 | 0 | 0 | 0 | 0 | 0 | 1 | — |
| | 0.0350 | 0 | — | — | 0 | 0 | 0 | 0 | — | 0 | 0 | 0 | 0 | 0 | 0 | 0 | 0 | 0 | 0 | 0 | 0 | 0 | — |
| | 0.0175 | 0 | — | — | 0 | 0 | 0 | 0 | — | 0 | 0 | 0 | 0 | 0 | 0 | 0 | 0 | 0 | 0 | 0 | 0 | 0 | — |
| 8 ) | 5.6050 | 3 | 1 | 3 | 1 | 3 | 3 | 3 | 3 | 3 | 3 | 3 | 3 | 3 | 3 | 3 | 3 | 3 | 3 | — | — | — | — |
| | 5.6050 | 3 | 2 | 3 | 2 | 3 | 3 | 3 | 3 | 3 | 3 | 3 | 3 | 3 | 3 | 3 | 3 | 3 | 3 | — | — | — | — |
| | 1.1210 | 1 | 1 | 3 | 1 | 3 | 1 | 1 | 1 | 2 | 3 | 3 | 3 | 2 | 3 | 3 | 3 | 3 | 3 | — | — | — | — |
| ) | 1.1210 | 3 | 2 | 2 | 0 | 2 | 3 | 3 | 3 | 1 | 2 | 3 | 3 | 3 | 3 | 3 | 3 | 3 | 3 | — | — | — | — |
| ) | 0.5605 | 3 | 2 | 0 | 1 | 3 | 2 | 2 | 3 | 2 | 1 | 3 | 3 | 2 | 3 | 3 | 3 | 3 | 3 | — | — | — | — |
| ) | 0.2803 | 1 | N | 0 | 0 | 1 | 1 | 2 | 0 | 1 | 0 | 3 | 3 | 0 | 1 | 3 | 3 | 2 | 3 | — | — | — | — |
| | 0.2803 | 0 | 0 | 0 | 1 | 0 | 0 | 0 | 1 | 0 | 0 | 1 | 3 | 0 | 3 | 3 | 3 | 3 | 2 | — | — | — | — |
| ) | 0.1401 | 0 | 3 | 0 | 0 | 0 | 0 | 2 | 1 | 1 | 0 | 3 | 3 | 0 | 1 | 1 | 1 | 2 | 1 | — | — | — | — |
| ) | 0.0701 | N | 0 | 0 | 0 | N | N | 0 | 0 | 0 | 0 | 0 | 3 | 0 | 0 | 0 | 0 | N | 0 | — | — | — | — |
| | 0.0701 | 0 | 0 | 0 | 1 | 0 | 0 | 0 | 0 | 0 | 0 | 0 | 0 | 0 | 0 | 0 | 0 | 0 | 0 | — | — | — | — |
| 9 | 5.6050 | 3 | — | — | 0 | 3 | 3 | 3 | — | 3 | 3 | 3 | 3 | 3 | 3 | 3 | 3 | 3 | 3 | 3 | 3 | 3 | — |
| | 1.1210 | 3 | — | — | 0 | 3 | 2 | 1 | — | 2 | 3 | 3 | 3 | 2 | 3 | 3 | 3 | 3 | 3 | 3 | 3 | 3 | — |
| | 0.5605 | 2 | — | — | 0 | 2 | N | 0 | — | 1 | 2 | 3 | 3 | 1 | 3 | 3 | 3 | 3 | 3 | 1 | 0 | 1 | — |
| | 0.2803 | 1 | — | — | 0 | 0 | 2 | N | — | 1 | 0 | 3 | 3 | 0 | 2 | 3 | 3 | 3 | 3 | 3 | 0 | 3 | — |
| | 0.1401 | 0 | — | — | 0 | 0 | 0 | 0 | — | 0 | 0 | 3 | 3 | 0 | 0 | 3 | 3 | 3 | 3 | 1 | 0 | 1 | — |
| | 0.0701 | 0 | — | — | N | 0 | N | 0 | — | 0 | 0 | 3 | 1 | 0 | 1 | 3 | 2 | 3 | 3 | 0 | 0 | 0 | — |
| | 0.0350 | N | — | — | 0 | 1 | 0 | 0 | — | 0 | 0 | 1 | 0 | 0 | 0 | 3 | 0 | 3 | 0 | 1 | N | N | — |
| | 0.0175 | 0 | — | — | 0 | 1 | 0 | 0 | — | 0 | 0 | 0 | 0 | 0 | 0 | 0 | N | 3 | 1 | 0 | 0 | 0 | — |

TABLE B-continued

| | | | | | | | | | | | | | | | | | | | | | | | |
|---|---|---|---|---|---|---|---|---|---|---|---|---|---|---|---|---|---|---|---|---|---|---|---|
| | 0.0087 | 0 | — | — | 0 | 0 | 0 | 0 | — | 0 | 0 | 0 | 0 | 0 | 0 | 0 | 0 | 0 | 1 | 0 | 0 | 0 | — |
| | 0.0044 | 0 | — | — | 0 | 0 | 0 | 0 | — | 0 | 0 | 0 | 0 | 0 | 0 | 0 | 0 | 0 | 0 | 0 | 0 | 0 | — |
| 10 | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | 1.1210 | 3 | — | — | 3 | 2 | 3 | 3 | — | 2 | 3 | 3 | 3 | 3 | 3 | 3 | 3 | 3 | 3 | 3 | N | 3 | — |
| | 0.5605 | 2 | — | — | 2 | 2 | 2 | 2 | — | 2 | 3 | 3 | 3 | 3 | 3 | 3 | 3 | 3 | 3 | 3 | 3 | 3 | — |
| | 0.2803 | 1 | — | — | 3 | N | 2 | 1 | — | 0 | 2 | 3 | 3 | 3 | 3 | 3 | 3 | 3 | 3 | 3 | 3 | 3 | — |
| | 0.1401 | 1 | — | — | 1 | 1 | 0 | 0 | — | 0 | 2 | 3 | 3 | 1 | 3 | 3 | 3 | 3 | 3 | 2 | 3 | 3 | — |
| | 0.0701 | N | — | — | N | 2 | N | 1 | — | 0 | 0 | 3 | 2 | 1 | 0 | 3 | 3 | 3 | 3 | 2 | 3 | 2 | — |
| | 0.0350 | 0 | — | — | 2 | 2 | 0 | 0 | — | 0 | 0 | 1 | 1 | 0 | 0 | 0 | 1 | 3 | 3 | 1 | 3 | 1 | — |
| | 0.0175 | 0 | — | — | N | 0 | N | 0 | — | 0 | 0 | 0 | 1 | 0 | 0 | 1 | 1 | 3 | 3 | 1 | 1 | 1 | — |
| | 0.0087 | N | — | — | N | 1 | 0 | 0 | — | 0 | 0 | 0 | 1 | 0 | 0 | 0 | 0 | 2 | 3 | 0 | 2 | 0 | — |
| 11 | 5.6050 | 2 | — | — | 1 | 3 | 2 | 3 | — | 3 | 3 | 3 | 3 | 2 | 3 | 3 | 3 | 3 | 3 | 3 | 3 | 3 | — |
| | 1.1210 | N | — | — | N | 3 | N | 1 | — | 0 | 2 | 3 | 3 | 3 | 3 | 3 | 3 | 3 | 3 | 3 | 3 | 3 | — |
| | 0.5605 | 2 | — | — | 1 | 1 | 2 | 0 | — | 0 | 3 | 3 | 3 | 2 | 3 | 3 | 3 | 3 | 3 | 3 | 3 | 3 | — |
| | 0.2803 | N | — | — | 1 | 2 | N | 1 | — | 0 | 0 | 3 | 3 | 2 | 1 | 3 | 3 | 2 | 3 | 3 | 2 | 3 | — |
| | 0.1401 | 1 | — | — | N | 1 | 0 | 0 | — | 0 | N | 3 | N | 1 | 1 | 2 | N | 3 | N | 0 | 2 | 2 | — |
| | 0.0701 | 1 | — | — | 0 | 0 | 1 | 0 | — | 0 | 0 | 2 | 2 | 0 | 0 | 3 | 3 | 3 | 3 | 0 | 2 | 3 | — |
| | 0.0350 | 0 | — | — | 0 | 0 | 0 | 0 | — | 0 | 1 | 0 | 1 | 0 | 0 | 0 | 0 | 0 | 1 | 0 | 2 | 1 | — |
| | 0.0175 | 0 | — | — | N | N | 0 | N | — | N | 0 | 0 | 0 | 0 | N | 0 | 0 | N | 0 | N | N | N | — |
| | 0.0087 | 0 | — | — | 0 | 1 | 0 | 0 | — | 0 | 0 | 0 | 0 | 0 | 0 | 0 | 0 | 0 | 0 | 0 | 1 | 1 | — |
| 12 + | 5.6050 | 0 | — | — | 0 | 3 | 3 | 3 | — | 0 | 1 | 3 | 3 | 3 | 3 | 3 | 3 | 3 | 3 | 3 | 3 | N | — |
| + | 1.1210 | 0 | — | — | N | 1 | 2 | 0 | — | 0 | 0 | 3 | 3 | 1 | 0 | 3 | 3 | 3 | 3 | 0 | 3 | N | — |
| + | 0.5605 | 1 | — | — | N | 1 | 1 | 0 | — | 0 | 0 | 3 | 1 | 0 | 0 | 3 | 3 | 3 | 3 | 0 | 1 | N | — |
| + | 0.2803 | 0 | — | — | 1 | 0 | 1 | 0 | — | 0 | 0 | 3 | 1 | 0 | 0 | 2 | 0 | 3 | 3 | 0 | 1 | N | — |
| + | 0.1401 | 0 | — | — | N | 1 | N | 1 | — | 0 | 0 | 1 | 0 | 0 | 0 | 0 | 0 | 3 | 3 | 1 | 1 | N | — |
| + | 0.0701 | 0 | — | — | N | 1 | N | 0 | — | 0 | 0 | 0 | 0 | 0 | 0 | 0 | 0 | 1 | 1 | 0 | 1 | N | — |
| 13 | 5.6050 | 2 | 1 | 3 | 0 | 3 | 3 | 3 | 3 | 3 | 3 | 3 | 3 | 3 | 3 | 3 | 3 | 3 | 3 | — | — | — | — |
| | 1.1210 | 1 | 1 | 1 | 0 | 3 | 3 | 3 | 3 | 3 | 3 | 3 | 3 | 3 | 3 | 3 | 3 | 3 | 3 | — | — | — | — |
| | 0.5605 | 2 | 1 | 1 | 0 | 3 | 2 | 0 | 3 | 0 | 3 | 3 | 3 | 3 | 3 | 3 | 3 | 3 | 3 | — | — | — | — |
| | 0.2803 | 0 | 1 | 0 | 0 | 0 | 0 | 1 | 2 | 0 | 0 | 3 | 3 | 1 | 0 | 1 | 3 | 3 | 3 | — | — | — | — |
| | 0.1401 | 0 | 1 | 0 | 0 | 0 | 0 | 1 | 1 | 0 | 1 | 1 | 2 | 0 | 0 | 1 | 1 | 0 | 1 | — | — | — | — |
| | 0.0701 | 0 | 1 | 0 | N | 1 | 0 | N | 2 | 1 | 0 | 2 | 1 | 1 | 0 | 0 | 0 | 0 | 0 | — | — | — | — |
| 14 | 5.6050 | 2 | 1 | 3 | 0 | 3 | 2 | 3 | 3 | 2 | 3 | 3 | 3 | 2 | 3 | 3 | 3 | 3 | 3 | — | — | — | — |
| | 1.1210 | 1 | 1 | 2 | 0 | 2 | 3 | 1 | 3 | 2 | 3 | 3 | 3 | 3 | 3 | 3 | 3 | 3 | 3 | — | — | — | — |
| | 0.5605 | 2 | 0 | 2 | N | 3 | 2 | 1 | 3 | 0 | 2 | 3 | 3 | 1 | 3 | 3 | 3 | 3 | 3 | — | — | — | — |
| | 0.2803 | 0 | N | 1 | 0 | 1 | 1 | 1 | 1 | 0 | 0 | 3 | 2 | 0 | 1 | 3 | 3 | 3 | 3 | — | — | — | — |
| | 0.1401 | 1 | 0 | 0 | N | 1 | 0 | 0 | 0 | 0 | 1 | 2 | 1 | 0 | 0 | 0 | 0 | 0 | 0 | — | — | — | — |
| | 0.0701 | N | 0 | 0 | 0 | 0 | 0 | 0 | 0 | 0 | 0 | 0 | 1 | 0 | 0 | 0 | 0 | 0 | 0 | — | — | — | — |
| | 0.0351 | 0 | 0 | 0 | 0 | 0 | 0 | 0 | 0 | 0 | 0 | 0 | 0 | 0 | 0 | 0 | 0 | 0 | 0 | — | — | — | — |
| | 0.0175 | 0 | 0 | 0 | 0 | 1 | 0 | 0 | 0 | 0 | 0 | 0 | 0 | 0 | 0 | 0 | 0 | 0 | 0 | — | — | — | — |
| | 0.0087 | 0 | 1 | 0 | 1 | 0 | 0 | 1 | 1 | 0 | 0 | 0 | 1 | 0 | 0 | 0 | 0 | 0 | 0 | — | — | — | — |
| 15 ) | 5.6050 | 3 | 0 | 3 | 0 | 3 | 3 | 3 | 3 | 3 | 3 | 3 | 3 | 3 | 3 | 3 | 3 | 3 | 3 | — | — | — | — |
| ) | 1.1210 | 3 | 1 | 3 | N | 3 | 3 | 3 | 3 | 3 | 3 | 3 | 3 | 3 | 3 | 3 | 3 | 3 | 3 | — | — | — | — |
| ) | 0.5605 | 3 | 1 | 2 | 0 | 1 | 2 | 3 | 1 | 3 | 2 | 3 | 3 | 3 | 3 | 3 | 3 | 3 | 3 | — | — | — | — |
| ) | 0.2803 | 2 | 0 | 1 | 0 | 1 | 3 | 1 | 2 | 1 | 1 | 3 | 3 | 1 | 3 | 3 | 3 | 3 | 3 | — | — | — | — |
| ) | 0.1401 | 1 | 1 | 0 | N | 0 | 0 | 0 | 0 | 0 | 1 | 3 | 3 | 0 | 3 | 3 | 3 | 3 | 3 | — | — | — | — |
| ) | 0.0701 | 0 | 2 | 0 | 0 | 0 | 0 | 0 | 0 | 0 | 0 | 3 | 3 | 0 | 3 | 1 | 3 | 3 | 3 | — | — | — | — |
| ) | 0.0351 | N | N | 0 | N | N | 1 | N | 0 | N | N | 3 | 3 | 1 | 3 | N | 1 | 3 | 1 | — | — | — | — |
| ) | 0.0175 | 0 | 0 | 0 | 0 | 0 | 0 | 1 | 0 | 1 | 0 | 1 | 2 | 0 | 2 | 0 | 0 | 3 | 0 | — | — | — | — |
| 16 / | 5.6050 | 3 | 1 | 3 | 0 | 3 | 3 | 3 | 3 | 3 | 3 | 3 | 3 | 3 | 3 | 3 | 3 | 3 | 3 | — | — | — | — |
| | 5.6050 | 3 | 0 | 3 | 0 | 3 | 3 | 3 | 3 | 3 | 3 | 3 | 3 | 3 | 3 | 3 | 3 | 3 | 3 | — | — | — | — |
| / | 1.1210 | 1 | 0 | 1 | 0 | 3 | 2 | 1 | 2 | 2 | 3 | 3 | 3 | 3 | 3 | 3 | 3 | 3 | 3 | — | — | — | — |
| | 1.1210 | 3 | 0 | 3 | 1 | 3 | 2 | 2 | 2 | 3 | 2 | 3 | 2 | 2 | 3 | 3 | 3 | 3 | 3 | — | — | — | — |

TABLE B-continued

| | | | | | | | | | | | | | | | | | | | | | | | |
|---|---|---|---|---|---|---|---|---|---|---|---|---|---|---|---|---|---|---|---|---|---|---|---|
| / | 0.2803 | 1 | 0 | 0 | N | 0 | 0 | 0 | 1 | 0 | 2 | 3 | 2 | 3 | 3 | 3 | 3 | 3 | 3 | — | — | — | — |
| | 0.2803 | 0 | 0 | 2 | 0 | 1 | 0 | 0 | 1 | 1 | 1 | 3 | 2 | 0 | 3 | 3 | 3 | 3 | 3 | — | — | — | — |
| / | 0.0701 | 0 | 0 | 0 | 0 | 0 | 0 | 1 | 0 | 0 | 0 | 0 | 0 | 0 | 0 | 1 | 0 | 3 | 1 | — | — | — | — |
| | 0.0701 | 0 | 0 | 1 | N | 0 | 0 | 0 | 0 | 0 | 0 | 0 | 0 | 0 | 2 | 0 | 1 | 3 | 1 | — | — | — | — |
| | 0.0175 | 1 | 0 | 0 | 0 | 0 | 0 | 0 | 0 | 0 | 0 | 0 | 0 | N | 0 | 0 | 0 | 1 | 1 | — | — | — | — |
| / | 0.0175 | 0 | 0 | 0 | N | 0 | 0 | 0 | 0 | 0 | 0 | 0 | 0 | 0 | 0 | 0 | 0 | 0 | 0 | — | — | — | — |
| 17 | 5.6050 | 3 | 0 | 3 | 1 | 3 | 3 | 3 | 3 | 3 | 3 | 3 | 3 | 3 | 3 | 3 | 3 | 3 | 3 | — | — | — | — |
| | 1.1210 | 3 | N | 3 | 1 | 3 | 3 | 2 | 3 | 3 | 3 | 3 | 3 | 3 | 3 | 3 | 3 | 3 | 3 | — | — | — | — |
| | 0.2803 | 0 | N | 1 | 0 | 3 | 0 | 0 | 2 | 0 | 1 | 3 | 2 | 1 | 3 | 3 | 3 | 3 | 3 | — | — | — | — |
| | 0.0701 | 0 | 1 | 0 | 0 | 1 | 0 | 0 | 0 | 0 | 0 | 1 | 1 | 1 | 1 | 1 | 3 | 3 | 3 | — | — | — | — |
| | 0.0175 | 0 | 1 | 0 | 0 | 0 | 0 | 0 | 0 | 0 | 0 | 0 | 0 | 0 | 0 | 0 | 0 | 3 | 1 | — | — | — | — |
| | 0.0087 | 0 | 1 | 0 | 0 | 0 | 0 | 0 | 0 | 0 | 0 | 1 | 1 | 1 | 0 | 0 | 0 | 1 | 0 | — | — | — | — |
| 18 ~ | 5.6050 | 1 | 0 | 3 | N | 3 | 3 | 3 | 3 | 3 | 3 | 3 | 3 | 1 | 3 | 3 | 3 | 3 | 3 | — | — | — | — |
| ~ | 1.1210 | 0 | 1 | 1 | N | 3 | 2 | 0 | 1 | 1 | 1 | 3 | 2 | 0 | 1 | 3 | 2 | 3 | 3 | — | — | — | — |
| ~ | 0.2803 | 0 | 0 | 0 | N | 0 | 0 | 1 | 0 | N | 0 | 3 | N | 0 | 0 | 0 | 3 | 3 | 3 | — | — | — | — |
| ~ | 0.0701 | 0 | 1 | 0 | N | 0 | 0 | 0 | 1 | 0 | 0 | 1 | 0 | 0 | 0 | 0 | 0 | 0 | 0 | — | — | — | — |
| 19 | 5.6050 | 3 | — | — | 2 | 2 | 1 | 3 | — | 3 | 3 | 3 | 3 | 3 | 3 | 3 | 3 | 3 | 3 | 3 | 3 | 3 | — |
| | 1.1210 | 1 | — | — | 2 | 1 | 1 | 0 | — | 0 | 0 | 3 | 3 | 0 | 2 | 3 | 3 | 3 | 3 | 3 | 3 | 3 | — |
| | 0.5605 | 1 | — | — | 1 | 0 | N | 0 | — | 0 | 0 | 3 | 3 | 0 | 0 | 2 | 1 | 3 | 3 | 1 | 1 | 2 | — |
| | 0.2803 | 0 | — | — | 0 | 1 | 0 | 0 | — | 0 | 0 | 3 | 0 | 0 | 2 | 3 | 0 | 3 | 1 | 2 | 3 | 1 | — |
| | 0.1401 | N | — | — | 0 | 0 | 0 | 0 | — | 0 | 0 | 0 | 0 | 0 | 0 | N | 0 | 2 | 1 | 0 | 0 | 0 | — |
| | 0.0701 | 0 | — | — | 0 | 0 | N | 0 | — | 0 | 0 | 0 | 0 | 0 | 0 | 3 | 0 | 3 | 0 | 0 | 0 | 1 | — |
| | 0.0350 | 0 | — | — | 0 | 0 | 1 | 0 | — | 0 | 0 | 1 | 0 | 0 | 0 | 1 | 0 | 3 | 0 | 1 | 0 | 0 | — |
| | 0.0175 | 0 | — | — | 0 | 0 | 0 | 0 | — | 0 | 0 | 0 | 0 | 0 | 0 | 0 | 0 | 0 | 0 | 0 | 0 | 1 | — |
| | 0.0087 | 0 | — | — | 0 | N | 1 | 0 | — | 0 | 0 | 1 | 0 | 0 | 0 | 0 | 0 | 0 | 0 | N | N | N | — |
| 20 | 5.6050 | 1 | — | — | 0 | 3 | 3 | 3 | — | 3 | 2 | 2 | 3 | 1 | 3 | 3 | 3 | 3 | 3 | 2 | 3 | 3 | — |
| | 1.1210 | 0 | — | — | 0 | 1 | 0 | 1 | — | 0 | 0 | 0 | 3 | 0 | 0 | 2 | 3 | 2 | 2 | 0 | 3 | 1 | — |
| | 0.5605 | 0 | — | — | 0 | 0 | 0 | 0 | — | 0 | 0 | 0 | 0 | 0 | 0 | 3 | 2 | 0 | 0 | 0 | 0 | 1 | — |
| | 0.2803 | 0 | — | — | 0 | 0 | 0 | 0 | — | 0 | 0 | 0 | 0 | 0 | 0 | 0 | 0 | 0 | 0 | 0 | 1 | 0 | — |
| | 0.1401 | 0 | — | — | 0 | 0 | 0 | 0 | — | 0 | 0 | 0 | 0 | 0 | 0 | 0 | 0 | 0 | 0 | 0 | N | 0 | — |
| | 0.0701 | 0 | — | — | 0 | 0 | 0 | 0 | — | 0 | 0 | 0 | 0 | 0 | 0 | 0 | 0 | 0 | 0 | 0 | 0 | 0 | — |
| | 0.0350 | 0 | — | — | 0 | 0 | 0 | 0 | — | 0 | 0 | 0 | 0 | 0 | 0 | 1 | 0 | 1 | 0 | 0 | 0 | 0 | — |
| 21 B | 5.6050 | 3 | 1 | 3 | 0 | 3 | 3 | 2 | 1 | 3 | 3 | 3 | 3 | 3 | 3 | 3 | 3 | 3 | 3 | — | — | — | — |
| B | 1.1210 | 2 | 0 | 1 | 1 | 3 | 0 | 1 | 2 | 1 | 1 | 3 | 3 | 1 | 3 | 3 | 3 | 3 | 3 | — | — | — | — |
| B | 0.2803 | 0 | N | 0 | 0 | 2 | 0 | 0 | 1 | 0 | 0 | 2 | 1 | N | 1 | 0 | 0 | 3 | 0 | — | — | — | — |
| B | 0.0701 | 0 | 0 | 0 | 0 | 1 | 0 | 0 | 0 | 0 | 0 | 0 | 0 | 0 | 0 | 0 | 0 | 0 | 0 | — | — | — | — |
| 22 { | 5.6050 | 3 | 1 | 3 | N | 3 | 3 | 3 | 3 | 3 | 3 | 3 | 3 | 3 | 3 | 3 | 3 | 3 | 3 | — | — | — | — |
| { | 1.1210 | 1 | 2 | 2 | N | 3 | 0 | 1 | 3 | 1 | 2 | 3 | 3 | 2 | 3 | 3 | 3 | 3 | 3 | — | — | — | — |
| { | 0.2803 | 1 | 1 | 0 | N | 0 | 0 | 0 | 1 | 0 | 0 | 1 | 2 | 0 | 1 | 3 | 3 | 3 | 2 | — | — | — | — |
| { | 0.0701 | 0 | 0 | 0 | N | 0 | 0 | 0 | 0 | 0 | 0 | 0 | 0 | 1 | 0 | 0 | 0 | 1 | 0 | — | — | — | — |
| { | 0.0175 | 0 | N | 0 | N | 0 | 0 | 0 | 0 | 0 | 0 | 0 | 0 | 0 | 0 | 0 | 0 | 0 | 0 | — | — | — | — |
| { | 0.0087 | 0 | 0 | 0 | N | 0 | 0 | 0 | 0 | 0 | 0 | 0 | N | N | 0 | 0 | N | 0 | 0 | — | — | — | — |
| 23 . | 5.6050 | 3 | 0 | 3 | 3 | 3 | 3 | 3 | 3 | 3 | 3 | 3 | 3 | 3 | 3 | 3 | 3 | 3 | 3 | — | — | — | — |
| . | 1.1210 | 2 | 0 | 2 | 3 | 3 | 3 | 2 | 2 | 2 | 2 | 3 | 3 | 3 | 3 | 3 | 3 | 3 | 3 | — | — | — | — |
| . | 0.2803 | 0 | 1 | 0 | N | 1 | 0 | 1 | 1 | 0 | 0 | 1 | 0 | 0 | 1 | 1 | 2 | 3 | 2 | — | — | — | — |
| . | 0.0701 | 0 | 0 | 0 | N | 0 | 0 | 0 | 0 | 0 | 0 | 1 | 0 | 1 | 0 | 0 | 0 | 3 | 0 | — | — | — | — |
| . | 0.0175 | 0 | 0 | 0 | N | 0 | 0 | 0 | 0 | 0 | 0 | 0 | 0 | 0 | 0 | 0 | 0 | 1 | 1 | — | — | — | — |
| . | 0.0087 | N | 0 | 0 | 1 | 0 | 0 | 0 | 0 | 0 | 0 | 0 | 0 | 0 | 0 | 0 | 0 | 1 | 0 | — | — | — | — |
| 24 M | 5.6050 | 3 | — | — | 0 | 2 | 0 | 3 | — | 3 | 3 | 3 | 3 | 3 | 3 | 3 | 3 | 3 | 3 | 2 | 3 | 3 | — |
| M | 1.1210 | 0 | — | — | 1 | 0 | 1 | 3 | — | 3 | 1 | 3 | 3 | 3 | 3 | 3 | 3 | 3 | 3 | 3 | 3 | 2 | — |
| M | 0.5605 | 0 | — | — | 1 | 0 | N | 2 | — | 1 | 1 | 3 | 3 | 3 | 2 | 3 | 3 | 3 | 3 | 2 | 1 | 2 | — |
| M | 0.2803 | 0 | — | — | N | 0 | N | 3 | — | 2 | 0 | 2 | 3 | 0 | 0 | 3 | 3 | 3 | 3 | N | 3 | 2 | — |
| M | 0.1401 | 0 | — | — | N | 0 | N | 1 | — | 0 | 0 | 1 | 2 | 0 | 0 | 3 | 3 | 3 | 3 | 0 | 0 | 1 | — |

TABLE B-continued

| | | | | | | | | | | | | | | | | | | | | | | | |
|---|---|---|---|---|---|---|---|---|---|---|---|---|---|---|---|---|---|---|---|---|---|---|---|
| M | 0.0701 | 0 | — | — | N | 0 | N | 0 | — | 0 | 0 | 1 | 0 | 0 | 0 | 3 | 2 | 2 | 1 | 0 | 1 | 1 | — |
| M | 0.0350 | 0 | — | — | N | 0 | 1 | 1 | — | 0 | 0 | 0 | 0 | 0 | 0 | 0 | 0 | 1 | 0 | 1 | 0 | 2 | — |
| M | 0.0175 | 0 | — | — | N | 0 | N | 0 | — | 0 | 0 | 0 | 1 | 0 | 0 | 0 | 0 | 0 | 0 | 0 | 0 | N | — |
| 25 | 5.6050 | 2 | — | — | 2 | 3 | 3 | 3 | — | 3 | 3 | 3 | 3 | 3 | 3 | 3 | 3 | 3 | 3 | 3 | 3 | 3 | — |
| | 1.1210 | 1 | — | — | 0 | 3 | 3 | 3 | — | 3 | 2 | 3 | 3 | 1 | 3 | 3 | 3 | 3 | 3 | 3 | 3 | 3 | — |
| | 0.5605 | 0 | — | — | 1 | 3 | 1 | 1 | — | 2 | 0 | 3 | 3 | 0 | 3 | 3 | 3 | 3 | 3 | 3 | 3 | 2 | — |
| | 0.2803 | 0 | — | — | 0 | 0 | 1 | 0 | — | 0 | N | 3 | 2 | 0 | 2 | 0 | 3 | 3 | 1 | 0 | 0 | 0 | — |
| | 0.1401 | 0 | — | — | 0 | 1 | 0 | 0 | — | 0 | 0 | 3 | 1 | N | 0 | 0 | 0 | 3 | 0 | 0 | 1 | 0 | — |
| | 0.0701 | 0 | — | — | 0 | 0 | 0 | 0 | — | 0 | 0 | 0 | 0 | 0 | 0 | 0 | 0 | 0 | 0 | 0 | 0 | 0 | — |
| | 0.0350 | N | — | — | 0 | 0 | 0 | 0 | — | 0 | 0 | 0 | 0 | 0 | 0 | 0 | 0 | 0 | 0 | N | 0 | 1 | — |
| | 0.0175 | 0 | — | — | 0 | 0 | 0 | 0 | — | 0 | 0 | 0 | 0 | 0 | 0 | 0 | 0 | 0 | 0 | 0 | 0 | 0 | — |
| | 0.0087 | N | — | — | 0 | 1 | 0 | 0 | — | 0 | 0 | 0 | N | 0 | 0 | 0 | 0 | N | 0 | 0 | 1 | 0 | — |
| | 0.0044 | 0 | — | — | 0 | 0 | 0 | 0 | — | 0 | 0 | 0 | 0 | 0 | 0 | 0 | 0 | 0 | 0 | 0 | 0 | 0 | — |
| 26 | 5.6050 | 3 | — | — | 0 | 3 | 3 | 3 | — | 3 | 3 | 3 | 3 | 3 | 3 | 3 | 3 | 3 | 3 | 3 | 3 | 3 | — |
| | 1.1210 | 2 | — | — | 0 | 2 | 3 | 2 | — | 1 | 3 | 3 | 3 | 3 | 3 | 3 | 3 | 3 | 3 | 3 | 3 | 3 | — |
| | 0.5605 | 1 | — | — | 0 | 2 | 2 | 3 | — | 1 | 3 | 3 | 3 | 3 | 3 | 3 | 3 | 3 | 3 | 3 | 3 | 3 | — |
| | 0.2803 | 0 | — | — | 0 | 1 | 1 | 0 | — | 1 | 3 | 2 | 3 | 2 | 3 | 3 | 3 | 3 | 3 | 1 | 3 | 0 | — |
| | 0.1401 | 0 | — | — | 1 | 0 | 0 | 0 | — | 0 | 0 | 0 | 3 | 0 | 1 | 0 | 3 | 0 | 3 | 0 | 0 | 0 | — |
| | 0.0701 | 0 | — | — | 0 | 0 | 0 | 0 | — | 0 | N | 0 | 3 | 0 | 1 | 0 | 3 | 1 | 3 | 0 | 0 | 0 | — |
| | 0.0350 | 0 | — | — | 0 | 0 | 0 | 0 | — | 0 | 0 | 0 | 1 | 0 | 0 | 0 | 2 | 0 | 1 | 0 | 0 | 0 | — |
| | 0.0175 | 0 | — | — | 0 | 0 | 0 | 0 | — | 0 | 0 | 0 | 0 | 0 | 0 | 0 | 0 | N | 0 | 0 | 0 | N | — |
| | 0.0087 | 0 | — | — | 0 | N | 0 | N | — | N | 0 | N | 0 | 0 | N | N | 0 | N | 0 | N | N | N | — |
| 27 | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | 1.1210 | 3 | — | — | 2 | 3 | 3 | 3 | — | 3 | 3 | 3 | 3 | 3 | 3 | 3 | 3 | 3 | 3 | 3 | 3 | 3 | — |
| | 0.5605 | 2 | — | — | 0 | 3 | 3 | 3 | — | 3 | 3 | 3 | 3 | 3 | 3 | 3 | 3 | 3 | 3 | 3 | 3 | 3 | — |
| | 0.2803 | 3 | — | — | 0 | 3 | 3 | 2 | — | 2 | 3 | 3 | 3 | 3 | 3 | 3 | 3 | 3 | 3 | 2 | 3 | 3 | — |
| | 0.1401 | 1 | — | — | 0 | 2 | 3 | 1 | — | 1 | 3 | 3 | 3 | 0 | 3 | 3 | 3 | 3 | 3 | 1 | 1 | 3 | — |
| | 0.0701 | 0 | — | — | 0 | 2 | 0 | 0 | — | 0 | 2 | 2 | 3 | 0 | 3 | 3 | 3 | 3 | 3 | 0 | 0 | 2 | — |
| | 0.0350 | 0 | — | — | 0 | 1 | 0 | 0 | — | 0 | 0 | 1 | 1 | 0 | 2 | 1 | 1 | 2 | 2 | 0 | 0 | 1 | — |
| | 0.0175 | 0 | — | — | 0 | 0 | 0 | 0 | — | 0 | 0 | 0 | 0 | 0 | 1 | 1 | 1 | 0 | 0 | 0 | 0 | 1 | — |
| | 0.0087 | 0 | — | — | 0 | 0 | 0 | 0 | — | 0 | 0 | 0 | 0 | 0 | 1 | 1 | 0 | 0 | 0 | 0 | 0 | 0 | — |
| 28 | 5.6050 | 0 | — | — | 1 | 3 | 2 | 2 | — | 2 | 3 | 3 | 3 | 3 | 3 | 3 | 3 | 3 | 3 | 3 | 3 | 3 | — |
| | 1.1210 | 0 | — | — | 0 | 0 | 1 | 0 | — | 0 | 0 | 2 | 1 | 0 | 3 | 1 | 1 | 3 | 2 | 0 | 2 | 1 | — |
| | 0.5605 | 0 | — | — | 0 | 0 | 0 | 0 | — | 0 | 1 | 1 | 1 | 0 | 0 | 0 | 2 | 1 | 2 | 0 | 0 | 0 | — |
| | 0.2803 | 0 | — | — | 0 | 0 | 0 | 0 | — | 0 | 0 | 0 | 0 | 0 | 0 | 0 | 0 | 0 | 0 | 0 | 0 | 0 | — |
| | 0.1401 | 0 | — | — | 0 | N | 0 | 0 | — | 0 | 0 | 0 | 0 | 0 | 0 | 0 | 0 | 0 | 1 | N | N | N | — |
| | 0.0701 | 0 | — | — | 0 | 0 | 0 | 0 | — | 0 | 0 | 0 | 0 | 0 | 0 | 0 | 0 | 0 | 0 | 0 | 0 | 0 | — |
| 29 | 11.2100 | 0 | — | — | 0 | 0 | 1 | 1 | — | 1 | 1 | 0 | 3 | 3 | 2 | 2 | 3 | 3 | 3 | 1 | 2 | 1 | — |
| | 5.6050 | 0 | — | — | 0 | 0 | 0 | 1 | — | 1 | 0 | 0 | 1 | 0 | 2 | 2 | 2 | 3 | 3 | 0 | 2 | 1 | — |
| | 2.8025 | 0 | — | — | 1 | 0 | 1 | 0 | — | 0 | 0 | 0 | 0 | 0 | 2 | 1 | 3 | 3 | 3 | 1 | 1 | 0 | — |
| | 1.1210 | 0 | — | — | 0 | 0 | 0 | 0 | — | 0 | 0 | 0 | 0 | 0 | 2 | 0 | 0 | 2 | 2 | 0 | 0 | 0 | — |
| 30 | 5.6050 | 3 | — | — | 1 | 3 | 2 | 3 | — | 3 | 3 | 3 | 3 | 3 | 3 | 3 | 3 | 3 | 3 | 3 | 3 | 3 | — |
| | 1.1210 | 0 | — | — | 1 | 1 | 1 | 1 | — | 2 | 3 | 1 | 3 | 0 | 3 | 3 | 3 | 3 | 3 | 2 | 2 | 3 | — |
| | 0.5605 | 0 | — | — | 0 | 0 | 1 | 1 | — | 1 | 2 | 0 | 3 | 0 | 3 | 3 | 3 | 3 | 3 | 1 | 1 | 1 | — |
| | 0.2803 | 0 | — | — | 0 | 0 | 0 | 0 | — | 0 | 0 | 0 | 1 | 0 | 2 | 3 | 3 | 3 | 3 | 0 | 0 | 0 | — |
| | 0.1401 | 0 | — | — | 0 | 0 | 0 | 0 | — | 0 | 0 | 0 | 0 | 0 | 2 | 1 | 2 | 0 | 2 | 1 | 0 | 0 | — |
| | 0.0701 | 0 | — | — | 0 | 0 | 0 | 0 | — | 0 | 0 | 0 | 0 | 0 | 1 | 0 | 1 | 0 | 0 | 0 | 0 | 0 | — |
| | 0.0350 | 0 | — | — | 0 | 0 | 0 | 0 | — | 0 | 0 | 0 | 0 | 0 | 1 | 1 | 0 | 0 | 0 | 0 | 0 | 0 | — |
| | 0.0175 | 0 | — | — | 0 | 0 | 0 | 0 | — | 0 | 0 | 0 | 0 | 0 | 1 | 0 | 0 | 0 | 0 | 0 | 0 | 0 | — |
| 31 | 5.6050 | 3 | — | — | 1 | 3 | 3 | 3 | — | 3 | 3 | 3 | 3 | 3 | 3 | 3 | 3 | 3 | 3 | 3 | 3 | 3 | — |
| | 1.1210 | 1 | — | — | 0 | 3 | 2 | 3 | — | 2 | 3 | 3 | 3 | 3 | 3 | 3 | 3 | 3 | 3 | 3 | 3 | 3 | — |
| | 0.5605 | 0 | — | — | 0 | 3 | 3 | 1 | — | 1 | 3 | 3 | 3 | 3 | 3 | 3 | 3 | 3 | 3 | 1 | 3 | 3 | — |
| | 0.2803 | 0 | — | — | 0 | 3 | 0 | 0 | — | 0 | 1 | 3 | 2 | 0 | 3 | 3 | 3 | 3 | 0 | N | 3 | 3 | — |

TABLE B-continued

| | | | | | | | | | | | | | | | | | | | | | | | |
|---|---|---|---|---|---|---|---|---|---|---|---|---|---|---|---|---|---|---|---|---|---|---|---|
| | 0.1401 | 0 | — | — | 0 | 3 | 0 | 0 | — | 0 | 0 | 2 | 2 | 0 | 3 | 2 | 1 | 2 | 0 | 0 | 3 | 1 | — |
| | 0.0701 | 0 | — | — | 0 | 0 | 0 | 0 | — | 0 | 0 | 1 | 1 | 0 | 0 | 0 | 0 | 0 | 0 | 0 | 1 | 0 | — |
| | 0.0350 | 0 | — | — | 0 | N | 0 | 0 | — | 0 | 0 | 0 | 0 | 0 | 1 | 0 | 0 | 2 | 0 | 0 | 0 | 1 | — |
| | 0.0175 | 0 | — | — | 0 | N | 0 | 0 | — | 0 | 0 | 0 | 0 | 0 | 0 | 0 | 0 | 1 | 0 | N | N | N | — |
| | 0.0087 | 0 | — | — | 0 | N | 0 | 0 | — | 0 | 0 | 0 | 0 | 0 | 0 | 0 | 0 | 0 | 0 | 0 | N | 0 | — |
| 32 | 11.2100 | 0 | — | — | 0 | 3 | 1 | 2 | — | 3 | 1 | 3 | 2 | 0 | 3 | 3 | 2 | 3 | 3 | 2 | 3 | 1 | — |
| | 5.6050 | 0 | — | — | 0 | 3 | 0 | 0 | — | 1 | 0 | 0 | 0 | 0 | 3 | 2 | 0 | 3 | 3 | 1 | 3 | 0 | — |
| | 2.8025 | 0 | — | — | 0 | 3 | 0 | 0 | — | 1 | N | 0 | 0 | 0 | 2 | 0 | 0 | 2 | 0 | N | 3 | 0 | — |
| | 1.1210 | 0 | — | — | 0 | 3 | 0 | 0 | — | 0 | 0 | 0 | 1 | 1 | 2 | 0 | 0 | 2 | 0 | 0 | 3 | 0 | — |
| 33 | 5.6050 | 3 | — | — | 0 | 3 | 3 | 3 | — | 3 | 3 | 3 | 3 | 3 | 3 | 3 | 3 | 3 | 3 | 3 | 3 | 3 | — |
| | 1.1210 | 1 | — | — | 0 | 3 | 1 | 0 | — | 2 | 2 | 3 | 2 | 0 | 3 | 3 | 3 | 3 | 3 | 2 | 3 | 1 | — |
| | 0.5605 | 0 | — | — | 0 | 3 | 0 | 0 | — | 1 | 0 | 2 | 2 | 0 | 3 | 3 | 3 | 2 | 3 | N | 3 | 0 | — |
| | 0.2803 | 0 | — | — | 0 | 1 | 0 | 0 | — | 0 | 0 | 0 | 1 | 0 | 2 | 0 | 0 | 1 | 0 | 0 | 2 | 1 | — |
| | 0.1401 | 0 | — | — | 0 | N | 0 | 0 | — | 0 | 0 | 0 | 0 | 0 | 0 | 0 | 0 | 0 | 0 | 0 | N | 0 | — |
| | 0.0701 | 0 | — | — | 0 | N | 0 | N | — | N | 0 | N | 0 | 0 | 0 | 0 | 0 | 0 | 0 | N | N | 0 | — |
| | 0.0350 | 1 | — | — | 0 | N | 0 | 0 | — | 0 | 0 | 0 | 0 | 0 | 0 | 0 | 0 | 1 | 0 | 0 | N | N | — |
| | 0.0175 | 0 | — | — | 0 | N | 0 | 0 | — | 0 | N | 0 | 0 | 0 | 0 | 0 | 0 | 0 | 0 | N | N | N | — |
| | 0.0087 | 0 | — | — | 0 | 0 | 0 | 0 | — | 0 | 0 | 0 | 0 | 0 | N | 0 | 0 | N | 0 | N | N | 0 | — |
| 34 | 5.6050 | 1 | — | — | 1 | 3 | 2 | 2 | — | 3 | 3 | 3 | 3 | 3 | 3 | 3 | 3 | 3 | 3 | 3 | 3 | 3 | — |
| | 1.1210 | 0 | — | — | 0 | 0 | 0 | 1 | — | 2 | 3 | 3 | 2 | 0 | 3 | 3 | 3 | 3 | 3 | 3 | 3 | 2 | — |
| | 0.5605 | 0 | — | — | 0 | N | 0 | 0 | — | 0 | 3 | 0 | 2 | 0 | 3 | 3 | 3 | 3 | 2 | 1 | 0 | 0 | — |
| | 0.2803 | 0 | — | — | 0 | 0 | 0 | 0 | — | 0 | 2 | 0 | 0 | 0 | 2 | 2 | 1 | 3 | 0 | 0 | 0 | 0 | — |
| | 0.1401 | 0 | — | — | 0 | 0 | 0 | 0 | — | 0 | 0 | 0 | 0 | 0 | 0 | 0 | 0 | 0 | 0 | 0 | 0 | 0 | — |
| | 0.0701 | 0 | — | — | 0 | 0 | 0 | 0 | — | 0 | 0 | 0 | 0 | 0 | 0 | 0 | 0 | 0 | 0 | 0 | N | 0 | — |
| 35 | 5.6050 | 3 | — | — | 1 | 3 | 3 | 3 | — | 3 | 3 | 3 | 3 | 3 | 3 | 3 | 3 | 3 | 3 | 3 | 3 | 3 | — |
| | 1.1210 | 3 | — | — | 0 | 1 | 3 | 3 | — | 3 | 3 | 3 | 3 | 3 | 3 | 3 | 3 | 3 | 3 | 3 | 3 | 3 | — |
| | 0.5605 | 3 | — | — | 0 | 2 | 3 | 2 | — | 3 | 3 | 3 | 3 | 3 | 3 | 3 | 3 | 3 | 3 | 3 | 3 | 3 | — |
| | 0.2803 | 2 | — | — | 1 | 1 | 1 | 2 | — | 2 | 3 | 3 | 3 | 3 | 3 | 3 | 3 | 3 | 3 | 1 | 2 | 3 | — |
| | 0.1401 | 0 | — | — | 0 | N | 2 | 1 | — | 2 | 2 | 2 | 3 | 1 | 3 | 3 | 3 | 2 | 3 | N | N | N | — |
| | 0.0701 | 0 | — | — | 0 | 1 | 0 | 0 | — | 0 | 1 | 2 | 2 | 0 | 3 | 3 | 3 | 3 | 3 | 0 | 1 | 1 | — |
| | 0.0350 | 0 | — | — | 0 | 0 | 0 | 0 | — | 0 | 0 | 0 | 2 | 0 | 2 | 2 | 1 | 0 | 0 | 0 | 0 | 0 | — |
| | 0.0175 | 0 | — | — | 0 | 0 | 0 | 0 | — | 0 | 0 | 1 | 0 | 0 | 2 | 2 | 0 | 0 | 0 | 0 | 0 | 0 | — |
| | 0.0087 | 0 | — | — | 0 | 0 | 1 | 0 | — | 0 | 0 | 0 | 0 | 0 | 0 | 0 | 0 | 0 | 0 | 0 | 0 | 0 | — |
| 36 | 5.6050 | 3 | — | — | 0 | 3 | 3 | 3 | — | 3 | 3 | N | 3 | 3 | 3 | 3 | 3 | 3 | 3 | 3 | 3 | 3 | — |
| | 1.1210 | 1 | — | — | 0 | 2 | 2 | 2 | — | 3 | 3 | 3 | 3 | 3 | 3 | 3 | 3 | 3 | 3 | 1 | 3 | 3 | — |
| | 0.5605 | 1 | — | — | 0 | 2 | 0 | 2 | — | 3 | 2 | N | 3 | 1 | 3 | 3 | 3 | 3 | 3 | 1 | 3 | 3 | — |
| | 0.2803 | 0 | — | — | 0 | 2 | 0 | 0 | — | 0 | 1 | 3 | 2 | 1 | 2 | 3 | 3 | 3 | 3 | 0 | 2 | 2 | — |
| | 0.1401 | 0 | — | — | 0 | 0 | 0 | 0 | — | 0 | 0 | 0 | 1 | 0 | 1 | 2 | 3 | 3 | 3 | 0 | 1 | 2 | — |
| | 0.0701 | 0 | — | — | 0 | 0 | 0 | 0 | — | 0 | 0 | 0 | 2 | 0 | 0 | 2 | 2 | 3 | 3 | 0 | N | 2 | — |
| | 0.0350 | 0 | — | — | 0 | 0 | 0 | 0 | — | 0 | 0 | 0 | 0 | 0 | 0 | 0 | 1 | 1 | 2 | 0 | 1 | 1 | — |
| | 0.0175 | 0 | — | — | 0 | 1 | 0 | 0 | — | 0 | 0 | 0 | 0 | 0 | 0 | 0 | 0 | 0 | 0 | 0 | 0 | 0 | — |
| 37 | 5.6050 | 3 | — | — | 2 | 3 | 3 | 3 | — | 3 | 3 | 3 | 3 | 3 | 3 | 3 | 3 | 3 | 3 | 3 | 3 | 3 | — |
| | 1.1210 | 2 | — | — | 0 | 3 | 2 | 3 | — | 3 | 3 | 3 | 3 | 3 | 3 | 3 | 3 | 3 | 3 | 3 | 3 | 3 | — |
| | 0.5605 | 0 | — | — | 0 | 1 | 2 | 2 | — | 2 | 3 | 2 | 3 | 3 | 3 | 3 | 3 | 3 | 3 | 3 | 3 | 3 | — |
| | 0.2803 | 0 | — | — | 0 | N | 2 | 2 | — | 2 | 2 | 1 | 3 | 1 | 1 | 3 | 3 | 3 | 3 | N | 3 | 3 | — |
| | 0.1401 | 0 | — | — | 0 | 0 | 1 | 1 | — | 1 | 1 | 0 | 1 | 0 | 1 | 3 | 3 | 3 | 3 | 1 | 3 | 3 | — |
| | 0.0701 | 0 | — | — | 0 | 0 | 0 | 0 | — | 0 | 0 | 0 | 0 | 0 | 1 | 2 | 2 | 3 | 3 | 0 | 3 | 1 | — |
| | 0.0350 | 0 | — | — | 0 | 0 | 0 | 0 | — | 1 | 0 | 0 | 0 | 0 | 1 | 0 | 1 | 3 | 3 | 0 | 1 | 1 | — |
| | 0.0175 | 0 | — | — | 0 | 1 | 0 | 0 | — | 0 | 0 | 0 | 0 | 0 | 0 | 0 | 0 | 0 | 2 | 0 | 0 | 0 | — |
| | 0.0087 | 0 | — | — | 0 | 0 | 0 | 0 | — | 0 | 0 | 0 | 0 | 0 | 0 | 0 | 0 | 0 | 1 | N | N | 0 | — |
| | 0.0044 | 0 | — | — | 0 | 0 | 0 | 0 | — | 0 | 0 | 0 | 0 | 0 | 0 | 0 | 0 | 0 | 0 | 0 | 0 | 0 | — |
| 38 | 5.6050 | 0 | — | — | 0 | 2 | 2 | 2 | — | 3 | 3 | 3 | 3 | 3 | 3 | 3 | 3 | 3 | 3 | 3 | 3 | 3 | — |
| | 1.1210 | 0 | — | — | 0 | 1 | 1 | 0 | — | 2 | 1 | 2 | 1 | 1 | 2 | 3 | 3 | 3 | 3 | 1 | 3 | 3 | — |

TABLE B-continued

| | | | | | | | | | | | | | | | | | | | | | | | | |
|---|---|---|---|---|---|---|---|---|---|---|---|---|---|---|---|---|---|---|---|---|---|---|---|---|
| | | 0.5605 | 0 | — | — | 0 | 0 | 0 | 0 | — | 1 | 0 | 2 | 0 | 0 | 1 | 0 | 3 | 3 | 3 | 1 | 3 | 3 | — |
| | | 0.2803 | 0 | — | — | 0 | 0 | 0 | 0 | — | 1 | 0 | 0 | 0 | 0 | 1 | 0 | 0 | 3 | 3 | 0 | 2 | 3 | — |
| | | 0.1401 | 0 | — | — | 0 | 0 | 0 | 0 | — | 1 | 0 | 0 | 0 | 0 | 1 | 0 | 2 | 2 | 3 | 0 | 1 | 1 | — |
| | | 0.0701 | 0 | — | — | 0 | 0 | 0 | 0 | — | 0 | 0 | 0 | 0 | 0 | 0 | 1 | 1 | 0 | 0 | 0 | 0 | 1 | — |
| | | 0.0350 | 0 | — | — | 0 | 0 | 0 | 0 | — | 0 | 0 | 0 | 0 | 0 | 0 | 0 | 1 | 0 | 0 | 0 | 0 | 0 | — |
| | | 0.0175 | 0 | — | — | 0 | 0 | 0 | 0 | — | 0 | 0 | 0 | 0 | 0 | 0 | 0 | 1 | 0 | 0 | 0 | N | 0 | — |
| 39 | | 5.6050 | 0 | — | — | 1 | 3 | 2 | 1 | — | 3 | 3 | 3 | 2 | 3 | 3 | 3 | 3 | 3 | 3 | 1 | 3 | 3 | — |
| | | 1.1210 | 0 | — | — | 0 | 1 | 1 | 1 | — | 1 | 0 | 0 | 0 | 1 | 0 | 3 | 3 | 3 | 3 | 1 | 3 | 3 | — |
| | | 0.5605 | 0 | — | — | 1 | 1 | 1 | 0 | — | 1 | 0 | 0 | 1 | 1 | N | 3 | 3 | 3 | 3 | N | 3 | 3 | — |
| | | 0.2803 | 0 | — | — | 0 | 0 | 0 | 0 | — | 0 | 0 | 0 | 0 | 0 | 0 | 0 | 2 | 2 | 2 | 0 | 0 | 3 | — |
| | | 0.1401 | 0 | — | — | 0 | 0 | 0 | 0 | — | 0 | 0 | 0 | 0 | 0 | 0 | 0 | 2 | 3 | 1 | 0 | 1 | 3 | — |
| | | 0.0701 | 0 | — | — | 0 | 0 | 0 | 0 | — | 0 | 0 | 0 | 0 | 0 | 0 | 0 | 2 | 2 | 1 | 0 | 0 | 1 | — |
| | | 0.0350 | 0 | — | — | 0 | 0 | 0 | 0 | — | 0 | 0 | 0 | 0 | 0 | 0 | 0 | 1 | 0 | 0 | 0 | 0 | 1 | — |
| | | 0.0175 | 0 | — | — | 0 | 0 | 0 | 0 | — | 0 | 0 | 0 | 0 | 0 | 0 | 0 | 2 | 1 | 0 | N | N | 0 | — |
| 40 | | 5.6050 | 2 | — | — | 1 | 3 | 3 | 2 | — | 3 | 3 | 2 | 3 | 3 | 3 | 3 | 3 | 3 | 3 | 3 | 3 | 3 | — |
| | | 1.1210 | 1 | — | — | 0 | 3 | 0 | 0 | — | 0 | 1 | 1 | 0 | 0 | 2 | 2 | 0 | 3 | 3 | 1 | 3 | 1 | — |
| | | 0.5605 | 0 | — | — | 0 | 3 | 0 | 1 | — | 2 | 0 | 1 | 0 | 0 | 3 | 2 | 0 | 3 | 0 | 3 | 3 | 1 | — |
| | | 0.2803 | 0 | — | — | 0 | 0 | 0 | 0 | — | 0 | 0 | 0 | 0 | 0 | 0 | 0 | 0 | 3 | 3 | 0 | 2 | 0 | — |
| | | 0.1401 | 0 | — | — | 0 | N | 0 | 0 | — | 0 | 0 | 0 | 0 | 0 | 0 | 0 | 0 | 2 | 0 | N | N | N | — |
| | | 0.0701 | 0 | — | — | 0 | N | N | 0 | — | 0 | 0 | 0 | 0 | 0 | 0 | 0 | 0 | 1 | 2 | 0 | N | N | — |
| | | 0.0350 | 0 | — | — | 0 | 0 | 0 | 0 | — | 0 | N | 0 | N | 0 | N | 0 | 0 | 2 | 1 | N | 0 | 0 | — |
| 41 | | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | | 1.1210 | 2 | — | — | 0 | 0 | 2 | 3 | — | 3 | 3 | 3 | 3 | 3 | 3 | 3 | 3 | 3 | 3 | 3 | 3 | 2 | — |
| | L | 0.5605 | 0 | — | — | 1 | 0 | 3 | 2 | — | 2 | 3 | 3 | 3 | 1 | 3 | 3 | 3 | 3 | 3 | 1 | 3 | 0 | — |
| | L | 0.2803 | 0 | — | — | 0 | N | 0 | 2 | — | 1 | 1 | 3 | 3 | 0 | 3 | 3 | 3 | 3 | 3 | N | 3 | N | — |
| | | 0.1401 | 0 | — | — | 1 | 1 | 1 | 2 | — | 1 | 1 | 3 | 3 | 0 | 3 | 3 | 3 | 3 | 3 | 1 | 3 | N | — |
| | | 0.0701 | 0 | — | — | 0 | 1 | 0 | 1 | — | 0 | 1 | 1 | 2 | 0 | 3 | 3 | 3 | 3 | 3 | 1 | 0 | N | — |
| | | 0.0350 | 0 | — | — | 0 | 2 | 0 | 0 | — | 0 | 0 | N | 0 | 0 | 0 | 0 | 0 | 0 | 3 | 0 | N | N | — |
| | | 0.0175 | 0 | — | — | 0 | 1 | 0 | 0 | — | 0 | 0 | 0 | 0 | 0 | 0 | 0 | 0 | 0 | 2 | 0 | N | N | — |
| | | 0.0087 | 0 | — | — | N | 0 | 0 | 1 | — | 0 | 0 | 1 | 0 | 0 | N | 1 | 0 | N | 0 | 0 | 0 | 0 | — |
| 42 | | 11.2100 | 2 | — | — | 1 | 1 | 2 | 0 | — | 0 | 2 | 3 | 3 | 1 | 2 | 0 | 3 | 3 | 3 | 0 | 0 | 0 | — |
| | | 5.6050 | 0 | — | — | 0 | 0 | 0 | 0 | — | 0 | 0 | 1 | 0 | 0 | 1 | 0 | 1 | 1 | 1 | 0 | 0 | 0 | — |
| | | 2.8025 | 0 | — | — | 0 | 1 | 0 | 0 | — | 0 | 0 | 0 | 0 | N | 0 | 0 | 0 | 2 | 2 | 0 | 0 | 0 | — |
| | | 1.1210 | 0 | — | — | 0 | 1 | 0 | 0 | — | 0 | 0 | 1 | 0 | 0 | 0 | 0 | 0 | 0 | 0 | 0 | 0 | 0 | — |
| 43 | | 5.6050 | 0 | — | — | 0 | 3 | 3 | 1 | — | 2 | 1 | 3 | 2 | 1 | 3 | 3 | 3 | 3 | 3 | 3 | 3 | 1 | — |
| | | 1.1210 | 0 | — | — | 0 | 0 | 0 | 0 | — | 1 | 0 | 0 | 1 | 0 | 0 | 0 | 0 | 1 | 0 | 2 | 3 | 3 | — |
| | | 0.5605 | 0 | — | — | 0 | 0 | N | 0 | — | 0 | 0 | 0 | 0 | 0 | 0 | 0 | 0 | 1 | 0 | 0 | 2 | 2 | — |
| | | 0.2803 | 0 | — | — | 0 | 0 | 0 | 0 | — | 0 | 0 | 0 | 0 | 0 | 0 | 0 | 0 | 0 | 0 | 0 | 3 | 0 | — |
| | | 0.1401 | 0 | — | — | 0 | 0 | 0 | 0 | — | 0 | 0 | 0 | 0 | 0 | 0 | 0 | 0 | 1 | 0 | 0 | 0 | 1 | — |
| | | 0.0701 | N | — | — | 0 | 0 | 0 | 0 | — | 0 | 0 | 0 | 0 | 0 | 0 | 0 | 0 | 0 | 0 | 0 | 0 | 0 | — |
| | | 0.0350 | N | — | — | 0 | 0 | 0 | 0 | — | 0 | 0 | 0 | 0 | 0 | 0 | 0 | 0 | 1 | 0 | 0 | 0 | N | — |
| | | 0.0175 | 0 | — | — | 0 | 0 | 0 | 0 | — | 0 | 0 | 0 | 0 | 0 | 0 | 0 | 0 | N | 0 | 0 | 0 | 0 | — |
| | | 0.0087 | 0 | — | — | 0 | 0 | 0 | 0 | — | 0 | 0 | 0 | 0 | 0 | 0 | 0 | 0 | 0 | 0 | 0 | 0 | 0 | — |
| 44 | | 3.6993 | 0 | — | — | 0 | 0 | 0 | 0 | — | 0 | 1 | 0 | 2 | 2 | 1 | 0 | 0 | 3 | 0 | 0 | 2 | 2 | — |
| | | 1.1210 | 0 | — | — | 0 | 0 | 0 | 0 | — | 1 | 1 | 0 | 0 | 0 | 0 | 0 | 0 | 0 | 0 | 0 | 0 | 0 | — |
| | | 0.5605 | 0 | — | — | 0 | 0 | 0 | 0 | — | 0 | 0 | 0 | 0 | 0 | 0 | 0 | 0 | N | 0 | 0 | 0 | 0 | — |
| | | 0.2803 | 0 | — | — | 0 | 0 | 0 | 0 | — | 0 | 0 | 0 | 0 | 0 | 0 | 0 | 0 | N | 0 | 0 | 0 | 0 | — |
| | | 0.1401 | 0 | — | — | 0 | N | 1 | 0 | — | 0 | 0 | 0 | 0 | 0 | 0 | 0 | 0 | 0 | 0 | N | N | N | — |
| | | 0.0701 | 0 | — | — | 0 | 0 | 0 | 0 | — | 0 | 0 | 0 | 0 | 0 | 0 | 0 | 0 | 1 | 0 | 0 | 0 | 0 | — |
| 45 | M | 5.6050 | 0 | — | — | 0 | 0 | 3 | 0 | — | 1 | 0 | 3 | 3 | 0 | 3 | 3 | 3 | 3 | 3 | 3 | 0 | 0 | — |
| | M | 1.1210 | 0 | — | — | N | 0 | N | 0 | — | 1 | 0 | 0 | 1 | 0 | 2 | 3 | 3 | 1 | 3 | 1 | 0 | 0 | — |
| | M | 0.5605 | 0 | — | — | N | 0 | N | 0 | — | 0 | 0 | 0 | 0 | 0 | 0 | 2 | 0 | 0 | 2 | N | 0 | 0 | — |
| | M | 0.2803 | 0 | — | — | N | 0 | N | 0 | — | 0 | 0 | 0 | 0 | 0 | 0 | 1 | 0 | 0 | 0 | 1 | 0 | 0 | — |

TABLE B-continued

| | | | | | | | | | | | | | | | | | | | | | | | |
|---|---|---|---|---|---|---|---|---|---|---|---|---|---|---|---|---|---|---|---|---|---|---|---|
| M | 0.1401 | N | — | — | N | 0 | N | 0 | — | 0 | 0 | 0 | 0 | 0 | 0 | 0 | 0 | 0 | 0 | 0 | 0 | 0 | — |
| M | 0.0701 | 0 | — | — | 1 | 0 | N | 0 | — | 0 | 0 | 0 | 0 | 0 | 0 | 0 | 1 | 0 | 0 | 0 | 0 | 0 | — |
| M | 0.0350 | 0 | — | — | N | 0 | N | 0 | — | 0 | 0 | 0 | 0 | 0 | 0 | 0 | 0 | 1 | 0 | 1 | N | 1 | — |
| M | 0.0175 | 0 | — | — | 0 | 0 | 0 | 1 | — | 1 | 0 | 0 | 0 | 0 | 1 | 0 | 0 | 0 | 1 | 1 | N | N | — |
| 46 | 5.6050 | 0 | — | — | 0 | 3 | 2 | 2 | — | 3 | 3 | 3 | 3 | 3 | 3 | 3 | 3 | 3 | 3 | 3 | 3 | 3 | — |
| | 1.1210 | 0 | — | — | 0 | 3 | 0 | 1 | — | 0 | 0 | 0 | 2 | 1 | 3 | 2 | 3 | 3 | 3 | 0 | 3 | 3 | — |
| | 0.5605 | 0 | — | — | 0 | 1 | 0 | 0 | — | 0 | 0 | 0 | 1 | 0 | 3 | 3 | 3 | 3 | 3 | 1 | 3 | 3 | — |
| | 0.2803 | 0 | — | — | 0 | 0 | 0 | 0 | — | 0 | 0 | 0 | 0 | 0 | 3 | 0 | 0 | 3 | 1 | 0 | 3 | 1 | — |
| | 0.1401 | 0 | — | — | 0 | N | 0 | 1 | — | 0 | 0 | 0 | 0 | 0 | 3 | 0 | 0 | 3 | 0 | 1 | N | 1 | — |
| | 0.0701 | 0 | — | — | 0 | 0 | 0 | 0 | — | 0 | 0 | 0 | 0 | 0 | 3 | 0 | 0 | 3 | 0 | N | 3 | 1 | — |
| 47 | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | 1.1210 | 3 | — | — | 0 | 3 | 3 | 3 | — | 3 | 3 | 3 | 3 | 3 | 3 | 3 | 3 | 3 | 3 | 3 | 3 | 3 | — |
| | 0.5605 | 3 | — | — | 0 | 3 | 2 | 3 | — | 3 | 3 | 3 | 3 | 3 | 3 | 3 | 3 | 3 | 3 | 3 | 3 | 3 | — |
| | 0.2803 | 0 | — | — | 0 | 3 | 3 | 3 | — | 3 | 3 | 3 | 3 | 2 | 3 | 3 | 3 | 3 | 3 | 3 | 3 | 3 | — |
| | 0.1401 | 0 | — | — | 0 | 2 | 2 | 1 | — | 1 | 0 | 0 | 2 | 0 | 3 | 3 | 3 | 3 | 3 | 1 | 3 | 2 | — |
| | 0.0701 | 0 | — | — | 0 | 3 | 0 | 0 | — | 0 | 0 | 1 | 0 | 0 | 3 | 3 | 3 | 3 | 3 | 3 | 3 | 2 | — |
| | 0.0350 | 0 | — | — | 0 | 0 | 0 | 0 | — | 0 | 0 | 1 | 0 | 0 | 2 | 3 | 1 | 3 | 3 | N | 2 | 1 | — |
| | 0.0175 | 0 | — | — | 0 | N | 0 | 0 | — | 0 | 0 | 0 | 0 | 0 | 1 | 0 | 1 | 2 | 0 | 2 | 2 | 1 | — |
| | 0.0087 | 0 | — | — | 0 | N | 0 | 0 | — | 0 | 0 | 0 | 0 | 0 | 1 | 0 | 0 | N | 0 | N | N | N | — |
| | 0.0044 | 0 | — | — | 0 | 1 | 0 | 0 | — | 0 | 0 | 0 | 0 | 0 | 1 | 0 | 0 | 3 | 0 | 1 | 1 | N | — |
| 48 | 5.6050 | 2 | — | — | 2 | 3 | 3 | 2 | — | 3 | 3 | 3 | 3 | 3 | 3 | 3 | 3 | 3 | 3 | 3 | 3 | 3 | — |
| | 1.1210 | 1 | — | — | 0 | 3 | 0 | 2 | — | 2 | 3 | 3 | 2 | 2 | 3 | 3 | 3 | 3 | 3 | 3 | 3 | 3 | — |
| | 0.5605 | 0 | — | — | 0 | 3 | 0 | 0 | — | 1 | 3 | 2 | 2 | 0 | 3 | 3 | 3 | 3 | 3 | 3 | 3 | 1 | — |
| | 0.2803 | 0 | — | — | 0 | 3 | 0 | 0 | — | 0 | 2 | 1 | 0 | 0 | 3 | 3 | 3 | 3 | 3 | 3 | 3 | N | — |
| | 0.1401 | 0 | — | — | 0 | 0 | 0 | 0 | — | 0 | 0 | 0 | 0 | 0 | 3 | 3 | 3 | 1 | 3 | 0 | 1 | 0 | — |
| | 0.0701 | 0 | — | — | 0 | N | 0 | 0 | — | 0 | 0 | 0 | 0 | 0 | 3 | 0 | 3 | 0 | 3 | 0 | N | 0 | — |
| | 0.0350 | 0 | — | — | 0 | 1 | 0 | 0 | — | 0 | 0 | 0 | 0 | 0 | 3 | 0 | 0 | N | 0 | 1 | N | N | — |
| | 0.0175 | 0 | — | — | 1 | 1 | 0 | 0 | — | 0 | 0 | 0 | 0 | 0 | 2 | 0 | 0 | N | 0 | 0 | 1 | 1 | — |
| 49 | 5.6050 | 3 | — | — | 2 | 3 | 3 | 3 | — | 3 | 3 | 3 | 3 | 3 | 3 | 3 | 3 | 3 | 3 | 3 | 3 | 3 | — |
| | 1.1210 | 3 | — | — | 3 | 3 | 3 | 2 | — | 2 | 3 | 3 | 3 | 3 | 3 | 3 | 3 | 3 | 3 | 3 | 3 | 1 | — |
| | 0.5605 | 0 | — | — | 3 | 3 | 0 | 3 | — | 2 | 0 | 3 | 3 | 1 | 3 | 3 | 3 | 3 | 3 | 3 | 3 | 1 | — |
| | 0.2803 | 0 | — | — | 0 | 1 | 0 | 2 | — | 0 | 0 | 3 | 2 | 0 | 3 | 3 | 3 | 3 | 3 | N | 3 | 2 | — |
| | 0.1401 | 0 | — | — | 1 | 0 | 0 | 0 | — | 0 | 0 | 0 | 0 | 0 | 2 | 2 | 3 | 3 | 3 | 1 | 3 | 1 | — |
| | 0.0701 | 0 | — | — | 0 | N | 0 | 0 | — | 0 | 0 | 0 | 0 | 0 | 2 | 2 | 0 | 0 | 0 | 0 | 3 | 1 | — |
| | 0.0350 | 0 | — | — | 0 | 0 | 0 | 0 | — | 0 | 0 | 0 | 0 | 0 | 2 | 2 | 0 | N | 0 | 0 | 3 | 1 | — |
| | 0.0175 | 0 | — | — | 1 | 0 | 0 | 0 | — | 0 | 0 | 0 | 0 | 0 | 2 | 2 | 0 | N | 0 | 0 | 3 | 0 | — |
| | 0.0087 | 0 | — | — | 0 | 1 | 0 | 0 | — | 0 | N | 0 | 0 | 0 | 1 | 0 | N | N | N | N | 3 | N | — |
| 50 | 5.6050 | 3 | — | — | 0 | 0 | 2 | 1 | — | 2 | 3 | 3 | 3 | 3 | 3 | 3 | 3 | 3 | 3 | 3 | 0 | 3 | — |
| | 1.1210 | 1 | — | — | 0 | 0 | 2 | 2 | — | 2 | 3 | 3 | 2 | 3 | 3 | 3 | 3 | 3 | 3 | 2 | 2 | 1 | — |
| | 0.5605 | 0 | — | — | 0 | 0 | 1 | 1 | — | 0 | 3 | 3 | 2 | 1 | 3 | 3 | 3 | 3 | 3 | 3 | 0 | 0 | — |
| | 0.2803 | 0 | — | — | 0 | N | 0 | N | — | 1 | 2 | 3 | 3 | 3 | 3 | 3 | 3 | 3 | 3 | 3 | N | N | — |
| | 0.1401 | N | — | — | N | N | N | N | — | N | N | N | N | N | N | N | N | N | N | N | N | N | — |
| | 0.0701 | 0 | — | — | 0 | 0 | N | 1 | — | 0 | 0 | 0 | 1 | 0 | 0 | 0 | 1 | 2 | 2 | 0 | 0 | 0 | — |
| | 0.0350 | 0 | — | — | N | 0 | 0 | N | — | 0 | 0 | N | 0 | N | 0 | N | 0 | 0 | 0 | 0 | 0 | 0 | — |
| | 0.0175 | 0 | — | — | 0 | 0 | 0 | 0 | — | 0 | 0 | 1 | 1 | 0 | 0 | 0 | 0 | 0 | 0 | 0 | 0 | 0 | — |
| | 0.0087 | 0 | — | — | 0 | 0 | N | 0 | — | 0 | 0 | 1 | 1 | 0 | 0 | N | N | 0 | N | 0 | 0 | N | — |
| 51 | 5.6050 | 3 | — | — | 2 | 3 | 3 | 3 | — | 3 | 3 | 3 | 3 | 3 | 3 | 3 | 3 | 3 | 3 | 3 | 3 | 3 | — |
| | 1.1210 | 0 | — | — | 0 | 1 | 3 | 0 | — | 1 | 3 | 3 | 3 | 1 | 3 | 3 | 3 | 3 | 3 | 2 | 3 | 2 | — |
| | 0.5605 | 0 | — | — | 0 | 0 | 0 | 1 | — | 0 | 2 | 3 | N | 0 | 2 | 3 | 2 | 3 | 3 | 0 | 1 | 1 | — |
| | 0.2803 | 0 | — | — | 0 | 0 | N | 0 | — | 0 | 0 | 0 | 2 | 0 | 1 | 0 | 3 | 3 | 3 | 0 | 0 | 0 | — |
| | 0.1401 | 0 | — | — | 0 | 0 | 0 | 0 | — | 0 | N | 0 | 1 | 0 | 0 | 1 | 3 | 2 | 3 | 0 | 1 | 1 | — |
| | 0.0701 | 1 | — | — | 0 | 0 | N | 0 | — | 0 | 0 | 0 | 1 | 0 | 0 | 0 | 0 | 3 | 2 | 0 | 0 | 0 | — |
| | 0.0350 | 2 | — | — | 0 | 0 | 0 | 0 | — | 0 | N | 0 | 0 | 0 | 1 | 0 | 0 | 0 | 2 | 0 | 0 | 0 | — |

TABLE B-continued

| | | | | | | | | | | | | | | | | | | | | | | | |
|---|---|---|---|---|---|---|---|---|---|---|---|---|---|---|---|---|---|---|---|---|---|---|---|
| | 0.0175 | 0 | — | — | 0 | 0 | 0 | 0 | — | 0 | N | 0 | 0 | 0 | 0 | 0 | 0 | 0 | 0 | 0 | N | 1 | — |
| | 0.0087 | 1 | — | — | 0 | 0 | 0 | 0 | — | 0 | 0 | 0 | 0 | 0 | 0 | 0 | 0 | 1 | 0 | 0 | 1 | 0 | — |
| 52 | 5.6050 | 1 | — | — | 0 | 0 | 3 | 1 | — | 2 | 2 | 3 | 3 | 3 | 3 | 3 | 3 | 3 | 3 | 3 | 3 | 3 | — |
| | 1.1210 | 0 | — | — | 0 | 0 | 1 | 0 | — | 0 | 1 | 0 | 2 | 0 | 0 | 1 | 3 | 3 | 3 | 1 | 2 | 2 | — |
| | 0.5605 | 1 | — | — | 0 | 0 | 0 | 1 | — | 0 | 0 | 0 | 0 | 0 | 1 | 0 | 3 | 3 | 2 | 1 | 1 | 0 | — |
| | 0.2803 | 1 | — | — | 0 | N | 0 | 1 | — | 0 | 0 | 0 | 0 | 0 | 0 | 0 | 1 | 3 | 2 | N | N | N | — |
| | 0.1401 | 0 | — | — | 0 | 0 | 0 | 0 | — | 0 | 0 | 1 | 0 | 0 | N | 0 | 0 | 2 | 0 | 0 | 1 | 0 | — |
| | 0.0701 | N | — | — | 0 | 0 | 3 | 0 | — | 0 | 0 | 0 | 0 | 0 | 0 | 0 | 0 | 3 | 0 | N | 0 | 0 | — |
| 53 | 5.6050 | 3 | 1 | 3 | 0 | 3 | 3 | 3 | 3 | 3 | 3 | 3 | 3 | 3 | 3 | 3 | 3 | 3 | 3 | — | — | — | — |
| | 1.1210 | 2 | 0 | 3 | 0 | 3 | 3 | 3 | 3 | 2 | 3 | 3 | 3 | 3 | 3 | 3 | 3 | 3 | 3 | — | — | — | — |
| | 0.5605 | 0 | 0 | 1 | 0 | 0 | 3 | 1 | 1 | 1 | 3 | 3 | 3 | 3 | 2 | 3 | 3 | 3 | 3 | — | — | — | — |
| | 0.2803 | 0 | 0 | 0 | 0 | 0 | 0 | 0 | 0 | 0 | 1 | 1 | 3 | 2 | 0 | 3 | 3 | 0 | 3 | — | — | — | — |
| | 0.1401 | N | 0 | 0 | 0 | 1 | 0 | 0 | 0 | 0 | 0 | 1 | 2 | 0 | 0 | 1 | 3 | 0 | 3 | — | — | — | — |
| | 0.0701 | 0 | 0 | 0 | 0 | 0 | 0 | 0 | 0 | 0 | 0 | 0 | 1 | 0 | 0 | 0 | 0 | 0 | 1 | — | — | — | — |
| | 0.0351 | 0 | 0 | 0 | N | 0 | 0 | 0 | 0 | 0 | 0 | 0 | 0 | 0 | 0 | 0 | 0 | 0 | 0 | — | — | — | — |
| | 0.0175 | 0 | 0 | 0 | 0 | 0 | 0 | 0 | 0 | 0 | 0 | 0 | 0 | 0 | 0 | 0 | 0 | 0 | 0 | — | — | — | — |
| | 0.0087 | 0 | 0 | 0 | 0 | 0 | 0 | 1 | 0 | 0 | 1 | 0 | 0 | 0 | 0 | 0 | 0 | 0 | 0 | — | — | — | — |
| 54 | 5.6050 | 3 | 2 | 3 | 1 | 3 | 3 | 3 | 3 | 3 | 3 | 3 | 3 | 3 | 3 | 3 | 3 | 3 | 3 | — | — | — | — |
| | 1.1210 | 3 | 0 | 3 | N | 3 | 3 | 3 | 3 | 3 | 3 | 3 | 3 | 3 | 3 | 3 | 3 | 3 | 3 | — | — | — | — |
| | 0.5605 | 2 | 0 | 2 | 0 | 2 | 3 | 3 | 2 | 3 | 3 | 3 | 3 | 3 | 3 | 3 | 3 | 3 | 3 | — | — | — | — |
| | 0.2803 | 2 | 0 | 1 | 0 | 1 | 1 | 1 | 1 | 1 | 3 | 3 | 3 | 3 | 3 | 3 | 3 | 3 | 3 | — | — | — | — |
| | 0.1401 | 0 | 0 | 1 | 0 | 0 | 1 | 0 | 0 | 0 | 3 | 3 | 3 | 1 | 3 | 3 | 3 | 3 | 3 | — | — | — | — |
| | 0.0701 | 0 | 0 | 1 | 0 | 0 | 0 | 0 | 0 | 0 | 1 | 1 | 3 | 0 | 0 | 2 | 3 | 0 | 3 | — | — | — | — |
| | 0.0351 | 0 | 0 | 1 | 0 | N | 0 | 0 | N | 1 | 2 | 2 | 2 | 1 | 1 | 1 | 0 | 0 | 1 | — | — | — | — |
| | 0.0175 | 0 | 0 | 0 | 0 | 1 | 0 | 1 | 0 | 1 | 0 | 1 | 0 | 0 | 0 | 0 | 2 | 0 | 1 | — | — | — | — |
| | 0.0087 | 0 | 0 | 0 | N | 0 | 0 | 1 | 0 | 0 | 0 | 1 | 0 | 0 | 0 | 0 | 0 | 0 | 0 | — | — | — | — |
| | 0.0044 | 0 | N | 0 | 0 | 0 | 0 | 1 | 1 | 0 | 0 | 1 | 0 | 0 | 0 | 0 | 0 | 0 | 0 | — | — | — | — |
| 55 | 5.6050 | 3 | 3 | 3 | 1 | 3 | 3 | 3 | 3 | 3 | 3 | 3 | 3 | 3 | 3 | 3 | 3 | 3 | 3 | — | — | — | — |
| | 1.1210 | 1 | 0 | 3 | 0 | 3 | 0 | 2 | 3 | 3 | 3 | 3 | 3 | 3 | 3 | 3 | 3 | 3 | 3 | — | — | — | — |
| | 0.2803 | N | N | 2 | 0 | 2 | 0 | 0 | 0 | 1 | 2 | 2 | 2 | 1 | 2 | 3 | 3 | 0 | 3 | — | — | — | — |
| | 0.0701 | 1 | 1 | 0 | 0 | 3 | 0 | 0 | 0 | 0 | 0 | 0 | 0 | 1 | 1 | 1 | 2 | N | 3 | — | — | — | — |
| | 0.0175 | 2 | 0 | 0 | 0 | 0 | 0 | 0 | 0 | 0 | 0 | 0 | 0 | 0 | 0 | 0 | 0 | 0 | 2 | — | — | — | — |
| | 0.0087 | 1 | 0 | 0 | 0 | 0 | 0 | 0 | 0 | 0 | 0 | 0 | 0 | 0 | 0 | 0 | 0 | 0 | 0 | — | — | — | — |
| 56 < | 5.6050 | 3 | 0 | 3 | 2 | 3 | 3 | 3 | 3 | 3 | 3 | 3 | 3 | 3 | 3 | 3 | 3 | 3 | 3 | — | — | — | — |
| < | 1.1210 | 2 | 0 | 3 | 0 | 3 | 3 | 2 | 3 | 2 | 3 | 2 | 3 | 3 | 3 | 3 | 3 | 3 | 3 | — | — | — | — |
| < | 0.2803 | 2 | 0 | 0 | 0 | 0 | 0 | 1 | 1 | 0 | 3 | 0 | 3 | 1 | 3 | 3 | 3 | 3 | 3 | — | — | — | — |
| < | 0.0701 | 1 | 0 | 0 | N | 1 | 2 | 0 | 3 | 0 | 0 | N | 0 | 0 | 0 | 0 | 0 | 3 | 1 | — | — | — | — |
| < | 0.0175 | 0 | 0 | 0 | N | 0 | 2 | 0 | 1 | 0 | 0 | 0 | 0 | 1 | 0 | 0 | 0 | 3 | 0 | — | — | — | — |
| < | 0.0087 | 0 | 0 | 0 | 0 | 0 | 0 | 0 | 0 | 0 | 0 | 0 | 0 | 0 | 0 | 0 | 0 | 0 | 0 | — | — | — | — |
| 57 | 5.6050 | 3 | 2 | 3 | 0 | 3 | 3 | 3 | 3 | 3 | 3 | 3 | 3 | 3 | 3 | 3 | 3 | 3 | 3 | — | — | — | — |
| | 1.1210 | 3 | 2 | 3 | N | 3 | 3 | 3 | 3 | 3 | 3 | 3 | 3 | 3 | 3 | 3 | 3 | 3 | 3 | — | — | — | — |
| | 0.2803 | 0 | 2 | 0 | N | 3 | 1 | 1 | 3 | 1 | 1 | 3 | 3 | 1 | 3 | 3 | 3 | 3 | 3 | — | — | — | — |
| | 0.0701 | 0 | 2 | 0 | N | 3 | 1 | 1 | 3 | 1 | 0 | 3 | 3 | 0 | 3 | 3 | 1 | 3 | 2 | — | — | — | — |
| | 0.0175 | 0 | 0 | 0 | N | 2 | 0 | 0 | 1 | 0 | 0 | 0 | 0 | 0 | 2 | 1 | 0 | 1 | 0 | — | — | — | — |
| | 0.0087 | 0 | N | 0 | 0 | N | 0 | 1 | N | 1 | 0 | 1 | 0 | 0 | 3 | 1 | 0 | 0 | 0 | — | — | — | — |
| 58 I | 1.1210 | 1 | 3 | 1 | 1 | 3 | 1 | 1 | — | 1 | 3 | 3 | 3 | 1 | 3 | 3 | 3 | 3 | 3 | — | — | — | 2 |
| I | 0.2803 | 0 | 2 | 0 | 0 | 0 | 0 | 0 | — | 1 | 0 | 3 | 2 | 0 | 0 | 3 | 3 | 3 | 3 | — | — | — | 0 |
| I | 0.0701 | 0 | 1 | 0 | 0 | 0 | 0 | 0 | — | 0 | 0 | 1 | 0 | 0 | 1 | 1 | 0 | 1 | 0 | — | — | — | 0 |
| I | 0.0175 | 0 | N | 0 | 0 | 0 | 0 | 0 | — | 0 | 0 | 1 | 0 | 0 | 1 | 1 | 0 | 0 | 0 | — | — | — | 0 |
| 59 | 5.6050 | 3 | — | — | 2 | 3 | 3 | 3 | — | 3 | 3 | 3 | 3 | 3 | 3 | 3 | 3 | 3 | 3 | 3 | 3 | 3 | — |
| | 1.1210 | 3 | — | — | 1 | 3 | 3 | 3 | — | 3 | 3 | 3 | 3 | 3 | 3 | 3 | 3 | 3 | 3 | 3 | 3 | 3 | — |
| | 0.5605 | 2 | — | — | 0 | 3 | 3 | 3 | — | 3 | 3 | 3 | 3 | 3 | 3 | 3 | 3 | 3 | 3 | 3 | 3 | 3 | — |
| | 0.2803 | 0 | — | — | 0 | 1 | 3 | 3 | — | 3 | 3 | 3 | 3 | 3 | 3 | 3 | 3 | 3 | 3 | 3 | 1 | 3 | — |

TABLE B-continued

| | | | | | | | | | | | | | | | | | | | | | | | |
|---|---|---|---|---|---|---|---|---|---|---|---|---|---|---|---|---|---|---|---|---|---|---|---|
| | 0.1401 | 0 | — | — | 2 | 0 | 1 | 2 | — | 1 | 3 | 3 | 3 | 0 | 3 | 3 | 3 | 2 | 3 | 0 | 2 | 3 | — |
| | 0.0701 | 0 | — | — | 1 | 0 | 0 | 0 | — | 1 | 0 | 3 | 0 | 0 | 1 | 3 | 3 | 3 | 3 | 0 | N | 3 | — |
| | 0.0350 | 1 | — | — | 0 | 0 | 1 | 0 | — | 0 | 0 | 2 | 2 | 0 | 0 | 0 | 3 | 0 | 2 | 1 | 0 | 2 | — |
| | 0.0175 | 0 | — | — | 0 | 0 | 1 | N | — | 0 | 0 | 2 | 0 | 0 | 0 | 0 | 0 | 0 | 0 | 3 | 1 | 3 | — |
| | 0.0087 | 0 | — | — | 1 | 0 | 0 | 0 | — | 0 | 1 | 1 | 1 | 0 | N | 0 | 1 | N | N | 0 | 0 | 1 | — |
| 60 | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | 1.1210 | 0 | — | — | 0 | 3 | 3 | 3 | — | 3 | 3 | 3 | 3 | 3 | 3 | 3 | 3 | 3 | 3 | 3 | 3 | 3 | — |
| | 0.5605 | 0 | — | — | 0 | 3 | 2 | 3 | — | 2 | 1 | 3 | 2 | 2 | 3 | 3 | 3 | 3 | 3 | N | 3 | 2 | — |
| | 0.2803 | 0 | — | — | 1 | 3 | 0 | 1 | — | 0 | 1 | 3 | 3 | 1 | 2 | 3 | 3 | 3 | 3 | 3 | 3 | 3 | — |
| | 0.1401 | 0 | — | — | 0 | 1 | 0 | 1 | — | 0 | 1 | 2 | 2 | 0 | 1 | 1 | 3 | 0 | 3 | 3 | N | 3 | — |
| | 0.0701 | 0 | — | — | N | 0 | 0 | 1 | — | 0 | 0 | 3 | 0 | 0 | 1 | 1 | 0 | 0 | 0 | 3 | 3 | 3 | — |
| | 0.0350 | 0 | — | — | 1 | N | 0 | 3 | — | 0 | 0 | 0 | 0 | 0 | 0 | 0 | 0 | 0 | 0 | 3 | 3 | N | — |
| | 0.0175 | 0 | — | — | 1 | N | 0 | 1 | — | 0 | 0 | 0 | 0 | 0 | 0 | 0 | N | 0 | N | 0 | 3 | 1 | — |
| | 0.0087 | 0 | — | — | N | 0 | 0 | 0 | — | 0 | 0 | 0 | 0 | 0 | 0 | 0 | 0 | 0 | 0 | 0 | 2 | 1 | — |
| 61 | 5.6050 | 3 | 1 | 3 | 2 | 3 | 3 | 3 | 3 | 3 | 3 | 3 | 3 | 3 | 3 | 3 | 3 | 3 | 3 | — | — | — | — |
| | 1.1210 | 2 | 1 | 3 | 0 | 3 | 3 | 1 | 2 | 1 | 3 | 3 | 3 | 3 | 3 | 3 | 3 | 3 | 3 | — | — | — | — |
| | 0.5605 | 2 | 0 | 3 | 0 | 3 | 3 | 1 | 1 | 2 | 3 | 3 | 3 | 3 | 3 | 3 | 3 | 3 | 3 | — | — | — | — |
| | 0.2803 | 1 | 1 | 1 | 0 | 1 | 3 | 1 | 1 | 1 | 3 | 3 | 3 | 2 | 3 | 3 | 3 | 3 | 3 | — | — | — | — |
| | 0.1401 | 0 | 0 | 0 | 0 | 1 | 2 | 0 | 1 | 0 | 1 | 3 | 3 | 1 | 2 | 2 | 3 | 3 | 3 | — | — | — | — |
| | 0.0701 | 0 | 0 | 0 | 0 | 0 | 1 | 0 | 0 | 0 | 0 | 3 | 3 | 1 | 3 | 3 | 3 | 3 | 3 | — | — | — | — |
| | 0.0351 | 0 | 0 | 0 | 1 | 1 | 0 | 1 | 0 | 0 | 0 | 1 | 1 | 0 | 0 | 1 | 3 | 0 | 2 | — | — | — | — |
| | 0.0175 | 0 | 0 | 0 | 0 | 0 | 0 | 1 | 0 | 0 | 0 | 0 | 0 | 0 | 0 | 0 | 0 | 0 | 1 | — | — | — | — |
| | 0.0087 | 1 | 1 | N | 1 | 0 | 0 | 1 | 0 | 1 | 1 | 1 | 1 | 0 | 1 | 1 | 0 | 0 | 0 | — | — | — | — |
| 62 | 5.6050 | 3 | 3 | 3 | 0 | 3 | 3 | 3 | 3 | 3 | 3 | 3 | 3 | 3 | 3 | 3 | 3 | 3 | 3 | — | — | — | — |
| | 1.1210 | 3 | 2 | 3 | 0 | 3 | 3 | 3 | 3 | 3 | 3 | 3 | 3 | 3 | 3 | 3 | 3 | 3 | 3 | — | — | — | — |
| | 0.5605 | 3 | 2 | 3 | N | 3 | 3 | 3 | 3 | 3 | 3 | 3 | 3 | 3 | 3 | 3 | 3 | 3 | 3 | — | — | — | — |
| | 0.2803 | 3 | 2 | 3 | 0 | 3 | 3 | 2 | 1 | 2 | 3 | 3 | 3 | 3 | 3 | 3 | 3 | 3 | 3 | — | — | — | — |
| | 0.1401 | 1 | 1 | 1 | N | 2 | 2 | 1 | 2 | 1 | 3 | 3 | 3 | 3 | 3 | 3 | 3 | 3 | 3 | — | — | — | — |
| | 0.0701 | N | 2 | N | N | 3 | 3 | 2 | 2 | 2 | 3 | 3 | 3 | 2 | 3 | 3 | 3 | 3 | 3 | — | — | — | — |
| | 0.0351 | 1 | 2 | 0 | N | 3 | 0 | 0 | 0 | 0 | 0 | 3 | 2 | 2 | 2 | 2 | 3 | 3 | 3 | — | — | — | — |
| | 0.0175 | 1 | 0 | 1 | 0 | 1 | 0 | 0 | 0 | 0 | 0 | 0 | 1 | 1 | 0 | 0 | 0 | 0 | 0 | — | — | — | — |
| | 0.0087 | 1 | 0 | 0 | N | 1 | 0 | 0 | 0 | 0 | 0 | 0 | 0 | 0 | 0 | 0 | 0 | 0 | 0 | — | — | — | — |
| | 0.0044 | N | 0 | 1 | 1 | 1 | 0 | 1 | 0 | N | N | 0 | N | 0 | 1 | 1 | 0 | 0 | 0 | — | — | — | — |
| 63 F | 5.6050 | 3 | 0 | 3 | 0 | 3 | 3 | 3 | 2 | 3 | 3 | 3 | 3 | 3 | 3 | 3 | 3 | 3 | 3 | — | — | — | — |
| F | 1.1210 | 2 | 0 | 3 | 0 | 1 | 2 | 2 | 1 | 2 | 3 | 3 | 3 | 3 | 3 | 3 | 3 | 3 | 3 | — | — | — | — |
| F | 0.2803 | 0 | 0 | 1 | 0 | 0 | 0 | 0 | 0 | 0 | 3 | 0 | 3 | 1 | 3 | 3 | 3 | 2 | 3 | — | — | — | — |
| F | 0.0701 | 1 | 0 | 0 | 0 | 0 | 0 | 0 | 0 | 0 | 0 | 0 | 0 | 0 | 0 | 0 | 0 | 2 | 0 | — | — | — | — |
| F | 0.0175 | N | N | 0 | 0 | 0 | 0 | 0 | 0 | 0 | 0 | 1 | 1 | N | 0 | 1 | 1 | 1 | 0 | — | — | — | — |
| F | 0.0087 | 0 | 0 | 0 | 0 | 0 | 0 | 0 | 0 | 0 | 0 | N | 0 | 0 | 0 | 0 | 0 | 1 | 0 | — | — | — | — |
| 64 | 5.6050 | 3 | 2 | 3 | 3 | 3 | 3 | 3 | 3 | 3 | 3 | 3 | 3 | 3 | 3 | 3 | 3 | 3 | 3 | — | — | — | — |
| . | 1.1210 | 3 | 1 | 3 | 3 | 3 | 3 | 3 | 3 | 3 | 3 | 3 | 3 | 3 | 3 | 3 | 3 | 3 | 3 | — | — | — | — |
| . | 0.2803 | 0 | 0 | 1 | 2 | 2 | 3 | 1 | 2 | 1 | 3 | 3 | 3 | 3 | 3 | 3 | 3 | 3 | 3 | — | — | — | — |
| . | 0.0701 | 0 | 1 | 0 | 0 | 0 | 0 | 0 | 0 | 0 | 0 | 3 | 2 | 2 | 3 | 3 | 3 | 3 | 3 | — | — | — | — |
| . | 0.0175 | 0 | 0 | 0 | N | 0 | 0 | 0 | 0 | 0 | 0 | 2 | 1 | 0 | 0 | 0 | 3 | 3 | 1 | — | — | — | — |
| . | 0.0087 | 0 | 0 | 0 | 0 | 0 | 0 | 0 | 0 | 0 | 0 | 0 | 0 | 1 | 0 | 0 | 0 | 1 | 0 | — | — | — | — |
| 65 | 5.6050 | 3 | 0 | 3 | 0 | 3 | 3 | 3 | 3 | 3 | 3 | 3 | 3 | 3 | 3 | 3 | 3 | 3 | 3 | — | — | — | — |
| | 1.1210 | 0 | 0 | 1 | N | 3 | 1 | 1 | 2 | 1 | 3 | 3 | 3 | 2 | 3 | 3 | 3 | 3 | 3 | — | — | — | — |
| | 0.2803 | 0 | 0 | 0 | 0 | N | 0 | 0 | 2 | 0 | 0 | 0 | 1 | 0 | 3 | 3 | 3 | 3 | 3 | — | — | — | — |
| | 0.0701 | 0 | 0 | 0 | 0 | 0 | 0 | 0 | 0 | 0 | 0 | 1 | 0 | 0 | 0 | 0 | 0 | 2 | 2 | — | — | — | — |
| | 0.0175 | 0 | 0 | 0 | 0 | 0 | 0 | 0 | 0 | N | 0 | 0 | 0 | 0 | 0 | 0 | 0 | 0 | 0 | — | — | — | — |
| | 0.0087 | 0 | 0 | 0 | N | 0 | 0 | 0 | 0 | 0 | 0 | 0 | 0 | 0 | 0 | 0 | 0 | 0 | 0 | — | — | — | — |

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| 66 | | 5.6050 | 3 | 3 | 3 | 0 | 3 | 3 | 3 | 3 | 3 | 3 | 3 | 3 | 3 | 3 | 3 | 3 | 3 | 3 | — | — | — | — |
| | . | 1.1210 | 3 | 0 | 3 | 1 | 3 | 3 | 2 | 3 | 2 | 3 | 3 | 3 | 3 | 3 | 3 | 3 | 3 | 3 | — | — | — | — |
| | . | 0.2803 | 1 | 0 | 1 | 0 | 2 | 1 | 1 | 2 | 1 | 2 | 3 | 3 | 3 | 3 | 3 | 3 | 3 | 3 | — | — | — | — |
| | . | 0.0701 | 1 | 0 | 0 | 0 | 1 | 1 | 1 | 1 | 0 | 0 | 2 | 3 | 0 | 2 | 3 | 3 | 3 | 3 | — | — | — | — |
| | . | 0.0175 | 0 | N | 0 | 0 | 0 | 0 | N | 0 | 0 | 0 | 0 | 1 | 0 | 0 | 0 | 0 | 1 | 1 | — | — | — | — |
| | . | 0.0087 | 0 | 0 | 0 | 0 | 0 | 0 | 0 | 0 | 0 | 0 | 0 | 0 | 0 | 0 | 0 | 1 | 3 | 1 | — | — | — | — |
| 67 | B | 5.6050 | 3 | 0 | 3 | 3 | 3 | 3 | 3 | 3 | 3 | 3 | 3 | 3 | 3 | 3 | 3 | 3 | 3 | 3 | — | — | — | — |
| | B | 1.1210 | 3 | N | 2 | 1 | 3 | 0 | 1 | 2 | 1 | 3 | 3 | 3 | 3 | 3 | 3 | 3 | 3 | 3 | — | — | — | — |
| | B | 0.2803 | 2 | 0 | 1 | 1 | 0 | 1 | 0 | 0 | 0 | 1 | 1 | 3 | 1 | 3 | 2 | 3 | 3 | 3 | — | — | — | — |
| | B | 0.0701 | 0 | 0 | 0 | 0 | 0 | 0 | 0 | 0 | 0 | 0 | 0 | 1 | 0 | 0 | 0 | 0 | 1 | 0 | — | — | — | — |
| | B | 0.0175 | 0 | 0 | N | 0 | 0 | 0 | 0 | 0 | 0 | 0 | 0 | 1 | 0 | 0 | 0 | 0 | 0 | 0 | — | — | — | — |
| | B | 0.0087 | N | 0 | 0 | 0 | N | 0 | N | 0 | N | 0 | 0 | 0 | 1 | 0 | 0 | 0 | 0 | 0 | — | — | — | — |
| 68 | B | 5.6050 | 3 | 1 | 3 | 0 | 3 | 3 | 3 | 2 | 3 | 3 | 3 | 3 | 3 | 3 | 3 | 3 | 3 | 3 | — | — | — | — |
| | B | 1.1210 | 0 | 0 | 0 | 0 | 1 | 0 | 0 | 1 | 0 | 3 | 3 | 3 | 3 | 3 | 3 | 3 | 3 | 3 | — | — | — | — |
| | B | 0.2803 | 2 | 0 | 0 | N | 1 | 1 | 0 | 0 | 0 | 1 | 0 | 2 | 1 | 1 | 0 | 2 | 3 | 2 | — | — | — | — |
| | B | 0.0701 | 0 | 0 | 0 | 0 | 0 | 0 | 0 | 0 | 0 | 0 | 0 | 1 | 1 | 0 | 0 | 0 | 0 | 0 | — | — | — | — |
| | B | 0.0175 | 0 | 0 | 0 | 0 | 0 | 0 | 0 | 0 | 0 | 0 | 0 | 0 | 0 | 0 | 0 | 0 | 0 | 0 | — | — | — | — |
| | B | 0.0087 | 0 | 0 | 0 | 0 | 0 | 0 | 0 | 0 | 0 | 0 | 0 | 0 | 0 | 0 | 0 | 0 | 0 | 0 | — | — | — | — |
| 69 | B | 5.6050 | 3 | 2 | 3 | 0 | 3 | 3 | 2 | 2 | 3 | 3 | 3 | 3 | 3 | 3 | 3 | 3 | 3 | 3 | — | — | — | — |
| | B | 1.1210 | 1 | 2 | 2 | 1 | 3 | 0 | 3 | 3 | 3 | 3 | 3 | 3 | 3 | 3 | 3 | 3 | 3 | 3 | — | — | — | — |
| | B | 0.2803 | 2 | 0 | 0 | 0 | 3 | 0 | 1 | 2 | 1 | 1 | 3 | 1 | 1 | 3 | 1 | 0 | 3 | 0 | — | — | — | — |
| | B | 0.0701 | 0 | 1 | 0 | 0 | 2 | 0 | 1 | 1 | 0 | 0 | 0 | 0 | 0 | 3 | 0 | 0 | 3 | 0 | — | — | — | — |
| | B | 0.0175 | 0 | 0 | 0 | 0 | N | 0 | 0 | 1 | 0 | 0 | 0 | 0 | 1 | 2 | 0 | 0 | 2 | 0 | — | — | — | — |
| | B | 0.0087 | 0 | N | 0 | 0 | N | 0 | N | N | N | 0 | N | 0 | 0 | N | N | 0 | N | 0 | — | — | — | — |
| 70 | B | 5.6050 | 3 | 0 | 3 | 0 | 3 | 3 | 3 | 3 | 3 | 3 | 3 | 3 | 3 | 3 | 3 | 3 | 3 | 3 | — | — | — | — |
| | B | 1.1210 | 3 | 0 | 1 | 0 | 0 | 0 | 2 | 1 | 1 | 3 | 3 | 3 | 3 | 3 | 3 | 3 | 3 | 3 | — | — | — | — |
| | B | 0.2803 | 2 | 0 | 0 | 0 | 0 | 1 | 0 | 0 | 0 | 0 | 3 | 1 | 0 | 0 | 1 | 2 | 2 | 1 | — | — | — | — |
| | B | 0.0701 | N | 0 | N | 0 | 0 | N | 0 | 0 | 0 | N | 0 | N | N | 0 | 0 | N | 1 | N | — | — | — | — |
| | B | 0.0175 | 2 | 0 | 0 | 0 | 1 | 0 | 0 | 1 | 1 | 0 | 1 | 0 | 0 | 0 | 1 | 1 | N | 1 | — | — | — | — |
| | B | 0.0087 | N | 0 | 0 | 0 | 0 | 0 | 0 | 0 | 0 | 0 | 1 | 1 | 1 | 0 | 0 | 0 | 0 | 0 | — | — | — | — |
| 71 | B | 5.6050 | 3 | 1 | 3 | 1 | 3 | 3 | 3 | 3 | 3 | 3 | 3 | 3 | 3 | 3 | 3 | 3 | 3 | 3 | — | — | — | — |
| | B | 1.1210 | 0 | 2 | 0 | 0 | 2 | 0 | 1 | 1 | 1 | 3 | 3 | 3 | 1 | 3 | 3 | 3 | 3 | 3 | — | — | — | — |
| | B | 0.2803 | 0 | 1 | 0 | 0 | 1 | 0 | 1 | 0 | 1 | 0 | 1 | 1 | 0 | 1 | 0 | 0 | 3 | 1 | — | — | — | — |
| | B | 0.0701 | 0 | N | 0 | 0 | 0 | 0 | 0 | 0 | 0 | 0 | 0 | 0 | 0 | 0 | 0 | 0 | 0 | 0 | — | — | — | — |
| | B | 0.0175 | 0 | N | 0 | 0 | 0 | 0 | 0 | 0 | 0 | 0 | 0 | 0 | 0 | 0 | 0 | 0 | 0 | 0 | — | — | — | — |
| 72 | | 5.6050 | 2 | 1 | 2 | 0 | 3 | 3 | 0 | 1 | 0 | 3 | 3 | 3 | 3 | 3 | 3 | 3 | 3 | 3 | — | — | — | — |
| | | 1.1210 | 2 | 0 | 1 | N | 0 | 1 | 0 | 0 | 1 | 1 | 1 | 1 | 1 | 0 | 0 | 2 | 3 | 1 | — | — | — | — |
| | | 0.2803 | 0 | 0 | 0 | 0 | 0 | N | 0 | 0 | 0 | 0 | 0 | 0 | 1 | 0 | 0 | 0 | 0 | 0 | — | — | — | — |
| | | 0.0701 | 1 | 0 | 0 | 0 | 0 | 0 | 0 | 0 | N | 0 | 0 | 0 | 0 | 0 | 0 | 0 | 0 | 0 | — | — | — | — |
| 73 | | 5.6050 | 1 | 2 | 0 | 0 | 3 | 1 | 1 | — | 2 | 3 | 3 | 3 | 3 | 3 | 3 | 3 | 3 | 3 | — | — | — | 3 |
| | | 1.1210 | 0 | 0 | 0 | 0 | 1 | 0 | 0 | — | 0 | 3 | 0 | 3 | 2 | 3 | 3 | 3 | 3 | 3 | — | — | — | 3 |
| | | 0.2803 | 1 | 0 | 0 | 0 | 0 | 0 | 0 | — | 0 | 0 | 0 | 2 | 0 | 0 | 2 | 1 | 3 | 0 | — | — | — | 0 |
| | | 0.0701 | 0 | 0 | 0 | 0 | 0 | 0 | 0 | — | 0 | 0 | 0 | 0 | 0 | 0 | 0 | 0 | 1 | 0 | — | — | — | 0 |
| | | 0.0175 | 0 | 0 | 0 | 0 | 0 | 0 | 0 | — | 0 | 0 | 0 | 0 | 0 | 0 | 0 | 0 | 0 | 0 | — | — | — | 0 |
| 74 | | 5.6050 | 3 | 3 | 3 | 3 | 3 | 3 | 3 | — | 3 | 3 | 3 | 3 | 3 | 3 | 3 | 3 | 3 | 3 | — | — | — | 3 |
| | | 1.1210 | 3 | 3 | 3 | 1 | 3 | 3 | 3 | — | 3 | 3 | 3 | 3 | 3 | 3 | 3 | 3 | 3 | 3 | — | — | — | 3 |
| | | 0.2803 | 3 | 2 | 2 | 2 | 3 | 2 | 2 | — | 2 | 3 | 3 | 3 | 3 | 3 | 3 | 3 | 3 | 3 | — | — | — | 3 |
| | | 0.0701 | 0 | 1 | 0 | 0 | 3 | 0 | 1 | — | 1 | 3 | 3 | 3 | 1 | 3 | 3 | 3 | 3 | 3 | — | — | — | 0 |
| | | 0.0175 | 0 | 0 | 0 | 0 | 0 | 0 | 0 | — | 1 | 0 | 1 | 1 | 0 | 2 | 1 | 0 | 3 | 1 | — | — | — | 0 |
| | | 0.0044 | 0 | 0 | 0 | 0 | 1 | 0 | 0 | — | 0 | 1 | 0 | 1 | 0 | 0 | 0 | 0 | 0 | 0 | — | — | — | 0 |
| 75 | | 5.6050 | 3 | 2 | 3 | 2 | 3 | 3 | 3 | — | 3 | 3 | 3 | 3 | 3 | 3 | 3 | 3 | 3 | 3 | — | — | — | 3 |
| | | 1.1210 | 2 | 0 | 3 | 0 | 3 | 1 | 2 | — | 3 | 3 | 3 | 3 | 3 | 3 | 3 | 3 | 3 | 3 | — | — | — | 3 |

-continued

TABLE 3-continued

| | | | | | | | | | | | | | | | | | | | | | | | |
|---|---|---|---|---|---|---|---|---|---|---|---|---|---|---|---|---|---|---|---|---|---|---|---|
| | 0.2803 | 0 | 0 | 3 | 0 | 2 | 0 | 1 | — | 0 | 3 | 3 | 3 | 1 | 3 | 3 | 3 | 3 | 3 | — | — | — | 3 |
| | 0.0701 | 0 | 0 | 0 | 0 | 0 | 0 | 0 | — | 0 | 2 | 2 | 2 | 0 | 3 | 3 | 3 | 3 | 2 | — | — | — | 0 |
| | 0.0175 | 0 | 0 | 0 | 0 | 0 | 0 | 0 | — | 0 | 1 | 0 | 2 | 0 | 0 | 0 | 0 | 1 | 0 | — | — | — | 0 |
| | 0.0044 | 0 | 0 | 0 | 1 | 0 | 0 | 0 | — | 0 | 0 | 0 | 1 | 0 | 0 | 0 | N | 1 | N | — | — | — | 0 |
| 76 | 5.6050 | 3 | 1 | 3 | N | 3 | 3 | 3 | 3 | 3 | 3 | 3 | 3 | 3 | 3 | 3 | 3 | 3 | 3 | — | — | — | — |
| | 1.1210 | 2 | 1 | 3 | N | 3 | 1 | 3 | 3 | 3 | 3 | 3 | 3 | 3 | 3 | 3 | 3 | 3 | 3 | — | — | — | — |
| | 0.2803 | 0 | 1 | 1 | N | 1 | 2 | 1 | 2 | 1 | 3 | 3 | 3 | 0 | 3 | 3 | 3 | 3 | 3 | — | — | — | — |
| | 0.0701 | 1 | 2 | 0 | N | 0 | 0 | 0 | 1 | 0 | 0 | 1 | 1 | 0 | 3 | 3 | 1 | 1 | 1 | — | — | — | — |
| | 0.0175 | 0 | 0 | 0 | N | 0 | 0 | 0 | 0 | 0 | 0 | 0 | 0 | 0 | 0 | 1 | 0 | 0 | 0 | — | — | — | — |
| | 0.0087 | 0 | N | 0 | N | 0 | 0 | 0 | 0 | 0 | 0 | 0 | 0 | 0 | 0 | 0 | 0 | 0 | 0 | — | — | — | — |
| 77 | 5.6050 | 3 | 2 | 3 | N | 3 | 3 | 3 | 3 | 3 | 3 | 3 | 3 | 3 | 3 | 3 | 3 | N | 3 | — | — | — | — |
| | 1.1210 | 3 | 1 | 2 | N | 3 | 2 | 2 | 2 | 3 | 3 | 3 | 3 | 3 | 3 | 3 | 3 | N | 3 | — | — | — | — |
| | 0.2803 | 1 | 0 | 1 | N | 3 | 0 | 2 | 0 | 1 | 0 | 3 | 3 | 1 | 3 | 3 | 3 | N | 3 | — | — | — | — |
| | 0.0701 | 0 | 0 | 0 | N | 2 | 0 | 1 | 0 | 0 | 0 | 3 | 2 | 0 | 3 | 3 | 2 | N | 3 | — | — | — | — |
| | 0.0175 | 0 | 0 | 0 | N | 0 | 0 | 0 | 0 | 0 | 0 | 2 | 0 | 0 | 0 | 0 | 0 | N | 0 | — | — | — | — |
| 78 | 5.6050 | 3 | 0 | 3 | N | 3 | 3 | 3 | 3 | 3 | 3 | 3 | 3 | 3 | 3 | 3 | 3 | N | 3 | — | — | — | — |
| | 1.1210 | 3 | N | 3 | N | 3 | 3 | 3 | 3 | 3 | 3 | 3 | 3 | 3 | 3 | 3 | 3 | N | 3 | — | — | — | — |
| | 0.2803 | 1 | N | 3 | N | 3 | 2 | 2 | 3 | 2 | 2 | 3 | 3 | 1 | 3 | 3 | 3 | N | 3 | — | — | — | — |
| | 0.0701 | 0 | 0 | 0 | N | 3 | 0 | 0 | 2 | 0 | 1 | 3 | 3 | 0 | 3 | 3 | 3 | N | 3 | — | — | — | — |
| | 0.0175 | 0 | 0 | 0 | N | 3 | 0 | 0 | 0 | 0 | 0 | 2 | 2 | 0 | 2 | 0 | 3 | N | 2 | — | — | — | — |
| | 0.0087 | 0 | 0 | 0 | N | 3 | 0 | 0 | 0 | 0 | 0 | 0 | 0 | 0 | 0 | 0 | 0 | N | 0 | — | — | — | — |
| 79 | 5.6050 | 1 | — | — | 1 | 3 | 2 | 3 | — | 3 | 1 | 3 | 3 | 2 | 3 | 3 | 3 | 3 | 3 | 3 | 3 | 3 | — |
| | 1.1210 | 1 | — | — | N | 2 | 0 | 1 | — | 0 | 0 | 3 | 3 | 0 | 2 | 3 | 3 | 3 | 3 | 1 | 3 | 3 | — |
| | 0.5605 | 0 | — | — | 0 | 0 | 0 | 1 | — | 0 | 0 | 0 | 3 | 1 | 3 | 3 | 3 | 3 | 3 | 1 | 3 | 3 | — |
| | 0.2803 | 0 | — | — | 1 | N | 0 | 0 | — | 0 | 0 | 0 | 1 | 0 | 0 | 1 | 0 | 3 | 0 | 0 | 3 | 1 | — |
| | 0.1401 | 0 | — | — | 0 | 1 | 0 | 0 | — | 0 | 0 | 0 | 0 | 0 | 0 | 0 | 0 | 3 | 0 | N | 3 | N | — |
| | 0.0701 | 0 | — | — | 0 | 0 | 1 | 0 | — | 0 | 0 | 0 | 0 | 0 | 0 | 0 | 0 | 3 | 0 | 0 | 3 | 3 | — |
| 80 | 5.6050 | 3 | 0 | 3 | 0 | 3 | 3 | 3 | — | 3 | 3 | 3 | 3 | 3 | 3 | 3 | 3 | 3 | 3 | — | — | — | 3 |
| | 1.1210 | 1 | 0 | 2 | 0 | 3 | 2 | 1 | — | 2 | 2 | 3 | 3 | 3 | 2 | 3 | 3 | 3 | 3 | — | — | — | 3 |
| | 0.2803 | 1 | 0 | 2 | 1 | 2 | 3 | N | — | N | 0 | 3 | 3 | 0 | 1 | 3 | 3 | 3 | 3 | — | — | — | 3 |
| | 0.0701 | 0 | 0 | 0 | 0 | 0 | 0 | 0 | — | 0 | 0 | 0 | 0 | 0 | 0 | 0 | 0 | 2 | 0 | — | — | — | 1 |
| 81 | 5.6050 | 3 | 0 | 3 | 0 | 3 | 3 | 3 | — | 3 | 3 | 3 | 3 | 3 | 3 | 3 | 3 | 3 | 3 | — | — | — | 3 |
| | 1.1210 | 3 | 0 | 3 | 0 | 3 | 3 | 2 | — | 3 | 3 | 3 | 3 | 3 | 3 | 3 | 3 | 3 | 3 | — | — | — | 3 |
| | 0.2803 | 0 | 0 | 0 | 0 | 3 | 0 | 0 | — | 1 | 3 | 3 | 3 | 0 | 3 | 3 | 3 | 3 | 3 | — | — | — | 3 |
| | 0.0701 | 0 | 0 | 0 | 0 | 2 | 0 | 0 | — | 0 | 1 | 0 | 3 | 0 | 0 | 0 | 1 | 3 | 3 | — | — | — | 3 |
| | 0.0175 | 0 | 0 | 0 | 0 | 0 | 0 | 0 | — | 0 | 1 | 0 | 3 | 0 | 0 | 0 | 0 | 0 | 0 | — | — | — | 2 |
| | 0.0087 | N | 0 | 0 | 0 | 0 | 0 | 0 | — | 0 | 1 | 0 | 3 | 0 | 0 | 0 | 0 | 0 | 0 | — | — | — | 1 |
| 82 | 5.6050 | 3 | 0 | 3 | 0 | 3 | 3 | 3 | — | 3 | 3 | 3 | 3 | 3 | 3 | 3 | 3 | 3 | 3 | — | — | — | 3 |
| | 1.1210 | 0 | 0 | 3 | 0 | 2 | 1 | 1 | — | 2 | 3 | 3 | 3 | 3 | 3 | 3 | 3 | 3 | 3 | — | — | — | 3 |
| | 0.2803 | 0 | 0 | 0 | 0 | 3 | 0 | 0 | — | 0 | 1 | 2 | 3 | 0 | 3 | 3 | 3 | 3 | 3 | — | — | — | 3 |
| | 0.0701 | 1 | 0 | 0 | 0 | 0 | 0 | 0 | — | 0 | 1 | 0 | 2 | 0 | 0 | 1 | 2 | 3 | 3 | — | — | — | 0 |
| | 0.0175 | 0 | 0 | 1 | 0 | N | 0 | 0 | — | 0 | 1 | 0 | N | 1 | 0 | 0 | 0 | 3 | 1 | — | — | — | 0 |
| | 0.0087 | 0 | 0 | 0 | 0 | 0 | 0 | 0 | — | 0 | 0 | 0 | N | 0 | 0 | 0 | 0 | 1 | 0 | — | — | — | 0 |
| 83 | 5.6050 | 2 | — | — | 1 | 1 | 2 | 3 | — | 2 | 3 | 3 | 3 | 3 | 3 | 3 | 3 | 3 | 3 | 3 | 3 | 3 | — |
| | 1.1210 | 1 | — | — | 0 | 0 | 3 | 0 | — | 0 | 1 | 3 | 1 | 1 | 3 | 3 | 3 | 3 | 3 | 1 | 0 | 3 | — |
| | 0.5605 | 0 | — | — | 0 | 0 | 0 | 0 | — | 0 | 0 | 1 | 0 | 0 | 3 | 3 | 3 | 2 | 0 | 1 | 0 | 2 | — |
| | 0.2803 | 0 | — | — | 0 | 0 | 0 | 0 | — | 0 | 0 | 0 | 0 | 0 | 1 | 1 | 1 | 0 | 0 | 1 | 0 | 2 | — |
| | 0.1401 | 0 | — | — | 0 | 0 | 0 | 0 | — | 0 | 0 | 0 | 0 | 0 | N | 0 | 1 | 0 | 0 | 0 | 0 | 0 | — |
| | 0.0701 | 0 | — | — | 0 | 0 | 0 | 0 | — | 0 | 0 | 0 | 0 | 0 | 2 | 0 | 0 | 0 | 0 | 0 | 0 | 0 | — |
| | 0.0350 | 0 | — | — | 0 | 0 | 0 | 0 | — | 0 | 0 | 0 | 0 | 0 | 2 | N | 0 | 0 | 0 | 1 | 0 | N | — |
| | 0.0175 | 0 | — | — | 0 | 0 | 0 | 0 | — | 0 | 0 | 0 | 0 | 0 | 1 | 1 | 0 | 0 | 0 | 0 | 0 | 0 | — |
| 84 | 5.6050 | 3 | — | — | 0 | 1 | 3 | 3 | — | 1 | 1 | 3 | 3 | 3 | 3 | 3 | 3 | 3 | 3 | 3 | 3 | 3 | — |

-continued

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| | | 1.1210 | 1 | — | — | 0 | 0 | 2 | 3 | — | 1 | 0 | 2 | 3 | 0 | 2 | 3 | 3 | 3 | 3 | 3 | 2 | 3 | — |
| | | 0.5605 | 0 | — | — | 0 | 0 | 1 | 0 | — | 0 | 0 | 0 | 0 | 0 | 0 | 3 | 3 | 3 | 3 | 0 | 0 | 3 | — |
| | | 0.2803 | 0 | — | — | 0 | 0 | 0 | 0 | — | 0 | 0 | 0 | 0 | 0 | 0 | 3 | 3 | 1 | 2 | 0 | 0 | 2 | — |
| | | 0.1401 | 0 | — | — | 0 | 0 | N | 0 | — | 0 | 0 | 0 | 0 | 0 | 0 | 0 | 0 | 0 | 0 | 1 | 1 | 3 | — |
| | | 0.0701 | 0 | — | — | N | 0 | 1 | 0 | — | 0 | 0 | 0 | 0 | 0 | 1 | 0 | 0 | 0 | 0 | 1 | 0 | 1 | — |
| | | 0.0350 | 0 | — | — | 0 | 1 | 0 | 0 | — | 0 | 0 | 0 | 0 | 0 | 0 | 0 | 0 | 0 | 0 | 0 | 1 | 0 | — |
| | | 0.0175 | 0 | — | — | 0 | 0 | 0 | 0 | — | 0 | 0 | 0 | 0 | 0 | 0 | 0 | 0 | 0 | 0 | 0 | 0 | 1 | — |
| | | 0.0087 | 0 | — | — | 0 | 0 | 0 | 0 | — | 0 | 0 | 0 | 0 | 0 | 0 | 0 | 0 | 0 | 0 | 0 | 0 | 0 | — |
| 85 | | 5.6050 | 3 | — | — | 1 | 2 | 3 | 3 | — | 3 | 3 | 3 | 3 | 3 | 3 | 3 | 3 | 3 | 3 | 3 | 2 | 2 | — |
| | | 1.1210 | 1 | — | — | 0 | 1 | 3 | 1 | — | 0 | 3 | 2 | 0 | 0 | 3 | 3 | 3 | 3 | 3 | 1 | 2 | 3 | — |
| | | 0.5605 | 0 | — | — | 0 | 0 | 0 | 2 | — | 0 | 1 | 3 | 1 | 0 | 3 | 3 | 3 | 3 | 3 | 3 | 3 | 3 | — |
| | | 0.2803 | 0 | — | — | 1 | 1 | N | 0 | — | 0 | 0 | 3 | 0 | N | 3 | 0 | 3 | 3 | 3 | 3 | 3 | 3 | — |
| | | 0.1401 | 0 | — | — | 0 | 1 | 0 | 0 | — | 0 | 0 | 1 | 0 | 0 | 1 | 0 | 2 | 3 | 3 | 2 | 2 | 3 | — |
| | | 0.0701 | 0 | — | — | 1 | 2 | N | 1 | — | 0 | 0 | 0 | 0 | 0 | 1 | 1 | 0 | 1 | 0 | 1 | 2 | 1 | — |
| | | 0.0350 | 1 | — | — | 0 | 0 | 1 | 0 | — | 0 | 0 | 0 | 1 | 1 | 0 | 0 | 0 | 0 | 1 | 0 | 1 | 1 | — |
| | | 0.0175 | 0 | — | — | 0 | 0 | 0 | 0 | — | 0 | 0 | 0 | 0 | 0 | 0 | 0 | 0 | 1 | 0 | 0 | 0 | 0 | — |
| | | 0.0087 | 0 | — | — | 0 | 0 | 1 | 0 | — | 0 | 0 | 0 | 0 | 0 | 0 | 0 | 0 | 0 | 0 | 0 | 0 | 0 | — |
| 86 | | 5.6050 | 3 | 3 | 3 | 3 | 3 | 3 | 3 | — | 3 | 3 | 3 | 3 | 3 | 3 | 3 | 3 | 3 | 3 | — | — | — | 3 |
| | | 1.1210 | 3 | 0 | 3 | 1 | 3 | 3 | 3 | — | 3 | 3 | 3 | 3 | 3 | 3 | 3 | 3 | 3 | 3 | — | — | — | 3 |
| | | 0.2803 | 2 | N | 3 | 0 | 3 | 0 | 3 | — | 3 | 3 | 2 | 3 | 2 | 3 | 3 | 3 | 3 | 3 | — | — | — | 3 |
| | | 0.0701 | 0 | 1 | 2 | 0 | 3 | 0 | 1 | — | 2 | 1 | 2 | 1 | 0 | 2 | 2 | 3 | 3 | 3 | — | — | — | 3 |
| | | 0.0175 | 1 | 0 | 2 | 1 | 0 | 0 | 0 | — | 1 | 1 | 0 | 0 | 1 | 1 | 0 | 0 | 3 | 2 | — | — | — | 3 |
| | | 0.0087 | N | 0 | 2 | 0 | 0 | 0 | 0 | — | 0 | 0 | 0 | 0 | 0 | 1 | 0 | 0 | 2 | 1 | — | — | — | 3 |
| 87 | | 5.6050 | 3 | 3 | 3 | 3 | 3 | 3 | 3 | — | 3 | 3 | 3 | 3 | 3 | 3 | 3 | 3 | 3 | 3 | — | — | — | 3 |
| | | 1.1210 | 3 | 1 | 3 | 1 | 3 | 3 | 3 | — | 3 | 3 | 3 | 3 | 2 | 3 | 3 | 3 | 3 | 3 | — | — | — | 3 |
| | | 0.2803 | 1 | 1 | 3 | 1 | 3 | 0 | 3 | — | 3 | 2 | 3 | 3 | 1 | 3 | 3 | 3 | 3 | 3 | — | — | — | 3 |
| | | 0.0701 | 1 | 0 | 3 | 0 | 2 | 0 | 2 | — | 2 | 1 | 1 | 1 | 0 | 1 | 3 | 3 | 3 | 3 | — | — | — | 3 |
| | | 0.0175 | 0 | 0 | 0 | 0 | 2 | 0 | 0 | — | 0 | 1 | 0 | 0 | 0 | 0 | 1 | 3 | 3 | 3 | — | — | — | 3 |
| | | 0.0087 | 1 | 0 | 0 | 0 | 1 | 0 | 0 | — | 0 | 0 | 1 | 0 | 0 | 0 | 0 | 1 | 2 | 0 | — | — | — | 3 |
| 88 | | 5.6050 | 3 | 3 | 3 | 3 | 3 | 3 | 3 | — | 3 | 3 | 3 | 3 | 3 | 3 | 3 | 3 | 3 | 3 | — | — | — | 3 |
| | | 1.1210 | 2 | 1 | 3 | 0 | 3 | 3 | 3 | — | 3 | 3 | 3 | 3 | 3 | 2 | 3 | 3 | 3 | 3 | — | — | — | 3 |
| | | 0.2803 | 0 | 1 | 3 | 0 | 3 | 0 | 3 | — | 3 | 2 | 0 | 1 | 0 | 2 | 3 | 3 | 3 | 3 | — | — | — | 3 |
| | | 0.0701 | 0 | 0 | 0 | 0 | 1 | 0 | 2 | — | 0 | 0 | 0 | 0 | 0 | 0 | 0 | 0 | 3 | 0 | — | — | — | 3 |
| | | 0.0175 | 0 | 0 | 0 | 0 | 0 | 0 | 0 | — | 0 | 0 | 0 | 0 | 0 | 0 | 0 | 0 | 0 | 0 | — | — | — | 3 |
| 89 | | 5.6050 | 3 | — | — | 3 | 3 | 2 | 2 | — | 2 | 3 | 1 | 3 | 3 | 3 | 3 | 3 | 3 | 3 | 3 | 3 | 3 | — |
| | | 1.1210 | 1 | — | — | 0 | 3 | 1 | 2 | — | 2 | 3 | 0 | 2 | 2 | 2 | 3 | 3 | 3 | 3 | 2 | 3 | 3 | — |
| | | 0.5605 | 0 | — | — | 2 | 2 | 1 | 1 | — | 0 | 0 | 0 | 2 | 0 | 0 | 3 | 2 | 3 | 3 | 1 | 3 | 1 | — |
| | | 0.2803 | 0 | — | — | 0 | 0 | 0 | 0 | — | 0 | 0 | 0 | 0 | 0 | 0 | 0 | 1 | 2 | 2 | 0 | 1 | 0 | — |
| | | 0.1401 | 0 | — | — | 0 | 0 | 0 | 0 | — | 0 | 0 | 0 | 0 | 0 | 0 | 0 | 0 | 3 | 0 | 0 | 1 | 0 | — |
| | | 0.0701 | 0 | — | — | 0 | 0 | 0 | 0 | — | 0 | 0 | 0 | 0 | 0 | 0 | 0 | 0 | 2 | 1 | 0 | 0 | 0 | — |
| | | 0.0350 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0175 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0087 | 0 | — | — | 0 | 0 | 0 | 0 | — | 0 | 0 | 0 | 0 | 0 | 0 | 0 | 0 | 0 | 0 | 0 | 0 | 0 | — |
| 90 | ( | 5.6050 | N | — | — | N | N | N | N | — | N | N | N | N | N | N | N | N | N | N | N | N | N | — |
| | | 5.6050 | 3 | — | — | 1 | 3 | 3 | 3 | — | 3 | 3 | 0 | 3 | 3 | 3 | 3 | 3 | 3 | 3 | 3 | 3 | 3 | — |
| | ( | 1.1210 | N | — | — | N | N | N | N | — | N | N | N | N | N | N | N | N | N | N | N | N | N | — |
| | | 1.1210 | 2 | — | — | 0 | 3 | 2 | 2 | — | 2 | 3 | 0 | 1 | 3 | 2 | 3 | 3 | 3 | 3 | 2 | 3 | 3 | — |
| | | 0.5605 | 0 | — | — | 0 | 2 | 1 | 2 | — | 1 | 0 | 0 | 1 | 0 | 1 | 3 | 3 | 3 | 3 | 1 | 3 | 2 | — |
| | ( | 0.5605 | N | — | — | N | N | N | N | — | N | N | N | N | N | N | N | N | N | N | N | N | N | — |
| | | 0.2803 | 0 | — | — | 0 | 1 | 0 | 0 | — | 1 | 0 | 0 | 1 | 0 | 0 | 0 | 1 | 3 | 3 | 0 | 1 | 1 | — |
| | ( | 0.2803 | N | — | — | N | N | N | N | — | N | N | N | N | N | N | N | N | N | N | N | N | N | — |
| | | 0.1401 | 0 | — | — | 0 | 0 | 0 | 1 | — | 0 | 0 | 0 | 0 | 0 | 0 | 1 | 1 | 3 | 2 | 0 | 1 | 1 | — |

-continued

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| | ( | 0.1401 | N | — | — | N | N | N | N | — | N | N | N | N | N | N | N | N | N | N | N | N | N | — |
| | ( | 0.0701 | N | — | — | N | N | N | N | — | N | N | N | N | N | N | N | N | N | N | N | N | N | — |
| | | 0.0701 | 0 | — | — | 0 | 0 | 0 | 0 | — | 0 | 0 | 0 | 0 | 0 | 0 | 0 | 0 | 3 | 2 | 0 | 0 | 0 | — |
| | | 0.0350 | 0 | — | — | 0 | 0 | 0 | 0 | — | 0 | 0 | 0 | 0 | 0 | 0 | 0 | 0 | 2 | 2 | 0 | 0 | 0 | — |
| | ( | 0.0350 | N | — | — | N | N | N | N | — | N | N | N | N | N | N | N | N | N | N | N | N | N | — |
| | | 0.0175 | 0 | — | — | 0 | 0 | 0 | 0 | — | 0 | 0 | 0 | 0 | 0 | 0 | 0 | 0 | 0 | 0 | 0 | 0 | 0 | — |
| | ( | 0.0175 | N | — | — | N | N | N | N | — | N | N | N | N | N | N | N | N | N | N | N | N | N | — |
| | ( | 0.0087 | N | — | — | N | N | N | N | — | N | N | N | N | N | N | N | N | N | N | N | N | N | — |
| | | 0.0087 | 0 | — | — | 0 | 0 | 0 | 0 | — | 0 | 0 | 0 | 0 | 0 | 0 | 0 | 0 | 0 | 0 | 0 | 0 | 0 | — |
| 91 | | 11.2100 | 0 | — | — | 0 | 3 | 0 | 0 | — | 1 | 0 | 1 | 0 | 0 | 1 | 2 | 2 | 3 | 3 | 1 | 3 | 3 | — |
| | | 5.6050 | 0 | — | — | 0 | 0 | 0 | 0 | — | 0 | 0 | 0 | 0 | 0 | 0 | 0 | 0 | 0 | 2 | 0 | 3 | 1 | — |
| | | 2.8025 | 0 | — | — | 1 | N | 0 | 0 | — | 0 | 0 | 0 | 0 | 0 | 0 | 0 | 0 | N | 1 | N | N | N | — |
| | | 1.1210 | 0 | — | — | 0 | 1 | 0 | 0 | — | 0 | 0 | 0 | 0 | 0 | 0 | 0 | 0 | N | 0 | 0 | 1 | 0 | — |
| 92 | | 5.6050 | 3 | 1 | 2 | 1 | 3 | 3 | 3 | 3 | 3 | 2 | 3 | 3 | 3 | 3 | 3 | 3 | 3 | 3 | — | — | — | — |
| | | 1.1210 | 0 | 0 | 0 | 0 | 1 | 1 | 1 | 2 | 1 | 1 | 3 | 3 | 2 | 3 | 3 | 3 | 3 | 3 | — | — | — | — |
| | | 0.2803 | 0 | 0 | 0 | 0 | 0 | 0 | 0 | 0 | 0 | 0 | 1 | 0 | 0 | 0 | 3 | 0 | 3 | 0 | — | — | — | — |
| | | 0.0701 | 0 | 0 | 1 | N | 0 | 0 | 0 | 0 | 0 | 0 | 0 | 0 | 0 | 0 | 0 | 0 | 0 | 0 | — | — | — | — |
| 94 | | 5.6050 | 1 | — | — | 0 | 2 | 0 | 2 | — | 0 | 0 | 0 | 1 | — | 1 | 3 | 3 | 3 | — | 3 | 3 | 3 | — |
| | | 1.1210 | 1 | — | — | 0 | 0 | 0 | 0 | — | 0 | 0 | 0 | 0 | — | 0 | 0 | 0 | 0 | — | 1 | 1 | 0 | — |
| | | 0.2803 | 0 | — | — | 0 | 0 | 0 | 0 | — | 0 | 0 | 0 | 0 | — | 0 | 0 | 0 | 0 | — | 0 | 0 | 0 | — |
| 95 | | 5.6050 | 3 | — | — | 0 | 3 | 3 | 3 | — | 3 | 3 | 3 | 3 | 3 | 3 | 3 | 3 | 3 | 3 | 3 | 3 | 3 | — |
| | | 1.1210 | 0 | — | — | 0 | 2 | 0 | 0 | — | 0 | 1 | 1 | 2 | 0 | 3 | 3 | 3 | 3 | 3 | 0 | 1 | 0 | — |
| | | 0.5605 | 0 | — | — | 0 | N | 0 | 0 | — | 0 | 0 | 1 | 0 | 0 | 0 | 3 | 3 | 0 | 3 | 0 | N | 0 | — |
| | | 0.2803 | 0 | — | — | 0 | N | 0 | 0 | — | 0 | 0 | 1 | 0 | 0 | 2 | 3 | 3 | 0 | 3 | N | N | N | — |
| | | 0.1401 | 0 | — | — | 0 | 0 | 0 | 1 | — | 0 | 0 | 0 | 0 | 0 | 0 | 2 | 2 | 0 | 3 | 0 | N | 0 | — |
| | | 0.0701 | 0 | — | — | 0 | 0 | 1 | N | — | 1 | 0 | 0 | 0 | 0 | 0 | 1 | 0 | 0 | 1 | N | 0 | 0 | — |
| | | 0.0350 | 0 | — | — | 0 | N | 0 | 1 | — | 0 | 0 | 0 | 0 | 0 | 0 | 1 | 0 | 0 | 0 | N | N | N | — |
| | | 0.0175 | 0 | — | — | 0 | 0 | 0 | 0 | — | 0 | 0 | 0 | 0 | 0 | 0 | 0 | 0 | 0 | 0 | 0 | N | 0 | — |
| 96 | — | 5.6050 | 3 | 3 | 3 | 3 | 3 | 3 | 3 | 3 | 3 | 3 | 3 | 3 | 3 | 3 | 3 | 3 | 3 | 3 | — | — | — | — |
| | — | 1.1210 | 1 | 2 | 3 | 0 | 3 | 3 | 3 | 3 | 0 | 3 | 3 | 3 | 3 | 3 | 3 | 3 | 3 | 3 | — | — | — | — |
| | — | 0.5605 | 1 | 0 | 1 | 0 | 3 | 2 | 0 | 3 | 0 | 2 | 3 | 3 | 3 | 3 | 3 | 3 | 3 | 3 | — | — | — | — |
| | — | 0.2803 | 0 | N | 1 | 1 | 1 | 0 | 1 | 1 | 1 | 1 | 1 | 2 | 0 | 3 | 3 | 3 | 3 | 3 | — | — | — | — |
| | — | 0.1401 | 0 | N | 0 | N | 1 | 1 | 2 | 1 | 0 | 1 | 2 | 3 | 0 | 0 | 3 | 3 | 3 | 3 | — | — | — | — |
| | — | 0.0701 | 0 | 0 | 0 | N | 1 | 0 | 0 | 1 | 0 | 1 | 1 | 3 | 1 | 0 | 3 | 2 | 1 | 3 | — | — | — | — |
| 97 | | 5.6050 | 3 | 0 | 3 | 1 | 3 | 3 | 3 | 3 | 3 | 3 | 3 | 3 | 3 | 3 | 3 | 3 | 3 | 3 | — | — | — | — |
| | | 1.1210 | 2 | 0 | 3 | 0 | 3 | 3 | 2 | 2 | 3 | 3 | 3 | 3 | 3 | 3 | 3 | 3 | 3 | 3 | — | — | — | — |
| | | 0.5605 | 2 | 0 | 3 | 0 | 3 | 2 | 2 | 2 | 3 | 3 | 3 | 3 | 3 | 3 | 3 | 3 | 3 | 3 | — | — | — | — |
| | | 0.2803 | 0 | 0 | 1 | 0 | 3 | 0 | 1 | 1 | 1 | 1 | 3 | 3 | 1 | 3 | 3 | 3 | 3 | 3 | — | — | — | — |
| | | 0.1401 | N | 1 | 1 | N | 3 | 0 | 1 | 0 | 3 | 3 | 2 | 3 | N | 3 | 3 | 3 | 3 | 3 | — | — | — | — |
| | | 0.0701 | N | 1 | 0 | N | 3 | 0 | 1 | 0 | 1 | 0 | 3 | 3 | 0 | 3 | 3 | 3 | 3 | 3 | — | — | — | — |
| | | 0.0351 | 1 | 0 | 0 | 0 | 1 | 0 | 0 | 0 | 0 | 0 | 2 | 1 | 0 | 0 | 3 | 3 | 3 | 2 | — | — | — | — |
| | | 0.0175 | 0 | 0 | 0 | 0 | 0 | 0 | 0 | 0 | 0 | 0 | 0 | 0 | 0 | 0 | 0 | 1 | 0 | 1 | — | — | — | — |
| | | 0.0087 | 0 | 0 | 0 | 0 | 1 | 0 | 0 | 0 | 1 | 0 | 0 | 0 | 0 | 0 | 0 | 0 | 0 | 0 | — | — | — | — |
| | | 0.0044 | N | 0 | 0 | 0 | N | 0 | 0 | 0 | 1 | 0 | 1 | 0 | 0 | 1 | 0 | 0 | 0 | 0 | — | — | — | — |
| 98 | | 5.6050 | 3 | 2 | 3 | 0 | 3 | 3 | 3 | 1 | 3 | 3 | 3 | 3 | 3 | 3 | 3 | 3 | 3 | 3 | — | — | — | — |
| | | 1.1210 | 0 | 1 | 1 | 0 | 3 | 2 | 2 | 1 | 2 | 2 | 3 | 3 | 3 | 3 | 3 | 3 | 3 | 3 | — | — | — | — |
| | | 0.5605 | 0 | 0 | 0 | 0 | 3 | 0 | 1 | 0 | 2 | 0 | 3 | 1 | 0 | 3 | 3 | 3 | 3 | 3 | — | — | — | — |
| | | 0.2803 | N | 0 | 0 | 0 | 1 | 0 | 0 | 0 | 0 | 0 | 2 | N | N | 2 | 2 | 3 | 1 | 3 | — | — | — | — |
| | | 0.1401 | 0 | 1 | 0 | N | 1 | 0 | 0 | 1 | 1 | 0 | 1 | 1 | 0 | 2 | 1 | 3 | 0 | 3 | — | — | — | — |
| | | 0.0701 | 0 | 1 | 0 | 0 | 1 | 0 | 0 | 0 | 0 | 0 | N | 0 | 0 | 1 | 1 | 0 | 0 | 0 | — | — | — | — |
| | | 0.0351 | 0 | 0 | 0 | 0 | 1 | 0 | 0 | 0 | 0 | 0 | 0 | 0 | 0 | 0 | 0 | 0 | 0 | 0 | — | — | — | — |
| | | 0.0175 | 0 | 1 | 0 | 0 | 0 | 0 | 0 | 0 | 0 | 0 | 0 | 0 | 0 | 0 | 0 | 0 | 0 | 0 | — | — | — | — |

-continued

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| | | 0.0087 | N | N | 0 | 0 | 1 | 0 | 0 | 0 | 0 | N | N | N | 0 | N | 1 | 0 | 2 | 0 | — | — | — | — |
| 99 | | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | | 1.1210 | 1 | — | — | 0 | 3 | 3 | 3 | — | 3 | 3 | 3 | 3 | 3 | 3 | 3 | 3 | 3 | 3 | 3 | 3 | 3 | — |
| | | 0.5605 | 0 | — | — | 1 | 3 | 3 | 3 | — | 3 | 1 | 3 | 3 | 1 | 3 | 3 | 3 | 3 | 3 | 3 | 3 | 3 | — |
| | | 0.2803 | 0 | — | — | 0 | 2 | 0 | 0 | — | 0 | 1 | 3 | 3 | 0 | 3 | 3 | 3 | 3 | 3 | 3 | 3 | 3 | — |
| | | 0.1401 | 0 | — | — | 1 | 3 | 0 | 0 | — | 0 | 1 | 3 | 3 | 0 | 3 | 3 | 3 | 2 | 3 | 2 | 3 | 3 | — |
| | | 0.0701 | N | — | — | N | 1 | 0 | 0 | — | 0 | 0 | 1 | 0 | 0 | 3 | 3 | 0 | 3 | 2 | 0 | 0 | 0 | — |
| | | 0.0350 | 0 | — | — | N | N | 0 | N | — | 0 | 0 | N | 0 | 0 | 3 | 1 | 0 | 3 | 1 | N | N | N | — |
| | | 0.0175 | N | — | — | N | 0 | 0 | 0 | — | 0 | 0 | 0 | 0 | 0 | 2 | 0 | 0 | 3 | 2 | 0 | 2 | 1 | — |
| | | 0.0087 | 0 | — | — | 0 | 1 | 0 | 0 | — | 0 | 0 | 0 | 0 | 0 | 0 | 0 | 0 | 0 | 0 | 0 | 1 | 1 | — |
| 100 | | 5.6050 | 3 | — | — | 1 | 3 | 3 | 3 | — | 3 | 3 | 3 | 3 | 3 | 3 | 3 | 3 | 3 | 3 | 3 | 3 | 3 | — |
| | | 1.1210 | 0 | — | — | 1 | 3 | 1 | 1 | — | 0 | 0 | 3 | 3 | 0 | 3 | 3 | 3 | 3 | 3 | 1 | 3 | 3 | — |
| | | 0.5605 | 0 | — | — | 1 | 0 | 0 | 0 | — | 0 | 1 | 3 | 3 | 0 | 3 | 3 | 3 | 3 | 3 | 0 | 2 | 3 | — |
| | | 0.2803 | 0 | — | — | 0 | 1 | 0 | 0 | — | 0 | 0 | 0 | 0 | 0 | 3 | 2 | 0 | 3 | 3 | 1 | 2 | 0 | — |
| | | 0.1401 | 0 | — | — | 0 | 0 | 0 | 0 | — | 0 | 0 | 0 | 0 | 0 | 3 | 0 | 0 | 3 | 0 | 0 | 3 | N | — |
| | | 0.0701 | 0 | — | — | 1 | N | 0 | 0 | — | N | 0 | 0 | 1 | 0 | 1 | 1 | 0 | 1 | 0 | N | 3 | N | — |
| | | 0.0350 | 0 | — | — | 1 | N | 0 | 0 | — | 0 | 0 | 0 | 0 | 0 | 1 | 0 | 0 | 1 | 0 | 2 | 3 | 1 | — |
| | | 0.0175 | 0 | — | — | N | 0 | 0 | 0 | — | 0 | 0 | 0 | 0 | 0 | 0 | 0 | 0 | 0 | 0 | 0 | 2 | 1 | — |
| | | 0.0087 | 0 | — | — | N | 0 | 0 | 0 | — | 0 | 0 | 0 | 0 | 0 | 0 | 0 | 0 | N | 0 | 0 | 2 | 1 | — |
| 101 | M | 11.2100 | 3 | — | — | 2 | 0 | 3 | 3 | — | 3 | 1 | 3 | 3 | 3 | 3 | 3 | 3 | 3 | 3 | 1 | 2 | 3 | — |
| | M | 5.6050 | 0 | — | — | 2 | 0 | 3 | 2 | — | 1 | 1 | 3 | 2 | 1 | 3 | 3 | 3 | 3 | 3 | 2 | 2 | 1 | — |
| | M | 2.8025 | 0 | — | — | N | 0 | N | 0 | — | 0 | 0 | 3 | 3 | 1 | 1 | 3 | 3 | 2 | 2 | 0 | 0 | 0 | — |
| | M | 1.1210 | 0 | — | — | 2 | 0 | 1 | 0 | — | 0 | 0 | 0 | 1 | 0 | 0 | 3 | 3 | 1 | 3 | 0 | 1 | 0 | — |
| 102 | | 5.6050 | 2 | — | — | 0 | 1 | 0 | 3 | — | 2 | 2 | 3 | 3 | 2 | 3 | 3 | 3 | 3 | 3 | 2 | 3 | 2 | — |
| | | 1.1210 | 0 | — | — | 0 | 0 | 1 | 0 | — | 0 | 2 | 3 | 3 | 0 | 1 | 3 | 3 | 2 | 3 | 1 | 0 | 0 | — |
| | | 0.5605 | 0 | — | — | 0 | 0 | 0 | 0 | — | 0 | 0 | 0 | 0 | 0 | 0 | 0 | 3 | 0 | 3 | 1 | 1 | 1 | — |
| | | 0.2803 | N | — | — | 0 | 0 | 0 | 0 | — | 0 | 0 | 0 | 0 | 0 | 1 | 0 | 0 | 0 | 0 | 0 | 0 | 0 | — |
| | | 0.1401 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0701 | 0 | — | — | 0 | 0 | 0 | 0 | — | 0 | 0 | 0 | 0 | 0 | 0 | 0 | 0 | 0 | 0 | 0 | 0 | 1 | — |
| | | 0.0350 | 1 | — | — | 0 | 0 | 0 | 0 | — | 0 | 0 | 0 | 0 | 0 | 0 | 0 | 0 | 0 | 0 | N | 0 | 0 | — |
| | | 0.0175 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0087 | 0 | — | — | 0 | 0 | 0 | 0 | — | 0 | 0 | 0 | 0 | 0 | 0 | 0 | 0 | 1 | 0 | 0 | 0 | 0 | — |
| 103 | | 5.6050 | 1 | — | — | 0 | 3 | 3 | 3 | — | 3 | 3 | 3 | 3 | 3 | 3 | 3 | 3 | 3 | 3 | 3 | 3 | 3 | — |
| | | 1.1210 | 0 | — | — | 0 | 1 | 1 | 2 | — | 0 | 0 | 3 | 2 | 0 | 3 | 3 | 3 | 3 | 1 | 1 | N | 3 | — |
| | | 0.5605 | 0 | — | — | 0 | 2 | 3 | 3 | — | 0 | 0 | 3 | 3 | 0 | 1 | 2 | 3 | 3 | 0 | 0 | 3 | 3 | — |
| | | 0.2803 | 0 | — | — | 0 | 2 | 0 | N | — | 0 | 0 | 1 | 0 | 0 | 2 | 0 | 0 | 3 | 0 | 1 | 2 | 3 | — |
| | | 0.1401 | 0 | — | — | N | N | 0 | 0 | — | 0 | 0 | 1 | 0 | 0 | 0 | 0 | 0 | 1 | 0 | 0 | N | 3 | — |
| | | 0.0701 | 0 | — | — | 1 | 0 | 1 | 0 | — | 0 | 0 | 0 | 2 | 0 | 0 | N | 0 | 2 | 0 | N | 0 | 1 | — |
| 104 | | 5.6050 | 0 | — | — | 0 | 0 | 0 | 3 | — | 1 | 1 | 3 | 3 | 3 | 2 | 3 | 3 | 3 | 3 | 1 | 3 | 3 | — |
| | | 1.1210 | 0 | — | — | 0 | 0 | 1 | 0 | — | 0 | 0 | 0 | 0 | 0 | 0 | 0 | 3 | 0 | 0 | 2 | 1 | 1 | — |
| | | 0.5605 | 0 | — | — | 0 | 2 | 0 | 1 | — | 0 | 0 | 0 | 0 | 0 | 0 | 0 | 0 | 2 | 0 | N | N | 2 | — |
| | | 0.2803 | 0 | — | — | 0 | 0 | 0 | N | — | N | 0 | 2 | 0 | 0 | 3 | 3 | 0 | 2 | 0 | 1 | 0 | 3 | — |
| | | 0.1401 | 0 | — | — | 0 | 0 | 0 | 0 | — | 0 | 0 | 0 | 0 | 0 | 0 | 0 | 0 | 0 | 0 | 2 | 2 | 3 | — |
| | | 0.0701 | 0 | — | — | 0 | 0 | 0 | 0 | — | 0 | 0 | 0 | 0 | 0 | 0 | 0 | 0 | 0 | 0 | 0 | 0 | 3 | — |
| 105 | | 5.6050 | 1 | — | — | 0 | 3 | 1 | 1 | — | 1 | 2 | 3 | 3 | 2 | 3 | 3 | 3 | 3 | 3 | 3 | 3 | 3 | — |
| | | 1.1210 | 0 | — | — | 0 | 3 | 0 | 1 | — | 1 | 0 | 2 | 2 | 0 | 3 | 1 | 3 | 3 | 3 | 3 | 3 | 3 | — |
| | | 0.5605 | 0 | — | — | 0 | 3 | 0 | 1 | — | 0 | 0 | 1 | 0 | 0 | 0 | 1 | 0 | 1 | 0 | 2 | 3 | 1 | — |
| | | 0.2803 | N | — | — | 0 | 3 | 0 | N | — | 0 | 0 | 0 | 0 | 0 | 0 | 0 | 0 | 0 | 0 | N | 3 | 1 | — |
| | | 0.1401 | 0 | — | — | 0 | 1 | 0 | 0 | — | 0 | 0 | 0 | 0 | 0 | N | 0 | 0 | N | 0 | 0 | 1 | N | — |
| | | 0.0701 | 0 | — | — | 0 | N | 0 | 0 | — | 0 | 0 | 0 | 0 | 0 | 0 | 0 | 0 | 1 | 0 | N | N | N | — |
| 106 | | 5.6050 | 1 | — | — | 1 | 3 | 3 | 3 | — | 3 | 3 | 3 | 3 | 3 | 3 | 3 | 3 | 3 | 3 | 3 | 3 | 3 | — |
| | | 1.1210 | 2 | — | — | 1 | 3 | 3 | 1 | — | 1 | 3 | 3 | 3 | 3 | 3 | 3 | 3 | 3 | 3 | 3 | 2 | 2 | — |

-continued

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| | | 0.5605 | 0 | — | — | 0 | 0 | 0 | 1 | — | 0 | 3 | 3 | 3 | 2 | 3 | 3 | 3 | 3 | 3 | 3 | 1 | 3 | — |
| | | 0.2803 | 0 | — | — | 0 | 0 | 0 | 1 | — | 0 | 1 | 3 | 3 | 0 | 3 | 3 | 3 | 3 | 3 | 0 | 0 | 1 | — |
| | | 0.1401 | 0 | — | — | 0 | 0 | 0 | 0 | — | 0 | 0 | 2 | 3 | 0 | 3 | 3 | 3 | 3 | 3 | 0 | 0 | 0 | — |
| | | 0.0701 | N | — | — | 0 | N | 0 | 0 | — | 0 | 2 | 0 | 2 | 1 | 0 | 2 | 1 | 0 | 0 | 0 | 1 | 1 | — |
| | | 0.0350 | 0 | — | — | 0 | 0 | 0 | 0 | — | 0 | 0 | 0 | 0 | 0 | 2 | 0 | 0 | N | 0 | N | N | 1 | — |
| | | 0.0175 | 0 | — | — | 0 | 0 | 0 | 0 | — | 0 | 0 | 0 | 0 | 0 | 0 | 0 | 0 | 0 | 0 | 0 | N | 0 | — |
| | | 0.0087 | N | — | — | 0 | 1 | 0 | 0 | — | 0 | 0 | 0 | 0 | 0 | 1 | 0 | 0 | 0 | 0 | 0 | 1 | 0 | — |
| 107 | | 5.6050 | 2 | — | — | 3 | 0 | 2 | 1 | — | 0 | 3 | 2 | 3 | 3 | 3 | 3 | 3 | 3 | 3 | 3 | 0 | 2 | — |
| | | 1.1210 | 0 | — | — | 0 | 0 | 1 | 0 | — | 0 | 0 | 0 | 2 | 0 | 0 | 0 | 3 | 3 | 3 | 0 | 0 | 1 | — |
| | | 0.5605 | 0 | — | — | N | 0 | 0 | 0 | — | 0 | 0 | 0 | 0 | 0 | 0 | 0 | 0 | 3 | 0 | 0 | 0 | 1 | — |
| | | 0.2803 | 0 | — | — | 0 | N | 0 | 0 | — | 0 | 0 | 0 | 0 | 0 | 0 | 0 | 0 | N | 0 | 0 | N | 1 | — |
| | | 0.1401 | 0 | — | — | 0 | 0 | 0 | 0 | — | 0 | 0 | 0 | 0 | 0 | 0 | 0 | 0 | 2 | 0 | 0 | 0 | 1 | — |
| | | 0.0701 | 0 | — | — | 0 | 0 | 0 | 0 | — | 0 | 0 | 0 | 0 | 0 | 0 | 0 | 0 | N | 0 | 0 | N | 1 | — |
| 108 | | 5.6050 | 3 | — | — | 0 | 3 | 3 | 3 | — | 3 | 3 | 3 | 3 | 3 | 3 | 3 | 3 | 3 | 3 | 3 | 3 | 3 | — |
| | | 1.1210 | 0 | — | — | 0 | 0 | 3 | 3 | — | 3 | 2 | 3 | 3 | 2 | 3 | 3 | 3 | 3 | 3 | 3 | 0 | 3 | — |
| | | 0.5605 | 0 | — | — | 0 | N | 2 | 1 | — | 1 | 1 | 3 | 3 | 1 | 3 | 3 | 3 | 3 | 3 | 1 | 1 | 2 | — |
| | | 0.2803 | 0 | — | — | 0 | 0 | 2 | 0 | — | 0 | 1 | 2 | 3 | 0 | 3 | 3 | 3 | 3 | 3 | 0 | 0 | 0 | — |
| | | 0.1401 | 1 | — | — | 0 | 0 | 1 | 0 | — | 0 | 0 | 0 | 2 | 0 | 2 | 0 | 3 | 3 | 2 | 0 | 0 | 2 | — |
| | | 0.0701 | 0 | — | — | 1 | 1 | 0 | 0 | — | 0 | 0 | 0 | 1 | 0 | 1 | 0 | 0 | 0 | 0 | 0 | 0 | 2 | — |
| | | 0.0350 | 0 | — | — | 0 | 0 | 0 | 0 | — | 0 | 0 | 0 | 0 | 0 | 0 | 0 | 0 | 1 | 0 | 0 | 0 | 1 | — |
| | | 0.0175 | 0 | — | — | 0 | 0 | 0 | 0 | — | 0 | 0 | 0 | 0 | 0 | 0 | 0 | 0 | 0 | 0 | 0 | 0 | 0 | — |
| 109 | | 5.6050 | 3 | — | — | 0 | 3 | 0 | 3 | — | 3 | 3 | 3 | 3 | 3 | 3 | 3 | 3 | 3 | 3 | 3 | 3 | 3 | — |
| | | 1.1210 | 0 | — | — | 0 | 1 | 2 | 1 | — | 0 | 2 | 1 | 3 | 2 | 2 | 3 | 3 | 3 | 3 | 2 | 3 | 3 | — |
| | | 0.5605 | 0 | — | — | 0 | 1 | 1 | 0 | — | 0 | 0 | 1 | 1 | 0 | 2 | 3 | 3 | 3 | 3 | 1 | 3 | 1 | — |
| | | 0.2803 | 0 | — | — | 0 | 0 | 0 | 0 | — | 0 | 0 | 0 | 1 | 0 | 0 | 0 | 3 | 2 | 2 | 0 | 0 | 0 | — |
| | | 0.1401 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0701 | 0 | — | — | 0 | N | 0 | 0 | — | 0 | 0 | 0 | 0 | 0 | 0 | 0 | 0 | 0 | 0 | 0 | N | 1 | — |
| | | 0.0350 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0175 | 0 | — | — | 0 | 0 | 0 | 0 | — | 0 | 0 | 0 | 0 | 0 | 0 | 0 | 0 | 0 | 0 | 0 | N | 0 | — |
| 110 | J | 5.6050 | 3 | — | — | 2 | 3 | 3 | 3 | — | 3 | 3 | 3 | 3 | 3 | 3 | 3 | 3 | 3 | 3 | 3 | 3 | 3 | — |
| | J | 1.1210 | 0 | — | — | 0 | 3 | 0 | 2 | — | 1 | 2 | 3 | 3 | 1 | 3 | 3 | 3 | 3 | 3 | 3 | 3 | 3 | — |
| | J | 0.5605 | 0 | — | — | 0 | 2 | 0 | 0 | — | 0 | 0 | 1 | 1 | 2 | 3 | 3 | 3 | 3 | 3 | 3 | 3 | 3 | — |
| | J | 0.2803 | 0 | — | — | 1 | 1 | 0 | 0 | — | 0 | 0 | 0 | 1 | 0 | 3 | 2 | 1 | 3 | 1 | 1 | 3 | 1 | — |
| | J | 0.1401 | 0 | — | — | 1 | 2 | 1 | 1 | — | 0 | 0 | 0 | 0 | 0 | 1 | 0 | 0 | 3 | 0 | 0 | 3 | 1 | — |
| | J | 0.0701 | 0 | — | — | 0 | 1 | 0 | 0 | — | 0 | 0 | 0 | 0 | 0 | 0 | 0 | 0 | 1 | 0 | 1 | 2 | 1 | — |
| | J | 0.0350 | 0 | — | — | 0 | 1 | 0 | 0 | — | 0 | 0 | 0 | 0 | 0 | 0 | 0 | 0 | 2 | 0 | 0 | 0 | 0 | — |
| | J | 0.0175 | 0 | — | — | 0 | 0 | 0 | 0 | — | 0 | 0 | 0 | 0 | 0 | 1 | 0 | 0 | 0 | 0 | 0 | N | 1 | — |
| 111 | J | 5.6050 | 3 | — | — | 2 | 3 | 3 | 3 | — | 3 | 3 | 3 | 3 | 3 | 3 | 3 | 3 | 3 | 3 | 3 | 3 | 3 | — |
| | J | 1.1210 | 0 | — | — | 0 | 3 | 3 | 3 | — | 2 | 3 | 3 | 3 | 2 | 3 | 3 | 3 | 3 | 3 | 3 | 3 | 3 | — |
| | J | 0.5605 | 0 | — | — | 1 | 3 | 3 | 1 | — | 1 | 0 | 3 | 3 | 2 | 3 | 3 | 3 | 3 | 3 | 1 | 3 | 3 | — |
| | J | 0.2803 | 1 | — | — | 0 | 3 | 0 | 2 | — | 0 | 0 | 3 | 2 | 0 | 3 | 3 | 3 | 3 | 3 | 2 | 3 | 3 | — |
| | J | 0.1401 | 0 | — | — | 0 | 3 | 1 | 1 | — | 0 | 0 | 3 | 1 | 0 | 3 | 3 | 3 | 3 | 3 | 3 | 3 | 3 | — |
| | J | 0.0701 | 0 | — | — | 0 | 3 | 0 | 0 | — | 0 | 0 | 3 | 1 | 0 | 0 | 2 | 0 | 0 | 3 | 3 | 3 | 3 | — |
| | J | 0.0350 | 0 | — | — | 0 | 3 | 0 | N | — | 0 | 0 | 0 | 0 | 0 | 0 | 0 | 0 | 0 | 0 | 3 | 3 | 3 | — |
| | J | 0.0175 | 0 | — | — | 0 | 2 | 0 | 0 | — | 0 | 0 | N | 0 | 0 | 0 | 0 | 0 | 0 | 0 | 1 | 1 | 3 | — |
| | J | 0.0087 | 0 | — | — | 0 | 1 | 0 | N | — | 0 | 0 | 0 | 0 | 0 | 0 | 0 | 0 | 0 | 0 | 1 | 3 | 2 | — |
| 112 | | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | | 1.1210 | 3 | — | — | 1 | 3 | 3 | 3 | — | 3 | 3 | 3 | 3 | 3 | 3 | 3 | 3 | 3 | 3 | 3 | 3 | 3 | — |
| | | 0.5605 | 2 | — | — | 1 | 3 | 3 | 3 | — | 3 | 3 | 3 | 3 | 3 | 3 | 3 | 3 | 3 | 3 | 3 | 3 | 3 | — |
| | | 0.2803 | 3 | — | — | 0 | 3 | 3 | 3 | — | 3 | 3 | 3 | 3 | 3 | 3 | 3 | 3 | 3 | 3 | 3 | 3 | 3 | — |
| | | 0.1401 | 0 | — | — | 1 | 0 | 3 | 3 | — | 0 | 1 | 3 | 3 | 0 | 3 | 3 | 3 | 3 | 3 | 1 | 0 | 3 | — |
| | | 0.0701 | 1 | — | — | N | 0 | 0 | 0 | — | 0 | 3 | 3 | 3 | 0 | 3 | 3 | 3 | 3 | 3 | N | 0 | 3 | — |

-continued

TABLE 3-continued

| | | | | | | | | | | | | | | | | | | | | | | | |
|---|---|---|---|---|---|---|---|---|---|---|---|---|---|---|---|---|---|---|---|---|---|---|---|---|
| | | 0.0350 | 1 | — | — | 0 | 0 | 0 | 0 | — | 0 | 1 | 3 | 3 | 0 | 1 | 3 | 3 | 0 | 3 | 0 | 0 | 0 | — |
| | | 0.0175 | 0 | — | — | 0 | 1 | 0 | 0 | — | 0 | 0 | 0 | 0 | 0 | 0 | 0 | 1 | 0 | 2 | 0 | N | 1 | — |
| | | 0.0087 | N | — | — | 0 | 2 | 0 | 0 | — | 0 | 0 | 0 | 0 | N | 0 | 0 | 1 | 0 | 2 | 1 | N | N | — |
| | | 0.0044 | 0 | — | — | 0 | 0 | 0 | 0 | — | 0 | 0 | 0 | 0 | 0 | 1 | 0 | 0 | 0 | 2 | 0 | 0 | N | — |
| 113 | | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | | 1.1210 | 0 | — | — | 3 | N | 3 | 3 | — | 3 | 3 | 3 | 3 | 3 | 3 | 3 | 3 | 3 | 3 | 1 | 3 | 3 | — |
| | | 0.5605 | 1 | — | — | 1 | 3 | 3 | 2 | — | 3 | 3 | 3 | 3 | 1 | 3 | 3 | 3 | 3 | 3 | 2 | 3 | 3 | — |
| | | 0.2803 | N | — | — | N | 3 | 3 | 0 | — | 1 | 3 | 3 | 3 | 0 | 3 | 3 | 3 | 3 | 3 | 1 | 0 | 1 | — |
| | | 0.1401 | 0 | — | — | 2 | N | 0 | N | — | 1 | 1 | 3 | 2 | 0 | 2 | 3 | 3 | 3 | 3 | 1 | N | 2 | — |
| | | 0.0701 | 0 | — | — | N | 2 | 2 | 0 | — | 1 | 0 | 1 | 0 | 0 | 0 | 1 | 1 | 0 | 2 | 1 | 0 | 0 | — |
| | | 0.0350 | N | — | — | 0 | N | 2 | 0 | — | 0 | 0 | 1 | 0 | 0 | 0 | 1 | 0 | 2 | 2 | 0 | N | 0 | — |
| | | 0.0175 | 0 | — | — | N | N | 1 | 0 | — | 0 | 0 | 0 | 1 | 0 | 0 | 0 | 0 | 3 | 0 | 0 | N | N | — |
| | | 0.0087 | 1 | — | — | 1 | N | 0 | 1 | — | 0 | 0 | 0 | 0 | 0 | 0 | 0 | 0 | 0 | 0 | N | N | N | — |
| 114 | | 5.6050 | 2 | — | — | 0 | 1 | 0 | 0 | — | 0 | 3 | 3 | 3 | 3 | 3 | 3 | 3 | 3 | 3 | 0 | 3 | 1 | — |
| | | 1.1210 | 0 | — | — | 0 | 1 | 1 | 0 | — | 0 | 0 | 3 | 1 | 0 | 3 | 3 | 3 | 3 | 3 | 1 | 2 | 1 | — |
| | | 0.5605 | 0 | — | — | 0 | 0 | 0 | N | — | 0 | 0 | 3 | 0 | 0 | 3 | 3 | 0 | 3 | 2 | 1 | N | 0 | — |
| | | 0.2803 | 0 | — | — | 1 | 0 | 0 | 0 | — | N | 0 | 2 | 0 | 0 | 0 | N | 0 | 1 | 0 | 0 | 0 | 3 | — |
| | | 0.1401 | 1 | — | — | 0 | 1 | 2 | 0 | — | 0 | 0 | 3 | 0 | 0 | 1 | 3 | 0 | 2 | 0 | 0 | N | 0 | — |
| | | 0.0701 | 0 | — | — | 0 | 0 | 0 | 0 | — | 0 | 0 | 0 | 0 | 0 | 0 | 0 | 0 | 0 | 0 | 0 | 0 | 1 | — |
| | | 0.0350 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0175 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0087 | 0 | — | — | N | 0 | N | 1 | — | 0 | 0 | 0 | 0 | 0 | 0 | 0 | 0 | 0 | 0 | 1 | 0 | 0 | — |
| 115 | | 5.6050 | 3 | — | — | 3 | 3 | 3 | 3 | — | 3 | 3 | 3 | 3 | 3 | 3 | 3 | 3 | 3 | 3 | 3 | 3 | 3 | — |
| | | 1.1210 | 2 | — | — | N | 3 | 3 | N | — | 3 | 2 | 3 | 3 | 3 | 3 | 3 | 3 | 3 | 3 | 3 | 3 | 3 | — |
| | | 0.5605 | 1 | — | — | 3 | 1 | 3 | 3 | — | 3 | 3 | 3 | 3 | 3 | 3 | 3 | 3 | 3 | 3 | 2 | 2 | 3 | — |
| | | 0.2803 | 0 | — | — | 0 | 0 | 1 | 1 | — | 1 | 1 | 3 | 3 | 1 | 3 | 3 | 3 | 3 | 3 | 1 | 3 | 3 | — |
| | | 0.1401 | 2 | — | — | N | 1 | 0 | 1 | — | 0 | 0 | 3 | 3 | 2 | 0 | 3 | 3 | 0 | 3 | 0 | 0 | 0 | — |
| | | 0.0701 | 0 | — | — | 0 | 0 | 1 | 0 | — | 0 | 0 | 2 | 0 | 0 | 0 | 0 | 3 | 0 | 3 | 0 | 0 | 0 | — |
| | | 0.0350 | 0 | — | — | 0 | N | 0 | 0 | — | 0 | 0 | 1 | 0 | 0 | 1 | 0 | 0 | N | 0 | 0 | N | 0 | — |
| | | 0.0175 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0087 | 0 | — | — | N | N | 0 | 0 | — | 0 | 0 | 0 | 0 | 0 | 0 | 0 | 0 | 0 | 0 | 0 | 0 | 0 | — |
| | | 0.0044 | 0 | — | — | 0 | 0 | 0 | 0 | — | 0 | 0 | 0 | 0 | 0 | 0 | 0 | 0 | 0 | 0 | 0 | 0 | 0 | — |
| 117 | | 5.6050 | 0 | — | — | 0 | 0 | 0 | 1 | — | 1 | 2 | 3 | 3 | 3 | 3 | 3 | 3 | 3 | 3 | 3 | 3 | 3 | — |
| | | 1.1210 | 0 | — | — | 0 | 0 | 0 | 0 | — | 0 | 1 | 2 | 3 | 0 | 0 | 3 | 3 | 1 | 0 | 1 | 0 | 0 | — |
| | | 0.5605 | 0 | — | — | 0 | 0 | 0 | 0 | — | 0 | 1 | 0 | 3 | 0 | 0 | 3 | 3 | N | 0 | 0 | 0 | 0 | — |
| | | 0.2803 | 0 | — | — | 0 | 0 | 0 | 0 | — | 0 | 0 | 0 | 0 | 0 | 0 | 0 | 1 | 2 | 0 | 0 | 0 | 0 | — |
| | | 0.1401 | 0 | — | — | 0 | N | 0 | 0 | — | 0 | 0 | 0 | 0 | 0 | 0 | 2 | 0 | 0 | 0 | 0 | 0 | 0 | — |
| | | 0.0701 | 0 | — | — | 0 | 0 | 0 | 0 | — | 0 | 0 | 0 | 0 | 0 | 0 | 0 | 0 | 0 | 0 | 0 | 0 | 0 | — |
| 119 | N | 5.6050 | 0 | — | — | 0 | 1 | 0 | 1 | — | 0 | 0 | 3 | 3 | 1 | 3 | 3 | 3 | 3 | 3 | 3 | 3 | 3 | — |
| | N | 1.1210 | 1 | — | — | 0 | 0 | N | 0 | — | 0 | 0 | 0 | 3 | 1 | 0 | 0 | 0 | 3 | 3 | 0 | 0 | 0 | — |
| | N | 0.5605 | 0 | — | — | 0 | 0 | 1 | 0 | — | 0 | 0 | 0 | 0 | 0 | 0 | 0 | 0 | 0 | 1 | 0 | 0 | 0 | — |
| | N | 0.2803 | 1 | — | — | 0 | N | N | 1 | — | 0 | 0 | 0 | 0 | 0 | 0 | 0 | 1 | 0 | 2 | 0 | 1 | 0 | — |
| | N | 0.1401 | 1 | — | — | 0 | 0 | 0 | 0 | — | 0 | 0 | 0 | 0 | 0 | 0 | 0 | 0 | 0 | 1 | 0 | 0 | 0 | — |
| | N | 0.0701 | N | — | — | 0 | 0 | N | 0 | — | 0 | 0 | 0 | 0 | 0 | 0 | 0 | 0 | 0 | 0 | 0 | 0 | 0 | — |
| 120 | | 5.6050 | 0 | — | — | 0 | 0 | 3 | 0 | — | 0 | 0 | 1 | 3 | 1 | 0 | 3 | 3 | 3 | 3 | 2 | 0 | 3 | — |
| | | 1.1210 | 1 | — | — | 0 | N | 0 | N | — | 0 | 0 | 1 | 3 | 0 | 0 | 3 | 3 | 3 | 3 | N | N | 3 | — |
| | | 0.5605 | 0 | — | — | 0 | 0 | 0 | 0 | — | 0 | 0 | 0 | 3 | 0 | 0 | 3 | 3 | 3 | 3 | 0 | 1 | 3 | — |
| | | 0.2803 | 1 | — | — | 0 | 1 | 1 | 1 | — | 1 | 0 | 0 | 1 | 0 | 0 | 1 | 3 | 3 | 3 | 1 | N | N | — |
| | | 0.1401 | 0 | — | — | 0 | 0 | 0 | 0 | — | 0 | 0 | 0 | 0 | 0 | 0 | 0 | 0 | 1 | 0 | 1 | 0 | 1 | — |
| | | 0.0701 | 0 | — | — | 0 | 0 | 0 | 0 | — | 0 | 0 | 0 | 0 | 0 | N | 0 | 0 | 2 | 0 | 0 | 0 | 0 | — |
| | | 0.0350 | 0 | — | — | 0 | N | 0 | 1 | — | 0 | 0 | 0 | 0 | 0 | 0 | 0 | N | 0 | N | 1 | 1 | 0 | — |
| 121 | | 11.2100 | 1 | 0 | 2 | 0 | 0 | 0 | 0 | 1 | 1 | 1 | 0 | 1 | 0 | 0 | 2 | 0 | 1 | 0 | — | — | — | — |

-continued

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| | | 5.6050 | 2 | N | 1 | N | N | 1 | 0 | 1 | 1 | N | 1 | N | N | 0 | 1 | 1 | 1 | 1 | — | — | — | — |
| 123 | | 11.2100 | 2 | — | — | 2 | 0 | 1 | 3 | — | 3 | 3 | 3 | 3 | 2 | 3 | 3 | 3 | 3 | 3 | 3 | 3 | 3 | — |
| | | 5.6050 | 0 | — | — | 0 | N | 0 | 3 | — | 2 | 0 | 2 | 3 | 0 | 3 | 3 | 3 | 3 | 3 | 3 | 3 | 3 | — |
| | | 2.8025 | 0 | — | — | N | 0 | 1 | 2 | — | 0 | 0 | 1 | 3 | 0 | 1 | 3 | 3 | 3 | 3 | 1 | 3 | 3 | — |
| | | 1.1210 | 0 | — | — | N | 0 | 1 | 0 | — | 0 | 0 | 0 | 0 | 0 | 0 | 0 | 1 | 3 | 3 | 0 | 0 | 0 | — |
| | | 0.5605 | 0 | — | — | 1 | 0 | 1 | 0 | — | 0 | 0 | 0 | 0 | 0 | 0 | 0 | 0 | 3 | 2 | 0 | N | 0 | — |
| 124 | | 5.6050 | 0 | — | — | 3 | 1 | 1 | 1 | — | 0 | 3 | 0 | 3 | 2 | 3 | 3 | 3 | 3 | 3 | 3 | 3 | 2 | — |
| | | 1.1210 | 0 | — | — | 0 | 1 | 0 | 0 | — | 0 | 0 | 0 | 0 | 0 | 3 | 0 | 3 | 3 | 3 | 0 | 3 | 0 | — |
| | | 0.5605 | 0 | — | — | N | N | 0 | 0 | — | 0 | 0 | 0 | 0 | 0 | 0 | 0 | 2 | 3 | 2 | N | 3 | N | — |
| | | 0.2803 | 0 | — | — | 1 | 0 | 0 | 0 | — | 0 | 0 | 0 | 0 | 0 | 2 | 0 | 0 | 3 | 0 | 0 | 3 | 0 | — |
| | | 0.1401 | 0 | — | — | 1 | N | 0 | 0 | — | 0 | 0 | 0 | 0 | 0 | 0 | 0 | 0 | 1 | 0 | N | 3 | 1 | — |
| | | 0.0701 | 0 | — | — | N | N | 0 | 0 | — | 0 | 0 | 0 | 0 | 0 | N | N | 0 | N | 0 | 0 | 3 | 0 | — |
| 125 | | 5.6050 | 3 | 3 | 3 | 0 | 3 | 3 | 3 | 3 | 3 | 3 | 3 | 3 | 3 | 3 | 3 | 3 | 3 | 3 | — | — | — | — |
| | | 1.1210 | 0 | 3 | 0 | 0 | 3 | 1 | 2 | 2 | 2 | 2 | 3 | 3 | 0 | 3 | 3 | 3 | 3 | 3 | — | — | — | — |
| | | 0.2803 | 0 | 1 | 0 | 0 | 1 | 0 | 1 | 2 | 1 | 0 | 0 | 0 | 0 | 0 | 0 | 0 | 2 | 0 | — | — | — | — |
| | | 0.0701 | 0 | 2 | 0 | 0 | N | 0 | 0 | N | 0 | 0 | 1 | 0 | 0 | 1 | N | 0 | N | 0 | — | — | — | — |
| 126 | + | 5.6050 | 1 | — | — | 1 | 0 | 3 | 3 | — | 1 | 1 | 3 | 3 | 2 | 2 | 3 | 3 | 3 | 3 | 3 | 3 | N | — |
| | + | 1.1210 | 0 | — | — | N | 0 | 0 | 0 | — | 0 | 0 | 0 | 0 | 0 | 0 | 2 | 3 | 3 | 3 | 0 | 0 | N | — |
| | + | 0.5605 | 0 | — | — | N | N | 0 | 0 | — | 0 | 0 | 0 | 0 | 0 | 1 | 0 | 0 | 2 | 0 | 0 | 1 | N | — |
| | + | 0.2803 | N | — | — | 0 | 0 | 1 | 0 | — | 0 | 0 | 0 | 0 | 0 | 0 | 0 | 0 | 0 | 0 | 0 | N | N | — |
| | + | 0.1401 | 0 | — | — | 0 | 1 | 1 | 1 | — | 0 | 0 | 0 | 0 | 0 | 0 | 0 | 0 | 1 | 0 | 0 | 0 | N | — |
| 127 | | 5.6050 | 3 | 3 | 3 | 3 | 3 | 3 | 3 | 3 | 3 | 3 | 3 | 3 | 3 | 3 | 3 | 3 | 3 | 3 | — | — | — | — |
| | | 1.1210 | 3 | 0 | 3 | 1 | 3 | 3 | 2 | 3 | 3 | 3 | 3 | 3 | 3 | 3 | 3 | 3 | 3 | 3 | — | — | — | — |
| | | 0.2803 | 3 | 1 | 3 | 0 | 2 | 2 | 1 | 2 | 2 | 3 | 3 | 3 | 3 | 3 | 3 | 3 | 3 | 3 | — | — | — | — |
| | | 0.0701 | 0 | 0 | 1 | 1 | 1 | 0 | 1 | 1 | 0 | 2 | 2 | 2 | 0 | 2 | 2 | 3 | 3 | 3 | — | — | — | — |
| | | 0.0175 | 0 | 0 | 0 | 0 | 0 | 0 | 0 | 0 | 0 | 0 | 0 | 1 | 1 | 0 | 1 | 0 | 2 | 0 | — | — | — | — |
| | | 0.0087 | 0 | 1 | 0 | 0 | 0 | 0 | 0 | 1 | 0 | 0 | 0 | 0 | 1 | 0 | 0 | 0 | 1 | 0 | — | — | — | — |
| 129 | | 11.2100 | 0 | 0 | 0 | N | 3 | 0 | 0 | 2 | 0 | 0 | 1 | 0 | 0 | 3 | 3 | 3 | 3 | 3 | — | — | — | — |
| | | 5.6050 | 1 | 0 | 1 | N | 3 | 1 | 0 | 1 | 0 | 1 | 2 | 1 | N | 1 | 2 | 3 | 3 | 3 | — | — | — | — |
| | | 1.1210 | 0 | 0 | N | N | 2 | 0 | 0 | 2 | 0 | 0 | 2 | 0 | 0 | N | 2 | 3 | 3 | 3 | — | — | — | — |
| 130 | | 5.6050 | 2 | 0 | 3 | 0 | 3 | 3 | 3 | 2 | 3 | 3 | 3 | 3 | 3 | 3 | 3 | 3 | 3 | 3 | — | — | — | — |
| | | 1.1210 | 1 | 0 | 0 | 0 | 0 | 0 | 1 | 0 | 3 | 1 | 3 | 0 | 0 | 0 | 3 | 3 | 3 | 3 | — | — | — | — |
| | | 0.2803 | 0 | 0 | 0 | 0 | 0 | 0 | 0 | 0 | 0 | 0 | 0 | 0 | 0 | 0 | 0 | 0 | 1 | 0 | — | — | — | — |
| | | 0.0701 | 0 | 0 | 0 | 0 | 0 | 0 | 0 | 0 | 0 | 0 | 0 | 0 | 0 | 0 | 0 | 0 | 0 | 0 | — | — | — | — |
| 131 | $ | 5.6050 | 2 | 1 | 3 | N | 3 | 3 | 3 | 3 | 1 | 3 | 3 | 3 | 1 | 3 | 3 | 3 | 3 | 3 | — | — | — | — |
| | $ | 1.1210 | 1 | 0 | 3 | N | 3 | 1 | 1 | 3 | 1 | 1 | 3 | 2 | 0 | 3 | 3 | 3 | 3 | 3 | — | — | — | — |
| | $ | 0.2803 | 1 | 1 | 0 | N | 1 | 0 | 1 | 0 | 1 | 1 | 1 | 1 | 1 | 1 | 1 | 1 | 3 | 3 | — | — | — | — |
| | $ | 0.0701 | 0 | 0 | 0 | N | 0 | 0 | 0 | 0 | 0 | 0 | 1 | 0 | 0 | 0 | 1 | 0 | 1 | 0 | — | — | — | — |
| 133 | | 5.6050 | 2 | — | — | 0 | 3 | 3 | 3 | — | 3 | 3 | 3 | 3 | 3 | 3 | 3 | 3 | 3 | 3 | 3 | 3 | 3 | — |
| | | 1.1210 | 0 | — | — | 0 | 3 | 1 | 2 | — | 2 | 0 | 3 | 2 | 0 | 1 | 3 | 3 | 3 | 3 | 1 | 3 | 3 | — |
| | | 0.5605 | 0 | — | — | 0 | 1 | 1 | 1 | — | 0 | 0 | 3 | 2 | 0 | 2 | 3 | 3 | 3 | 3 | 0 | 3 | 3 | — |
| | | 0.2803 | 0 | — | — | 0 | 1 | 0 | 0 | — | 0 | 0 | 1 | 0 | 0 | 1 | 3 | 3 | 3 | 3 | 0 | 3 | 3 | — |
| | | 0.1401 | 0 | — | — | 0 | 1 | 0 | 0 | — | 0 | 0 | 2 | 0 | 0 | 0 | 0 | 1 | 3 | 3 | 0 | 0 | 2 | — |
| | | 0.0701 | 0 | — | — | 0 | 2 | 0 | 0 | — | 0 | 0 | 0 | 0 | 0 | 0 | 0 | 2 | 2 | 3 | 0 | N | 3 | — |
| | | 0.0350 | 0 | — | — | 0 | 0 | 0 | 0 | — | 0 | 0 | 0 | 0 | 0 | 0 | 0 | 0 | 0 | 0 | 0 | 0 | 0 | — |
| | | 0.0175 | 0 | — | — | 0 | 1 | 0 | 0 | — | 0 | 0 | 0 | 0 | 0 | 0 | 0 | 0 | 1 | 0 | 0 | 1 | 1 | — |
| 134 | | 5.6050 | 3 | — | — | 2 | 3 | 3 | 3 | — | 3 | 3 | 3 | 3 | 3 | 3 | 3 | 3 | 3 | 3 | 3 | 3 | 3 | — |
| | | 1.1210 | 3 | — | — | 1 | 3 | 3 | 3 | — | 3 | 3 | 3 | 3 | 3 | 3 | 3 | 3 | 3 | 3 | 3 | 3 | 3 | — |
| | | 0.5605 | 2 | — | — | 0 | 3 | 3 | 3 | — | 3 | 3 | 3 | 3 | 3 | 3 | 3 | 3 | 3 | 3 | 3 | 3 | 3 | — |
| | | 0.2803 | 1 | — | — | 0 | 3 | 1 | 1 | — | 1 | 3 | 3 | 3 | 1 | 3 | 3 | 3 | 3 | 3 | 3 | 3 | 3 | — |
| | | 0.1401 | 0 | — | — | 0 | 3 | 1 | 3 | — | 2 | 0 | 2 | 3 | 1 | 3 | 3 | 3 | 3 | 3 | 3 | 3 | 3 | — |
| | | 0.0701 | 0 | — | — | 0 | 3 | 0 | 0 | — | 0 | 1 | 1 | 1 | 0 | 3 | 2 | 1 | 3 | 2 | 0 | 3 | 1 | — |

-continued

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| | | 0.0350 | 0 | — | — | 0 | 0 | 0 | 0 | — | 0 | 0 | 0 | 1 | 0 | 1 | 0 | 0 | 3 | 2 | 0 | 2 | 1 | — |
| | | 0.0175 | 0 | — | — | 0 | 0 | 0 | 0 | — | 0 | 0 | 0 | 0 | 0 | 0 | 0 | 0 | 0 | 0 | 1 | 0 | 0 | — |
| | | 0.0087 | 0 | — | — | 0 | N | 0 | 0 | — | 0 | N | 0 | 0 | 0 | 0 | 0 | 0 | 0 | 0 | N | N | 1 | — |
| 135 | | 5.6050 | 3 | — | — | 0 | 3 | 3 | 3 | — | 3 | 3 | 3 | 3 | 3 | 3 | 3 | 3 | 3 | 3 | 3 | 3 | 3 | — |
| | | 1.1210 | 2 | — | — | 0 | 3 | 3 | 3 | — | 3 | 3 | 3 | 3 | 3 | 3 | 3 | 3 | 3 | 3 | 3 | 3 | 3 | — |
| | | 0.5605 | 3 | — | — | 0 | 2 | 3 | 1 | — | 3 | 3 | 3 | 3 | 3 | 3 | 3 | 3 | 3 | 3 | 3 | 3 | 3 | — |
| | | 0.2803 | 1 | — | — | 0 | 0 | 2 | 1 | — | 0 | 3 | 3 | 3 | 3 | 3 | 3 | 3 | 3 | 3 | 3 | 0 | 3 | — |
| | | 0.0701 | 0 | — | — | 0 | 0 | 0 | 0 | — | 0 | 2 | 1 | 1 | 0 | 3 | 0 | 3 | 3 | 3 | 0 | 0 | 0 | — |
| | | 0.0350 | 0 | — | — | 0 | 0 | 0 | 0 | — | 0 | 0 | 1 | 0 | 0 | 1 | 0 | 0 | 3 | 2 | 0 | N | 0 | — |
| | | 0.0175 | 0 | — | — | N | N | N | 0 | — | 0 | 0 | 0 | 0 | 0 | 0 | 0 | 0 | 1 | 0 | 0 | 1 | 0 | — |
| | | 0.0087 | 0 | — | — | 0 | 0 | 1 | 0 | — | 0 | 0 | 0 | 0 | 0 | 0 | 0 | 0 | 0 | 0 | 0 | 0 | N | — |
| | | 0.0044 | 0 | — | — | 0 | 0 | 0 | 0 | — | 0 | 0 | 0 | 0 | 0 | 0 | 0 | 0 | 0 | 0 | 0 | 0 | 0 | — |
| 136 | | 5.6050 | 3 | — | — | 0 | 3 | 3 | 3 | — | 3 | 3 | 3 | 3 | 3 | 3 | 3 | 3 | 3 | 3 | 3 | 3 | — | — |
| | | 1.1210 | 2 | — | — | 0 | N | 3 | 3 | — | 3 | 3 | 3 | 3 | 3 | 3 | 3 | 3 | 3 | 3 | 3 | 3 | — | — |
| | | 0.5605 | 1 | — | — | 0 | 3 | 0 | 2 | — | 1 | 1 | 3 | 3 | 1 | 3 | 3 | 1 | 3 | 3 | 2 | 3 | — | — |
| | | 0.2803 | 0 | — | — | 0 | 2 | 1 | 1 | — | 1 | 1 | 3 | 1 | 0 | 3 | 3 | 0 | 3 | 3 | 2 | 0 | — | — |
| | | 0.1401 | 0 | — | — | 1 | 3 | 0 | 1 | — | 0 | 0 | 3 | 0 | 0 | 2 | 3 | 2 | 3 | 1 | 0 | N | — | — |
| | | 0.0701 | 0 | — | — | 0 | 3 | 0 | 0 | — | 0 | 0 | 1 | 1 | 0 | 0 | 0 | 0 | 1 | 3 | 0 | 0 | — | — |
| | | 0.0350 | 0 | — | — | 0 | 2 | 0 | 0 | — | 0 | 0 | 1 | 0 | 0 | 0 | 0 | 0 | 1 | 0 | 1 | 1 | — | — |
| | | 0.0175 | 0 | — | — | 0 | 0 | 0 | 0 | — | 0 | 0 | 0 | 0 | 0 | 0 | 0 | 0 | 0 | 0 | 0 | 1 | — | — |
| | | 0.0087 | 0 | — | — | 0 | N | 0 | 1 | — | 0 | 0 | 0 | 0 | 0 | 0 | 0 | 0 | 0 | 0 | 0 | 1 | — | — |
| 137 | | 11.2100 | 0 | 0 | 2 | 0 | 0 | 0 | 0 | 1 | 1 | 3 | 3 | 3 | 3 | 3 | 3 | 3 | 3 | 3 | — | — | — | — |
| | | 5.6050 | 1 | N | 0 | 0 | 1 | 0 | 0 | 0 | 0 | 2 | 3 | 3 | 2 | 3 | 3 | 3 | 3 | 3 | — | — | — | — |
| | | 1.1210 | 0 | 0 | 0 | 0 | 0 | 0 | 1 | 0 | 0 | 0 | 0 | 1 | 0 | 0 | 1 | 3 | 0 | 2 | — | — | — | — |
| 138 | | 5.6050 | 3 | 2 | 2 | N | 3 | 3 | 3 | 3 | 3 | 3 | 3 | 3 | 3 | 3 | 3 | 3 | 3 | 3 | — | — | — | — |
| | | 1.1210 | 0 | 3 | 0 | N | 1 | 1 | 3 | 2 | 2 | 0 | 1 | 0 | 0 | 1 | 2 | 0 | 3 | 0 | — | — | — | — |
| | | 0.2803 | 1 | 1 | 0 | N | 0 | 0 | 2 | 1 | 1 | 0 | 1 | 0 | 1 | 0 | 1 | 0 | 3 | 0 | — | — | — | — |
| | | 0.0701 | 0 | 1 | 0 | N | 0 | 0 | 2 | 1 | N | 0 | 1 | 0 | 0 | 0 | 1 | 0 | 2 | 0 | — | — | — | — |
| 139 | I | 5.6050 | 0 | 2 | 0 | 0 | 1 | 0 | 0 | — | 0 | 0 | 2 | 0 | 0 | 2 | 2 | 2 | 3 | 0 | — | — | — | 3 |
| | I | 1.1210 | 0 | 1 | 0 | 0 | 2 | 0 | 1 | — | 1 | 0 | 1 | 0 | 0 | 1 | 1 | 0 | 1 | 0 | — | — | — | 0 |
| | I | 0.2803 | 0 | 1 | 0 | 0 | 1 | 0 | 0 | — | 0 | 0 | 1 | 0 | 0 | 1 | 0 | 0 | 0 | 0 | — | — | — | 0 |
| | I | 0.0701 | 0 | 0 | 0 | 0 | 0 | 0 | 0 | — | 0 | 0 | 0 | 0 | 0 | 0 | 0 | 0 | 0 | 0 | — | — | — | 0 |
| 140 | | 5.6050 | 3 | — | — | 0 | 3 | 3 | 3 | — | 3 | 3 | 3 | 3 | 3 | 3 | 3 | 3 | 3 | 3 | 3 | 3 | 3 | — |
| | | 1.1210 | 1 | — | — | 0 | 3 | 2 | 3 | — | 3 | 3 | 3 | 3 | 3 | 3 | 3 | 3 | 3 | 3 | 3 | 3 | 3 | — |
| | | 0.5605 | 0 | — | — | 0 | 3 | 2 | 3 | — | 2 | 1 | 2 | 2 | 1 | 2 | 3 | 3 | 3 | 3 | 3, | 3 | 3 | — |
| | | 0.2803 | 0 | — | — | 0 | 3 | 1 | 0 | — | 1 | 3 | 1 | 2 | 0 | 2 | 3 | 3 | 3 | 3 | 2 | 3 | 3 | — |
| | | 0.1401 | 0 | — | — | 0 | 3 | 0 | 0 | — | 0 | 0 | 0 | 0 | 0 | 0 | 2 | 3 | 3 | 3 | 1 | 3 | 1 | — |
| | | 0.0701 | 0 | — | — | 0 | 0 | 0 | 0 | — | 0 | 0 | 0 | 0 | 0 | 0 | 0 | 1 | 1 | 3 | 0 | 2 | 1 | — |
| | | 0.0350 | 0 | — | — | 0 | 1 | 0 | 0 | — | 0 | 0 | 0 | 0 | 0 | 0 | 0 | 0 | N | 3 | N | 2 | 0 | — |
| | | 0.0175 | 0 | — | — | 0 | 0 | 0 | 0 | — | 0 | 0 | 0 | 0 | 0 | 0 | 0 | 0 | 0 | 0 | N | 1 | N | — |
| | | 0.0087 | 0 | — | — | 0 | N | 0 | 0 | — | 0 | 0 | 0 | 0 | 0 | 0 | 0 | 0 | 3 | 0 | 0 | 2 | 1 | — |
| | | 0.0044 | 0 | — | — | 0 | N | 0 | 0 | — | 0 | 0 | 0 | 0 | 0 | 0 | 0 | 0 | 0 | 0 | 0 | N | 1 | — |
| 141 | | 5.6050 | 3 | — | — | 0 | 3 | 3 | 3 | — | 3 | 3 | 1 | 3 | 3 | 3 | 3 | 3 | 3 | 3 | 3 | 3 | 3 | — |
| | | 1.1210 | 2 | — | — | 0 | 3 | 0 | 2 | — | 2 | 1 | 2 | 2 | 1 | 3 | 3 | 3 | 3 | 3 | 3 | 3 | 3 | — |
| | | 0.5605 | 3 | — | — | 0 | 3 | 0 | 2 | — | 0 | 1 | 1 | 2 | 0 | 3 | 3 | 3 | 3 | 3 | 2 | 3 | 3 | — |
| | | 0.2803 | 0 | — | — | 0 | 1 | 0 | 1 | — | 0 | 0 | 0 | 0 | 0 | 3 | 3 | 3 | 3 | 3 | 1 | 3 | 1 | — |
| | | 0.1401 | 0 | — | — | 0 | 0 | 0 | 0 | — | 0 | 0 | 0 | 0 | 0 | 0 | 0 | 0 | 3 | 3 | 1 | 2 | 1 | — |
| | | 0.0701 | 0 | — | — | 0 | 0 | 0 | 0 | — | 0 | 0 | 0 | 0 | 0 | 1 | 0 | 1 | 0 | 2 | 0 | 1 | 2 | — |
| | | 0.0350 | 0 | — | — | 0 | 0 | 0 | 0 | — | 0 | 0 | 0 | 0 | 0 | 0 | 0 | 0 | N | 3 | 1 | 0 | 0 | — |
| | | 0.0175 | 0 | — | — | 0 | 1 | 0 | 0 | — | 0 | 0 | 0 | 0 | 0 | 0 | 0 | 0 | 0 | 0 | 0 | N | N | — |
| | | 0.0087 | 0 | — | — | 0 | N | 0 | 0 | — | 0 | 0 | 0 | 0 | 0 | 0 | 0 | 0 | 0 | 0 | N | N | N | — |
| 142 | D | 5.6050 | 1 | 1 | 1 | 0 | 3 | 0 | 0 | 2 | 0 | 3 | 3 | 3 | 1 | 3 | 3 | 3 | 3 | 3 | — | — | — | — |

-continued

TABLE 3-continued

| | | | | | | | | | | | | | | | | | | | | | | | | |
|---|---|---|---|---|---|---|---|---|---|---|---|---|---|---|---|---|---|---|---|---|---|---|---|---|
| | D | 1.1210 | 0 | 0 | 0 | 0 | 3 | 0 | 0 | 0 | 0 | 2 | 3 | 2 | 1 | 2 | 3 | 3 | 3 | 3 | — | — | — | — |
| | D | 0.2803 | 0 | 0 | 0 | 0 | 0 | 0 | 0 | 0 | 0 | 0 | 0 | 0 | 0 | 0 | 0 | 0 | 2 | 0 | — | — | — | — |
| | D | 0.0701 | 0 | 0 | 0 | 0 | 0 | 0 | 0 | 0 | 0 | 0 | 0 | 0 | 0 | 0 | 0 | 0 | 0 | 0 | — | — | — | — |
| | D | 0.0175 | 0 | 0 | 0 | 0 | 0 | 0 | N | 0 | 0 | 0 | 0 | 0 | 0 | 0 | 0 | 0 | 0 | 0 | — | — | — | — |
| 143 | D | 5.6050 | 3 | 1 | 3 | 0 | 3 | 3 | 3 | 2 | 2 | 3 | 3 | 3 | 3 | 3 | 3 | 3 | 3 | 3 | — | — | — | — |
| | D | 1.1210 | 0 | 0 | 0 | 0 | 3 | 0 | 0 | 1 | 0 | 3 | 3 | 3 | 2 | 3 | 3 | 3 | 3 | 3 | — | — | — | — |
| | D | 0.2803 | N | 0 | 0 | 0 | 0 | 0 | 0 | 0 | 0 | 0 | 0 | 0 | 0 | 0 | 0 | 0 | 2 | 0 | — | — | — | — |
| | D | 0.0701 | 1 | 0 | 0 | 0 | 0 | 0 | 1 | 0 | 0 | 0 | 0 | 0 | 0 | 0 | 0 | 0 | 0 | 0 | — | — | — | — |
| | D | 0.0175 | 0 | 0 | 0 | 0 | 0 | 0 | 0 | 0 | 0 | 0 | 0 | 0 | 0 | 0 | N | 0 | 0 | 0 | — | — | — | — |
| 144 | D | 5.6050 | 3 | 0 | 3 | 1 | 3 | 3 | 3 | 3 | 3 | 3 | 3 | 3 | 3 | 3 | 3 | 3 | 3 | 3 | — | — | — | — |
| | D | 1.1210 | 1 | 0 | 0 | 0 | 3 | 2 | 1 | 2 | 0 | 3 | 3 | 2 | 1 | 3 | 3 | 3 | 3 | 3 | — | — | — | — |
| | D | 0.2803 | 0 | 0 | 0 | 0 | 0 | 0 | 0 | 0 | 0 | 0 | 2 | 0 | 0 | 2 | 3 | 2 | 3 | 1 | — | — | — | — |
| | D | 0.0701 | 0 | 0 | 0 | 0 | 0 | 0 | 0 | 0 | 0 | 1 | 0 | 0 | 0 | 0 | 0 | 0 | 0 | 0 | — | — | — | — |
| | D | 0.0175 | 0 | 0 | 0 | 0 | 0 | 0 | 0 | 0 | N | 0 | 0 | 0 | 0 | 0 | 0 | 0 | N | 0 | — | — | — | — |
| 145 | D | 5.6050 | 3 | 1 | 3 | 2 | 3 | 3 | 3 | 3 | 3 | 3 | 3 | 3 | 3 | 3 | 3 | 3 | 3 | 3 | — | — | — | — |
| | D | 1.1210 | 1 | 0 | 2 | 0 | 2 | 1 | 0 | 1 | 0 | 3 | 3 | 3 | 3 | 3 | 3 | 3 | 3 | 3 | — | — | — | — |
| | D | 0.2803 | 0 | 0 | 0 | 0 | 0 | 0 | 0 | 0 | 0 | 0 | 1 | 0 | 0 | 3 | 1 | 0 | 3 | 0 | — | — | — | — |
| | D | 0.0701 | 0 | 0 | 0 | 0 | 0 | 0 | 0 | 0 | 0 | 0 | 0 | 0 | 0 | 0 | 0 | 0 | 0 | 0 | — | — | — | — |
| | D | 0.0175 | 0 | 0 | 0 | 0 | 0 | 0 | 0 | 0 | 0 | 0 | 0 | 0 | 0 | 0 | 0 | 0 | 0 | 0 | — | — | — | — |
| | D | 0.0087 | 0 | 0 | 0 | 0 | 0 | 0 | 0 | 0 | 0 | 0 | 0 | 0 | 0 | 0 | 0 | 0 | 0 | 0 | — | — | — | — |
| 146 | | 5.6050 | 3 | 0 | 3 | 0 | 3 | 3 | 3 | 3 | 3 | 3 | 3 | 3 | 3 | 3 | 3 | 3 | 3 | 3 | — | — | — | — |
| | | 1.1210 | 0 | 0 | 1 | 0 | 2 | 1 | 0 | 1 | 0 | 3 | 3 | 3 | 0 | 3 | 3 | 3 | 3 | 3 | — | — | — | — |
| | | 0.2803 | 1 | 0 | 0 | 0 | 0 | 0 | 0 | 0 | 0 | 0 | 1 | 0 | 0 | 0 | 3 | 0 | 0 | 0 | — | — | — | — |
| | | 0.0701 | 0 | 0 | 0 | 0 | 0 | 0 | 0 | 0 | 0 | 0 | 0 | 0 | 0 | 0 | 0 | 0 | 0 | 0 | — | — | — | — |
| | | 0.0175 | 0 | 0 | 0 | 0 | 0 | 0 | 0 | 0 | 0 | 0 | 0 | 0 | 0 | 0 | 0 | 0 | 0 | 0 | — | — | — | — |
| | | 0.0087 | 0 | 0 | 0 | 0 | 0 | 0 | 0 | 0 | 0 | 0 | 0 | 0 | 0 | 0 | 0 | 0 | 0 | 0 | — | — | — | — |
| 147 | | 5.6050 | 3 | 3 | 3 | 1 | 3 | 3 | 3 | 3 | 3 | 3 | 3 | 3 | 3 | 3 | 3 | 3 | 3 | 3 | — | — | — | — |
| | | 1.1210 | 3 | 2 | 3 | 2 | 3 | 3 | 3 | 3 | 3 | 3 | 3 | 3 | 0 | 3 | 3 | 3 | 3 | 3 | — | — | — | — |
| | | 0.2803 | 1 | 1 | 2 | 1 | 3 | 2 | 2 | 3 | 1 | 3 | 3 | 3 | 1 | 3 | 3 | 3 | 3 | 3 | — | — | — | — |
| | | 0.0701 | N | 0 | 0 | 0 | 3 | 1 | 1 | 3 | 1 | 1 | 2 | 1 | 0 | 1 | 2 | 3 | 3 | 3 | — | — | — | — |
| | | 0.0175 | 0 | 0 | 1 | 0 | 0 | 0 | 0 | 0 | 0 | 0 | 1 | 0 | 0 | 0 | 1 | 0 | 2 | 1 | — | — | — | — |
| | | 0.0087 | 0 | 0 | 0 | 0 | 0 | 0 | 0 | 0 | 0 | 0 | 0 | 0 | 0 | 0 | 1 | 0 | 1 | 0 | — | — | — | — |
| 148 | | 5.6050 | 3 | — | — | 0 | 3 | 3 | 2 | — | 3 | 3 | 2 | 3 | — | 3 | 3 | 3 | 3 | — | 3 | 3 | 3 | — |
| | | 1.1210 | 1 | — | — | 0 | 3 | 2 | 2 | — | 3 | 2 | 1 | 0 | — | 2 | 3 | 3 | 3 | — | 3 | 3 | 3 | — |
| | | 0.2803 | 0 | — | — | 0 | 1 | 1 | 1 | — | 1 | 1 | 0 | 1 | — | 0 | 1 | 2 | 3 | — | 1 | 2 | 2 | — |
| | | 0.0561 | 0 | — | — | 0 | 0 | 0 | 0 | — | 0 | 0 | 0 | 0 | — | 0 | 1 | 1 | 3 | — | 0 | 1 | 0 | — |

+ POOR PESW EMERGENCE
( TITRATION OUT OF SEQUENCE - RETEST ON 4/15/86
) PANS DRY ON 4/13/87
– RICE PORR THROUGHOUT TEST
  OVERWATERED AT INITIAL IRRIGATION
/ SEEDED PANS SPRAYED AND THEN COVERED WITH SAND
< COBU POOR THROUGHOUT TEST
! NO DATA FOR LACG AND COBU DUE TO POOR EMERGENCE
$ COBU POOR THROUGHOUT TEST
~ COBU EMERGENCE AND RICE GROWTH VARIABLE
  NO DATA FOR COBU DUE TO POOR EMERGENCE
{ NO DATA FOR COBU DUE TO POOR GERMINATION/EMERGENCE
. Greenhouse temp. flucuations Oct. 10, 11, 17, 18
B POOR SOBE PLANTS THROUGHOUT TEST
D PRMI POOR THROUGHOUT TEST
F Plant growth variable due to erratic watering.
I Damping off throughout test.
J POOR RICE, WIBW, PESW, AND COLQ STANDS
L VELE AND HESE LEAF MALFORMATION
M POOR GERMINATION OR EMERGENCE OF MOGL AND COBU
N MORNINGGLORY EMERGENCE ERRATIC

POST-EMERGENT HERBICIDE ACTIVITY ON PLANTS

Although, as has been stated above, the compounds of this invention exhibit predominantly pre-emergence activity in greenhouse testing, nevertheless many of these compounds are active post-emergent herbicides. The post-emergent activity is best seen on younger plants treated at the 1½ to 2 leaf stage. In the tests which follow, larger and more developed plants were used The post-emerqence herbicidal activity of compounds of this invention was demonstrated by greenhouse testing, and the results are shown in the following Table C. The post-emergent herbicidal activity index used in Table C is as follows:

| Plant Response | Index |
|---|---|
| 0-24% inhibition | 0 |
| 25-49% inhibition | 1 |
| 50-74% inhibition | 2 |
| 75-99% inhibition | 3 |
| 100% inhibition | 4 |
| Species not planted | — or a blank |
| Species planted. no data | N |

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/ha. The pans were returned to the greenhouse and watered as before and the injury to the plants as compared to those in control pans was observed at approximately 10-14 days (usually 11 days). The plant identifying codes in Table C are the same as defined, for Table A above.

TABLE C

| Ex. No. | | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|---|
| | | | | | | Herbicide Primary Post, spectrums 25 and 90 (C = 100% control) | | | | | | | | | | | |
| 1 | | 11.2100 | 0 | — | — | 0 | 0 | 0 | 0 | 0 | — | — | — | 0 | 0 | 0 | 0 |
| 2 | | 11.2100 | 0 | — | — | 0 | 0 | 0 | 0 | 0 | — | — | 0 | 0 | 0 | 0 | 0 |
| 3 | | 11.2100 | 0 | — | — | 0 | 0 | 0 | 0 | 0 | — | — | N | 0 | 0 | 0 | 0 |
| 4 | | 11.2100 | 0 | — | — | 0 | 0 | 0 | 0 | 0 | — | — | 1 | 0 | 0 | 0 | 0 |
| 5 | | 11.2100 | 0 | — | — | 0 | 0 | 0 | 0 | 0 | — | — | — | 0 | 0 | 0 | 0 |
| 6 | | 11.2100 | 0 | — | — | 0 | 0 | 0 | 0 | 0 | — | — | — | 0 | 0 | 0 | N |
| 7 | | 11.2100 | 0 | — | — | 0 | 0 | 1 | 0 | 0 | — | — | N | 0 | 0 | 0 | 0 |
| 8 | @ | 11.2100 | N | — | — | 0 | 0 | 0 | 0 | 1 | — | — | 0 | 0 | 0 | 0 | 0 |
| 9 | | 11.2100 | 0 | — | — | 0 | 2 | 1 | 1 | 1 | — | — | — | 1 | 1 | 0 | 0 |
| 10 | | 11.2100 | 0 | — | — | 0 | 0 | 1 | 1 | 1 | — | — | 0 | 0 | 0 | 0 | 0 |
| 11 | | 11.2100 | 0 | — | — | 0 | 1 | 1 | 1 | 0 | — | — | 0 | 0 | 0 | 0 | 0 |
| 12 | * | 11.2100 | 0 | — | — | 0 | 0 | 0 | 0 | 0 | — | — | 0 | 0 | 0 | 0 | 0 |
| 13 | | 11.2100 | 0 | — | — | 0 | 0 | 0 | 0 | 0 | — | — | 0 | 0 | N | 0 | 0 |
| 14 | | 11.2100 | 0 | — | — | 0 | 0 | 0 | 0 | 0 | — | — | 0 | 0 | N | 0 | 0 |
| 15 | @ | 11.2100 | 0 | — | — | 0 | 0 | 0 | 0 | 1 | — | — | 0 | 0 | 0 | 0 | 0 |
| 16 | | 11.2100 | 0 | 1 | 0 | 0 | 0 | 0 | 0 | 1 | 2 | 2 | — | — | — | — | — |
| | | 11.2100 | 0 | 0 | 0 | 0 | 0 | 0 | 2 | 0 | 1 | 1 | — | — | — | — | — |
| 17 | | 11.2100 | 0 | 0 | 3 | 1 | 2 | 2 | 0 | 1 | 1 | 2 | — | — | — | — | — |
| 18 | | 11.2100 | 0 | 0 | 0 | 0 | 0 | 0 | 0 | 0 | 1 | 0 | — | — | — | — | — |
| 19 | | 11.2100 | 0 | — | — | 0 | 1 | 2 | 1 | 1 | — | — | — | 1 | 1 | 0 | N |
| 20 | | 11.2100 | 0 | — | — | 0 | 0 | 0 | 0 | 0 | — | — | 0 | 0 | 0 | 0 | 0 |
| 21 | , | 11.2100 | 0 | 0 | 2 | 0 | 0 | 2 | 1 | 2 | 2 | 2 | — | — | — | — | — |
| 22 | ] | 11.2100 | 0 | 0 | 2 | 0 | 0 | 1 | 0 | 2 | 2 | 2 | — | — | — | — | — |
| 23 | ; | 11.2100 | 0 | 0 | 2 | 0 | 0 | 2 | 0 | 2 | 2 | 2 | — | — | — | — | — |
| 24 | | 11.2100 | 0 | — | — | 0 | 1 | 1 | 1 | 1 | — | — | — | 1 | 1 | 0 | 0 |
| 25 | | 11.2100 | 0 | — | — | 0 | 1 | 0 | 0 | 0 | — | — | 0 | — | 0 | 0 | 0 |
| 26 | | 11.2100 | 0 | — | — | 0 | 2 | 1 | 0 | 0 | — | — | 0 | 2 | 0 | 0 | 0 |
| 27 | | 11.2100 | 0 | — | — | 0 | 0 | 0 | 0 | 0 | — | — | N | 0 | 0 | 0 | 0 |
| | | 11.2100 | 0 | — | — | 0 | 0 | 0 | 0 | 0 | — | — | N | 0 | 0 | 0 | 0 |
| 28 | | 11.2100 | 0 | — | — | 0 | 0 | 0 | 0 | 0 | — | — | 0 | 0 | 0 | 0 | 0 |
| 29 | | 11.2100 | 0 | — | — | 0 | 0 | 0 | 0 | 0 | — | — | 0 | 1 | 0 | 0 | 0 |
| 30 | | 11.2100 | 0 | — | — | 0 | 0 | 0 | 0 | 0 | — | — | 0 | 0 | 0 | 0 | 0 |
| 31 | | 11.2100 | 0 | — | — | 0 | 0 | 0 | 0 | 0 | — | — | 0 | 0 | 0 | 0 | 0 |
| 32 | | 11.2100 | 0 | — | — | 0 | 0 | 0 | 0 | 0 | — | — | 0 | 0 | 0 | 0 | 0 |
| 33 | | 11.2100 | 0 | — | — | 0 | 0 | 0 | 0 | 0 | — | — | 0 | 0 | 0 | 0 | 0 |
| 34 | | 11.2100 | 0 | — | — | 0 | 0 | 0 | 0 | 0 | — | — | 0 | 0 | 0 | 0 | 0 |
| 35 | | 11.2100 | 0 | — | — | 0 | 0 | 0 | 0 | 0 | — | — | 0 | 3 | 0 | 0 | 0 |
| 36 | | 11.2100 | 0 | — | — | 0 | 0 | 0 | 0 | 0 | — | — | 0 | 0 | 0 | 0 | 0 |
| 37 | | 11.2100 | 0 | — | — | 0 | 0 | 0 | 0 | 0 | — | — | 0 | 1 | 0 | 0 | 0 |
| 38 | | 11.2100 | 0 | — | — | 0 | 1 | 0 | 0 | 0 | — | — | 0 | 0 | 0 | 0 | 0 |
| 39 | | 11.2100 | 0 | — | — | 0 | 1 | 0 | 0 | 0 | — | — | 0 | 0 | 0 | 0 | 0 |
| 40 | | 11.2100 | 0 | — | — | 0 | 0 | 0 | 0 | 0 | — | — | 0 | 0 | 0 | 0 | 0 |
| 41 | | 11.2100 | 0 | — | — | 0 | 1 | 0 | 0 | 0 | — | — | 0 | 0 | 0 | 0 | 0 |
| 42 | | 11.2100 | 0 | — | — | 0 | 0 | 0 | 0 | 0 | — | — | 0 | — | 0 | 0 | 0 |
| 43 | | 11.2100 | 0 | — | — | 0 | 0 | 1 | 0 | 0 | — | — | 0 | 0 | 0 | 0 | 0 |
| 44 | | 11.2100 | 0 | — | — | 0 | 0 | 0 | 0 | 0 | — | — | 0 | 0 | 0 | 0 | 0 |

TABLE C-continued

| Ex. No. | | Rate kg/ha | Herbicide Primary Post, spectrums 25 and 90 (C = 100% control) Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|---|
| 45 | | 11.2100 | 0 | — | — | 0 | 1 | 1 | 1 | 0 | — | — | — | 1 | 0 | 0 | 0 |
| 46 | | 11.2100 | 0 | — | — | N | 0 | 0 | 0 | 0 | — | — | 0 | 1 | 0 | 0 | 0 |
| 47 | | 11.2100 | 0 | — | — | 0 | 0 | 0 | 0 | 0 | — | — | 0 | 0 | 0 | 0 | 0 |
| 48 | | 11.2100 | 0 | — | — | 0 | 0 | 0 | 0 | 0 | — | — | 0 | 3 | 0 | 0 | 0 |
| 49 | | 11.2100 | 0 | — | — | 0 | 0 | 0 | 0 | 0 | — | — | 0 | 0 | 0 | 0 | 0 |
| 50 | | 11.2100 | 0 | — | — | 0 | 0 | 0 | 0 | 0 | — | — | 0 | 0 | 0 | 0 | 0 |
| 51 | | 11.2100 | 0 | — | — | 0 | 0 | 0 | 1 | 1 | — | — | 0 | 1 | 0 | 0 | 0 |
| 52 | | 11.2100 | 0 | — | — | 0 | 1 | 1 | 0 | 1 | — | — | 0 | 2 | 0 | 0 | 0 |
| 53 | | 11.2100 | 0 | — | — | 0 | 0 | 0 | 0 | 0 | — | — | 0 | 0 | 0 | 0 | 0 |
| 54 | | 11.2100 | 0 | — | — | 0 | 0 | 1 | 0 | 1 | — | — | 0 | 0 | 0 | 0 | 0 |
| 55 | | 11.2100 | 0 | 0 | 0 | 0 | 0 | 0 | 0 | 0 | 0 | 0 | — | — | — | — | — |
| | | 11.2100 | 0 | 2 | 0 | 0 | 0 | 0 | 0 | 0 | 2 | 1 | — | — | — | — | — |
| 56 | | 11.2100 | 0 | 0 | 0 | 0 | 0 | 0 | 0 | 0 | 0 | 0 | — | — | — | — | — |
| 57 | | 11.2100 | 0 | 0 | 0 | 0 | 0 | 0 | 0 | 0 | 0 | 0 | — | — | — | — | — |
| 58 | | 11.2100 | 0 | 0 | 3 | 0 | 2 | 2 | 0 | 2 | 2 | 2 | — | — | — | — | — |
| 59 | | 11.2100 | 0 | — | — | 0 | 2 | 0 | 0 | 0 | — | — | 0 | 0 | 0 | 0 | 0 |
| 60 | | 11.2100 | 0 | — | — | 0 | 1 | 0 | 0 | 0 | — | — | 0 | 0 | 0 | 0 | 0 |
| 61 | | 11.2100 | 0 | — | — | 0 | 0 | 0 | 0 | 0 | — | — | 0 | 0 | N | 0 | 0 |
| 62 | | 11.2100 | 0 | 0 | 0 | 0 | 1 | 0 | 0 | 0 | 0 | 0 | — | — | — | — | — |
| 63 | | 11.2100 | 0 | 0 | 2 | 0 | 2 | 0 | 0 | 0 | 0 | 0 | — | — | — | — | — |
| 64 | ; | 11.2100 | 0 | 0 | 2 | 0 | 2 | 1 | 0 | 2 | 2 | 2 | — | — | — | — | — |
| 65 | | 11.2100 | 0 | 0 | 2 | 0 | 0 | 0 | 0 | 1 | 0 | 2 | — | — | — | — | — |
| 66 | ; | 11.2100 | 0 | 0 | 2 | 0 | 2 | 2 | 0 | 2 | 2 | 2 | — | — | — | — | — |
| 67 | , | 11.2100 | 0 | 0 | 2 | 0 | 1 | 0 | 0 | 2 | N | N | — | — | — | — | — |
| 68 | , | 11.2100 | 0 | 0 | 2 | 0 | 1 | 1 | 0 | 2 | 2 | 2 | — | — | — | — | — |
| 69 | , | 11.2100 | 0 | 0 | 2 | 0 | 1 | 1 | 1 | 2 | 2 | 2 | — | — | — | — | — |
| 70 | , | 11.2100 | 0 | 0 | 2 | 0 | 2 | 1 | 1 | 2 | 2 | 2 | — | — | — | — | — |
| 71 | , | 11.2100 | 0 | 0 | 2 | 0 | 2 | 1 | 2 | 2 | 2 | 2 | — | — | — | — | — |
| 72 | | 11.2100 | 0 | 0 | 2 | 0 | 1 | 1 | 1 | 2 | 1 | 1 | — | — | — | — | — |
| 73 | | 11.2100 | 0 | 0 | 2 | 0 | 0 | 1 | 0 | 1 | 1 | 1 | — | — | — | — | — |
| 74 | | 11.2100 | 1 | 1 | 3 | 0 | 2 | 1 | 1 | 1 | 1 | 1 | — | — | — | — | — |
| 75 | | 11.2100 | 0 | 0 | 3 | 0 | 2 | 1 | 2 | 1 | 2 | 1 | — | — | — | — | — |
| 76 | | 11.2100 | 0 | 0 | 2 | 0 | 2 | 2 | 0 | 2 | 2 | 2 | — | — | — | — | — |
| 77 | | 11.2100 | 0 | 0 | 0 | 0 | 2 | 2 | 0 | 0 | 1 | 2 | — | — | — | — | — |
| 78 | | 11.2100 | 0 | 1 | 0 | 0 | 1 | 2 | 1 | 0 | 0 | 1 | — | — | — | — | — |
| 79 | | 11.2100 | 0 | — | — | 3 | 0 | 0 | 0 | 0 | — | — | N | 1 | 1 | 0 | 0 |
| 80 | | 11.2100 | 0 | 0 | 0 | 0 | 0 | 0 | 0 | 0 | 1 | 0 | — | — | — | — | — |
| 81 | | 11.2100 | 0 | 0 | 0 | 0 | 0 | 0 | 0 | 0 | 0 | 0 | — | — | — | — | — |
| 82 | | 11.2100 | 0 | 0 | 0 | 0 | 0 | 0 | 0 | 0 | 0 | 0 | — | — | — | — | — |
| 83 | | 11.2100 | 0 | — | — | 0 | 1 | 1 | 1 | 1 | — | — | 1 | 1 | 0 | 0 | 0 |
| 84 | | 11.2100 | 0 | — | — | 0 | 0 | 1 | 1 | 1 | — | — | — | 1 | 0 | 0 | 0 |
| 85 | | 11.2100 | 0 | — | — | 0 | 2 | 1 | 1 | 1 | — | — | — | 2 | 1 | 0 | N |
| 86 | | 11.2100 | 0 | 0 | 1 | 0 | 1 | 0 | 0 | 0 | 1 | 0 | — | — | — | — | — |
| 87 | | 11.2100 | 0 | 0 | 0 | 0 | 0 | 0 | 0 | 0 | 0 | 0 | — | — | — | — | — |
| 88 | | 11.2100 | 0 | 0 | 0 | 0 | 0 | 0 | 0 | 0 | 1 | 0 | — | — | — | — | — |
| 89 | | 11.2100 | 3 | — | — | 1 | 3 | 2 | 3 | 3 | — | — | 0 | N | 3 | 2 | 2 |
| | | 11.2100 | 0 | — | — | 0 | 0 | 0 | 1 | 0 | — | — | 0 | 0 | 0 | 0 | 0 |
| | | 11.2100 | 3 | — | — | 2 | 3 | 3 | 3 | 3 | — | — | 1 | N | 3 | 2 | 2 |
| 90 | | 11.2100 | 0 | — | — | 0 | 0 | 0 | 0 | 0 | — | — | 0 | 0 | 0 | 0 | 0 |
| 91 | | 11.2100 | 0 | — | — | 0 | 0 | 0 | 0 | 0 | — | — | 0 | 0 | 0 | 0 | 0 |
| 92 | | 11.2100 | 0 | 0 | 0 | 0 | 0 | 2 | 1 | 2 | 2 | 2 | — | — | — | — | — |
| 93 | | 11.2100 | 0 | 0 | 0 | 0 | 1 | 1 | 1 | 2 | 2 | 2 | — | — | — | — | — |
| 94 | | 11.2100 | 0 | — | — | 0 | 0 | 0 | 0 | 0 | — | — | — | 0 | 0 | 0 | 0 |
| 95 | | 11.2100 | 0 | — | — | 0 | 0 | 0 | 0 | 0 | — | — | 0 | 0 | 0 | 0 | 0 |
| 96 | @ | 11.2100 | 0 | — | — | 0 | 1 | 0 | 0 | 1 | — | — | 0 | 0 | N | 1 | 0 |
| 97 | | 11.2100 | 0 | 0 | 0 | 0 | 0 | 1 | 0 | 0 | 1 | 1 | — | — | — | — | — |
| 98 | | 11.2100 | 0 | 0 | 2 | 0 | 0 | 2 | 0 | 1 | 2 | 1 | — | — | — | — | — |
| 99 | | 11.2100 | 0 | — | — | 0 | 2 | 1 | 0 | 0 | — | — | 0 | 0 | 0 | 0 | 0 |
| 100 | | 11.2100 | 0 | — | — | 0 | 1 | 0 | 0 | 0 | — | — | 0 | 0 | 0 | 0 | 0 |
| 101 | | 11.2100 | 0 | — | — | 0 | 1 | 0 | 0 | 0 | — | — | — | 1 | 0 | 0 | N |
| 102 | | 11.2100 | 0 | — | — | 0 | 2 | 1 | 0 | 0 | — | — | 0 | 1 | — | 0 | 0 |
| 103 | | 11.2100 | 0 | — | — | 0 | 1 | 1 | 0 | 0 | — | — | N | 0 | 0 | 0 | 0 |
| 104 | | 11.2100 | 0 | — | — | 0 | 0 | 1 | 0 | 1 | — | — | 0 | 1 | 0 | 0 | N |
| 105 | | 11.2100 | 0 | — | — | 0 | 0 | 0 | 0 | 0 | — | — | 0 | 0 | 0 | 0 | N |
| 106 | | 11.2100 | 0 | — | — | 0 | 0 | 0 | 0 | 0 | — | — | 0 | 0 | 0 | 0 | 0 |
| 107 | | 11.2100 | 0 | — | — | 0 | 0 | 0 | 0 | 0 | — | — | 0 | 0 | 0 | 0 | 0 |
| 108 | | 11.2100 | 0 | — | — | 0 | 1 | 0 | 0 | 0 | — | — | 0 | 0 | 0 | 0 | 0 |
| 109 | | 11.2100 | 0 | — | — | 0 | 0 | 0 | 0 | 0 | — | — | 0 | 0 | 0 | 0 | 0 |
| 110 | | 11.2100 | 0 | — | — | 0 | 0 | 0 | 0 | 0 | — | — | 0 | 0 | 0 | 0 | 0 |
| 111 | | 11.2100 | 0 | — | — | 0 | 1 | 0 | 0 | 0 | — | — | 0 | 0 | 0 | 0 | 0 |
| 112 | | 11.2100 | 0 | — | — | 0 | 1 | 0 | 0 | 0 | — | — | 0 | 0 | 0 | 0 | 0 |
| 113 | K | 11.2100 | 0 | — | — | 0 | 1 | 0 | 1 | 0 | — | — | 1 | 1 | 0 | 0 | 0 |
| 114 | | 11.2100 | 0 | — | — | 0 | 0 | 0 | 0 | 0 | — | — | — | 0 | 0 | 0 | N |
| 115 | | 11.2100 | 0 | — | — | 0 | 2 | 0 | 0 | 0 | — | — | 0 | — | 0 | 0 | N |
| 116 | | 11.2100 | 0 | — | — | 0 | 1 | 1 | 0 | 0 | — | — | — | 2 | 0 | 0 | N |
| 117 | | 11.2100 | 0 | — | — | 0 | 1 | 1 | 0 | 0 | — | — | 0 | 1 | — | 0 | 0 |
| 118 | | 11.2100 | 0 | — | — | 0 | 0 | 0 | 1 | 0 | — | — | 0 | 1 | — | 0 | 0 |
| 119 | | 11.2100 | 0 | — | — | 0 | 0 | 1 | 0 | 2 | — | — | 0 | 3 | N | 0 | 0 |

TABLE C-continued

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| | Herbicide Primary Post, spectrums 25 and 90 (C = 100% control) | | | | | | | | | | | | | | | |
| 120 | 11.2100 | 0 | — | — | 0 | 0 | 0 | 0 | 0 | — | — | 0 | 1 | 0 | 0 | 0 |
| 121 | 11.2100 | 0 | 0 | 0 | 0 | 0 | 0 | 0 | 0 | 0 | 0 | — | — | — | — | — |
| 122 | 11.2100 | 0 | — | — | 0 | 0 | 0 | 0 | 0 | — | — | 0 | 0 | 0 | 0 | N |
| 123 | 11.2100 | 0 | — | — | 0 | 0 | 0 | 0 | 0 | — | — | 0 | 0 | 0 | 0 | 0 |
| 124 | 11.2100 | 0 | — | — | 0 | 0 | 0 | 0 | 0 | — | — | 0 | 0 | 0 | 0 | N |
| 125 | 11.2100 | 0 | 0 | 0 | 0 | 0 | 0 | 0 | 0 | 0 | 0 | — | — | — | — | — |
| 126 * | 11.2100 | 0 | — | — | 0 | 0 | 0 | 0 | 0 | — | — | 0 | 0 | 0 | 0 | 0 |
| 127 | 11.2100 | 0 | 0 | 0 | 0 | 0 | 0 | 0 | 0 | 0 | 0 | — | — | — | — | — |
| 128 | 11.2100 | 0 | 0 | 0 | 0 | 0 | 0 | 0 | 0 | 0 | 0 | — | — | — | — | — |
| 129 | 11.2100 | 0 | 0 | 0 | 0 | 0 | 0 | 0 | 0 | 0 | 0 | — | — | — | — | — |
| 130 | 11.2100 | 0 | 0 | 0 | 0 | 0 | 0 | 0 | 1 | 1 | 0 | — | — | — | — | — |
| 131 | 11.2100 | 0 | 0 | 0 | 0 | 0 | 1 | 0 | 2 | 1 | 2 | — | — | — | — | — |
| 132 | 11.2100 | 0 | — | — | 0 | 0 | 0 | 0 | 0 | — | — | 0 | 0 | 0 | 0 | 0 |
| 133 | 11.2100 | 0 | — | — | 0 | 0 | 0 | 0 | 0 | — | — | 0 | 0 | 0 | 0 | 0 |
| 134 | 11.2100 | 0 | — | — | 0 | 0 | 1 | 1 | 0 | — | — | 0 | 1 | 0 | 0 | 0 |
| 135 | 11.2100 | 0 | — | — | 0 | 2 | 1 | 1 | 1 | — | — | 1 | 1 | — | 0 | 1 |
| 136 | 11.2100 | 0 | — | — | 0 | 0 | 2 | 0 | 1 | — | — | 0 | 0 | N | 0 | 0 |
| 137 | 11.2100 | 0 | — | — | 0 | 0 | 0 | 0 | 0 | — | — | 0 | 0 | N | 0 | 0 |
| 138 | 11.2100 | 0 | 0 | 2 | 0 | 0 | 0 | 0 | 1 | 1 | 2 | — | — | — | — | — |
| 139 | 11.2100 | 0 | — | — | 0 | 0 | 0 | 0 | 0 | — | — | 0 | 0 | 0 | 0 | 0 |
| 140 | 11.2100 | 0 | — | — | 0 | 0 | 0 | 0 | 0 | — | — | 0 | 0 | 0 | 0 | 0 |
| 141 | 11.2100 | 0 | — | — | 0 | 0 | 0 | 0 | 0 | — | — | 0 | N | 0 | 0 | 0 |
| 142 | 11.2100 | 0 | 0 | 2 | 0 | 0 | 0 | 0 | 0 | 0 | 0 | — | — | — | — | — |
| 143 | 11.2100 | 0 | 0 | 2 | 0 | 0 | 0 | 0 | 0 | 0 | 0 | — | — | — | — | — |
| 144 | 11.2100 | 0 | 0 | 2 | 0 | 0 | 0 | 0 | 0 | 0 | 0 | — | — | — | — | — |
| 145 | 11.2100 | 0 | 0 | 0 | 0 | 0 | 0 | 0 | 0 | N | N | — | — | — | — | — |
| 146 | 11.2100 | 0 | 0 | 2 | 0 | 0 | 0 | 0 | 1 | 1 | 2 | — | — | — | — | — |
| 147 | 11.2100 | 0 | 0 | 2 | 0 | 0 | 0 | 0 | 0 | 0 | 0 | — | — | — | — | — |
| 148 | 11.2100 | 0 | — | — | 0 | 1 | 1 | 1 | 0 | — | — | 0 | 0 | 1 | 0 | 0 |

* NO SMARTWEED GERMINATION
POOR GERMINATION-SW
@ POOR SMARTWEED GERMINATION
] DAMPING OFF-IM.WB
: DAMPING OFF-IM.WB POOR GERMINATION-CB
. DAMPING OFF-IM.WB
K DAMPING OFF-LQ.

Compounds of this invention were also tested for herbicidal activity on weed plants in the presence of crop plants according to the following procedure:

Topsoil (silt loam) is sieved through a screen having 1.27 cm openings. In some of the tests the soil was mixed with fertilizer (1225 g/cu. m of 12/5/9 containing isobutylidene diurea), while in other tests the fertilizer was omitted. This mixture is steam sterilized and then placed in aluminum pans 6.985 cm deep having ten holes in the bottom each 0.635 cm in diameter. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with 1.27 cm of a mixture of 50% topsoil and 50% of a mixture of Canadian sphagnum peat moss, vermiculite and a wetting agent. The pans are then placed on a capillary mat on a greenhouse bench and subirrigated as needed. After the plants reach the desired stage (9 to 14 days, 1 to 3 true leaf stage), each pan (except the control pans) is removed to a spraying chamber and sprayed by means of an atomizer, operating at a spray pressure of 170.3 kPa (10 psig) at the application rates noted in Table D. In the spray solution is an amount of an emulsifying agent mixture (35% butylamine salt of dodecylbenzenesulfonic acid and 65% tall oil condensed with ethylene oxide in the ratio of 11 mol of ethylene oxide/mol of tall oil) to give a spray solution or suspension. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered as before and the injury to the plants as compared to the control pans is observed at approximately 10–14 days (usually 11 days).

In the following Table D the legends used to identify the plant species are the same as those used in the preceding Table B.

TABLE D

| Ex. No. | | Rate Kg/ha | Sobe | Cotz | Rape | Cobu | Wibw | Mogl | Hese | Jiwc | Velc | Whez | Rice | Grso | Corn | Dobr | Prmi | Bygr | Lacg | Grft | Subc | Colq | Pesw | Cocw |
|---|---|---|---|---|---|---|---|---|---|---|---|---|---|---|---|---|---|---|---|---|---|---|---|---|
| | | | | | | | Herbicide Secondary Post, spectrums 26, 88, 91, 93, 95, 96, and 100 (C = 100% control) | | | | | | | | | | | | | | | | | |
| 17 | & | 11.2100 | 2 | 3 | 3 | 1 | 3 | 2 | 2 | 3 | 2 | 0 | 0 | 1 | 3 | 0 | 0 | 2 | 3 | 2 | — | — | — | — |
| | & | 5.6050 | 2 | 1 | 2 | 0 | 3 | 2 | 3 | 3 | 2 | 0 | 0 | 0 | 2 | 0 | 0 | 1 | 3 | 2 | — | — | — | — |
| | & | 1.1210 | 1 | 2 | 1 | 0 | 1 | 1 | N | 2 | 3 | 0 | 0 | 0 | 0 | 0 | 1 | 0 | 3 | 0 | — | — | — | — |
| | & | 0.2803 | 0 | 1 | 0 | 0 | 1 | 0 | N | 2 | 2 | 0 | 0 | 0 | 0 | 0 | 1 | 1 | 3 | 0 | — | — | — | — |
| 70 | | 5.6050 | 0 | 0 | 0 | 0 | 2 | 0 | 1 | 0 | 0 | 1 | 0 | 2 | 3 | 0 | 2 | 0 | 2 | 0 | — | — | — | — |
| | | 1.1210 | 0 | 0 | 0 | 0 | 0 | 0 | 0 | 0 | 0 | 0 | 0 | 0 | 1 | 0 | 0 | 0 | 0 | 0 | — | — | — | — |
| | | 0.2803 | 0 | 0 | 0 | 0 | 0 | 0 | 0 | 0 | 0 | 0 | 0 | 0 | 0 | 0 | 0 | 0 | 0 | 0 | — | — | — | — |
| | | 0.0701 | 0 | 0 | 0 | 0 | 0 | 0 | 0 | 0 | 0 | 0 | 0 | 0 | 0 | 0 | 0 | 0 | 0 | 0 | — | — | — | — |
| 74 | & | 5.6050 | 2 | 0 | 1 | 0 | 1 | 2 | 1 | — | 1 | 0 | 0 | 1 | 2 | 0 | 0 | 0 | 3 | 1 | — | — | — | N |
| | & | 1.1210 | 1 | 0 | 0 | 0 | 1 | 1 | 1 | — | 1 | 0 | 0 | 0 | 1 | 0 | 0 | 0 | 3 | 0 | — | — | — | N |
| | & | 0.2803 | 0 | 0 | 0 | 0 | 0 | 0 | 0 | — | 0 | 0 | 0 | 0 | 0 | 0 | 0 | 0 | 1 | 0 | — | — | — | 0 |
| | & | 0.0701 | 0 | 0 | 0 | 0 | N | 0 | 1 | — | 0 | 0 | 0 | 0 | 0 | 0 | 0 | 0 | 0 | 0 | — | — | — | 0 |
| 75 | & | 5.6050 | 1 | 0 | 1 | 0 | 1 | 2 | 1 | — | 1 | 0 | 0 | 1 | 1 | 0 | 0 | 0 | 3 | 1 | — | — | — | N |
| | & | 1.1210 | 1 | 0 | 0 | 0 | 1 | 1 | 0 | — | 0 | 0 | 0 | 0 | 0 | 0 | 0 | 0 | 2 | 0 | — | — | — | N |
| | & | 0.2803 | 0 | 0 | 0 | 0 | 0 | 0 | 0 | — | 0 | 0 | 0 | 0 | 0 | 0 | 0 | 0 | 0 | 0 | — | — | — | 0 |
| 79 | | 11.2100 | 0 | — | — | 1 | 3 | 2 | 2 | — | 1 | 0 | 2 | 0 | 2 | 2 | 2 | 0 | 3 | 0 | 1 | 3 | 0 | — |
| | | 11.2100 | 0 | — | — | 2 | 3 | 3 | 3 | — | 0 | 0 | 3 | 0 | 2 | 0 | 2 | 0 | 3 | 0 | 1 | 3 | 0 | — |
| | | 5.6050 | 0 | — | — | 1 | 3 | 2 | 2 | — | 0 | 0 | 2 | 0 | 3 | N | 1 | 0 | N | 0 | N | 3 | 0 | — |
| | | 5.6050 | 1 | — | — | 2 | 3 | 1 | 1 | — | 0 | 0 | 2 | 0 | 2 | N | 2 | 0 | N | 0 | N | 2 | 0 | — |
| | | 2.8025 | 0 | — | — | 2 | 3 | 2 | 2 | — | 0 | 0 | 2 | 0 | 1 | 2 | 2 | 0 | N | 0 | 1 | 3 | 0 | — |
| | | 2.8025 | 0 | — | — | 2 | 3 | 2 | 2 | — | 1 | 0 | 3 | 1 | 1 | 2 | 3 | 0 | N | 0 | 0 | 2 | 0 | — |
| | | 1.1210 | 0 | — | — | 1 | 3 | 0 | 2 | — | 0 | 0 | 2 | 0 | 1 | 0 | 1 | 0 | 2 | 0 | 0 | 2 | 0 | — |
| | | 1.1210 | 0 | — | — | 1 | 3 | 2 | 1 | — | 1 | 0 | 1 | 0 | 1 | 0 | 1 | 0 | 2 | 0 | 1 | 2 | N | — |
| | | 0.5605 | 0 | — | — | 0 | 0 | 0 | 1 | — | 0 | 0 | 1 | 0 | 0 | 0 | 0 | 0 | 1 | 0 | 0 | N | 0 | — |
| | | 0.5605 | 0 | — | — | 0 | 0 | 0 | 0 | — | 0 | 0 | 0 | 0 | 0 | 0 | 0 | 0 | 2 | 0 | 0 | 2 | 0 | — |
| 89 | | 5.6050 | 2 | — | — | 1 | 3 | 2 | 0 | — | 2 | 1 | 0 | 0 | 2 | 0 | 0 | 1 | 1 | 0 | 2 | 2 | 1 | — |
| | | 1.1210 | 1 | — | — | 0 | 3 | 1 | 0 | — | 1 | 0 | 0 | 0 | 0 | 0 | 0 | 0 | 0 | 0 | N | 1 | 0 | — |
| | | 0.5605 | 1 | — | — | 1 | 2 | 1 | 0 | — | 0 | 0 | 0 | 0 | 0 | 0 | 0 | 0 | 0 | 0 | 1 | 1 | 0 | — |
| | | 0.2803 | 1 | — | — | 1 | 2 | 1 | 0 | — | 0 | 0 | 0 | 0 | 1 | 0 | 0 | 0 | 0 | 0 | 1 | 1 | 0 | — |
| | | 0.1401 | 1 | — | — | 1 | 2 | 0 | 0 | — | 1 | 0 | 0 | 0 | 0 | 0 | 0 | 0 | 0 | 0 | 1 | 1 | 0 | — |
| | | 0.0701 | 0 | — | — | 0 | 1 | 1 | 0 | — | 0 | 0 | 0 | 0 | 0 | 0 | 0 | 0 | 0 | 0 | 0 | 0 | 0 | — |

& Coded comments recorded only at the highest rate observed.

As can be seen from the data above, some of the compounds appear to be quite safe on certain crops and may be useful for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates. sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1-15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain 30 from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include N,-N-dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-d:α',1'-c)-pyrazidinium salt
5-Bromo-3-isopropyl-6-methyluracil 1,1'-dimethyl-4,4'-bipyridinium
2-(4-isopropyl-4-methyl-5-oxo-2-imidazolin-2-yl)- 3-quinolinecarboxylic acid
Isopropylamine salt of 2-(4-isopropyl-4-methyl-5- oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-N'-(3-chloro-4-methylphenyl) urea
3-(3,4-Dichlorophenyl)-1,1-dimethylurea 1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl-)amino)carbonyl)amino)sulfonyl)]benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate Carbamates/Thiolcarbamates 2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate Acetamides/Acetanilides/Anilines/Amides N,N-dimethyl-2,2-diphenylacetamide
N-(2,4-dimethyl-5-[[(trifluoromethyl)sulfonyl]amino]-phenyl]acetamide N-Isopropyl-2-chloroacetanilide
2',6'-Diethyl-N-methoxymethyl-2-chloroacetanilide
2'-Methyl-6'-ethyl-N-(2-methoxypropyl-2-yl)-2-chloroacetanilide
α,α,α-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-(sec-butyl)phenol N-(phosphonomethyl) glycine and its salts.
Butyl 2-[4-[(5-(trifluoromethyl)-2-pyridinyl)oxy]-phenoxy]-propanoate Ethers 2,4-Dichlorophenyl-4-nitrophenyl ether
5 2-Chloro-α,α,α-trifluoro-p-tolyl-3-ethoxy-4-nitrodiphenyl ether
5-(2-chloro-4-trifluoromethylphenoxy)-N-methyl sulfonyl
2-nitrobenzamide
1'-(Carboethoxy) ethyl 5-[2-chloro-4-(trifluoro methyl)-phenoxy]-2-nitrobenzoate Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below. When operating in accordance with the present invention, effective amounts of the compounds of this invention are applied to the soil containing the seeds, or vegetative propagules or may be incorporated into soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective pre-emergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*. Second Edition, Unabridged (1961). Thus, the term refers to any substance or medium in which vegetation may take root and grow, and includes not only earth but also compost, manure, muck, humus, sand, and the like, adapted to support plant growth.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skills in the art to which the invention pertains.

What is claimed is:

1. A compound represented by the formula

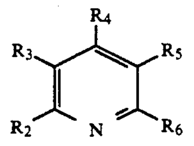

wherein $R_2$ and $R_6$ are independently bromoalkyl, chloroalkyl, fluoroalkyl, chlorofluoroalkyl, or alkoxy, provided that at least one of $R_2$ and $R_6$ is a fluoroalkyl;

$R_4$ is alkyl, cycloalkylalkyl, alkylthioalkyl, cycloalkyl, alkoxyalkyl, or dialkylaminoalkyl;

one of $R_3$ and $R_5$ is —C(O)—Y and the other is

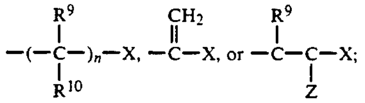

X is halogen, —OH, $—N_3$, $—SR^{11}$, $—OR^{11}$, $—NR^{12}R^{13}$, $—S(O)R^{11}$, $—S(O)_2R^{11}$, —CN, $—C(O)OR^{11}$, $—C(S)NH_2$, $—OC(O)R^8$, $—C(=NR^{12})SR^{11}$,

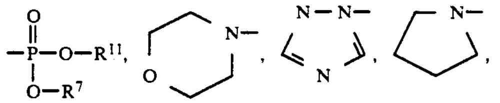

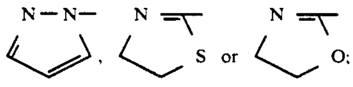

Y is alylthio, alkoxy, or a N-containing heterocycle;

Z is hydrogen, alkyl, or nitrile;

$R^9$ and $R^{10}$ are independently hydrogen, alkyl, alkenyl, or alkynyl;

$R^{11}$ and $R^7$ are independently alkyl;

$R^{12}$ and $R^{13}$ are independently hydrogen or alkyl;

$R^8$ is alkyl or haloalkyl; and n is an integer from 1 to 3 inclusive;

provided that when n is 1 and $R^9$ and $R^{10}$ are each hydrogen, X is not —OH.

2. The compound of claim 1 wherein one of $R_2$ and $R_6$ is $CF_3$ and the other is $CF_2H$.

3. The compound of claim 1 wherein $R_4$ is selected from $C_3$-$C_4$ branched chain alkyl groups.

4. The compound of claim 2 wherein $R_4$ is selected from cyclobutyl and cyclopropylmethyl.

5. The compound of claim 2 wherein Y is alkoxy.

6. The compound of claim 5 wherein Y is methoxy.

7. The compound of claim 5 wherein $R_3$ or $R_5$ is $—[C(R^9R^{10})]_n—X$.

8. The compound of claim 7 wherein X is halo, alkylthio, alkoxy, or cyano.

9. A herbicidal composition comprising an inert ingredient and an active ingredient of the formula

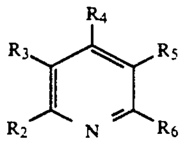

wherein $R_2$ and $R_6$ are independently bromoalkyl, chloroalkyl, fluoroalkyl, chlorofluoroalkyl, or alkoxy, provided that at least one of $R_2$ *I and* $R_6$ is a fluoroalkyl;

$R_4$ is alkyl, cycloalkylalkyl, alkylthioalkyl, cycloalkyl, alkoxyalkyl, or dialkylaminoalkyl;

one of $R_3$ and $R_5$ is —C(O)—Y and the other is

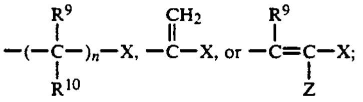

X is halogen, —OH, $—N_3$, $—SR^{11}$, $—OR^{11}$, $—NR^{12}R^{13}$, $—S(O)R^{11}$, $—S(O)_2R^{11}$, —CN, $—C(O)OR^{11}$, $—C(S)NH_2$, $—OC(O)R^8$, $—C(=NR^{12})SR^{11}$,

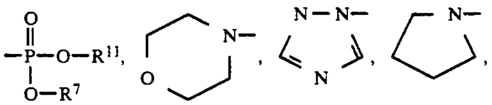

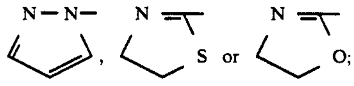

Y is alkylthio, alkoxy, or a N-containing heterocycle;

Z is hydrogen, alkyl, or nitrile;

$R^9$ and $R^{10}$ are independently hydrogen, alkyl, alkenyl, or alkynyl;

$R^{11}$ and $R^7$ are independently alkyl;

$R^{12}$ and $R^{13}$ are independently hydrogen or alkyl;

$R^8$ is alkyl or haloalkyl; and n is an integer from 1 to 3 inclusive;

provided that when n is 1 and $R^9$ and $R^{10}$ are each hydrogen, X is not —OH.

10. The composition of claim 17 wherein one of $R_2$ and $R_6$ is $CF_3$ and the other is $CF_2H$.

11. The composition of claim 10 wherein $R_4$ is selected from $C_3$-$C_4$ branched chain alkyl groups.

12. The composition of claim 10 wherein $R_4$ is selected from cyclobutyl and cyclopropylmethyl.

13. The composition of claim 10 wherein Y is alkoxy.

14. The composition of claim 13 wherein Y is methoxy.

15. The composition of claim 13 wherein $R_3$ or $R_5$ is $—[C(R^9R^{10})]_n—X$.

16. The composition of claim 15 wherein X is halo, alkylthio, alkoxy, or cyano.

* * * * *

UNITED STATES PATENT AND TRADEMARK OFFICE

CERTIFICATE OF CORRECTION

PATENT NO. : 5,169,432

DATED : December 8, 1992

INVENTOR(S) : Auinbauh et al.

It is certified that error appears in the above-identified patent and that said Letters Patent is hereby corrected as shown below:

On the title page, item [21], change "705,548" to --704,548--.

Column 19, line 39 "1.4698" should read --1.4723--.

Column 20, line 11 "4689" should read --1.4689--.

Column 21, line 17 "0%" should read --90%--.

Column 26, line 9 "1 5019" should read --1.5019--.

Column 28, line 49 "4644" should read --1.4644--.

Column 28, line 60 "14717" should read --1.4717--.

Column 74, line 43 before "overwatered", add --/--.

Column 79, line 30, add --A-- before "POOR GERMINATION-SW".

Signed and Sealed this

Thirteenth Day of September, 1994

Attest:

Bruce Lehman

BRUCE LEHMAN

*Attesting Officer*

*Commissioner of Patents and Trademarks*